United States Patent [19]

Richards-Kortum et al.

[11] Patent Number: 5,421,337

[45] Date of Patent: Jun. 6, 1995

[54] SPECTRAL DIAGNOSIS OF DISEASED TISSUE

[75] Inventors: Rebecca Richards-Kortum, Austin, Tex.; Lucene Tong, Boston; Michael S. Feld, Newton, both of Mass.

[73] Assignee: Massachusetts Institute of Technology, Cambridge, Mass.

[21] Appl. No.: 219,240

[22] Filed: Mar. 29, 1994

Related U.S. Application Data

[63] Continuation of Ser. No. 768,732, Dec. 10, 1991, abandoned, which is a continuation-in-part of Ser. No. 337,935, Apr. 14, 1989, abandoned.

[51] Int. Cl.⁶ .............................................. A61B 6/00
[52] U.S. Cl. .................................................... 128/665
[58] Field of Search ............................ 128/6, 633–634, 128/664–665; 436/171–172

[56] References Cited

U.S. PATENT DOCUMENTS

| | | |
|---|---|---|
| 3,327,119 | 6/1967 | Kamentsky. |
| 4,556,057 | 12/1985 | Hiruma et al.. |
| 4,676,231 | 6/1987 | Husazumi et al.. |
| 4,693,556 | 9/1987 | McCaughan, Jr.. |
| 4,718,417 | 1/1988 | Kittrell et al.. |
| 4,768,513 | 9/1988 | Suzuki ................................ 128/634 |
| 4,773,097 | 9/1988 | Suzaki et al. ........................... 382/6 |
| 4,785,806 | 11/1988 | Deckelbaum .................... 128/666 X |
| 4,786,813 | 11/1988 | Svanberg et al. ................. 250/461.1 |
| 4,930,516 | 6/1990 | Alfano et al.. |
| 4,957,114 | 9/1990 | Zeng et al. ........................... 128/665 |
| 4,981,138 | 1/1991 | Deckelbaum et al. ............... 128/665 |
| 5,003,977 | 4/1991 | Suzuki et al. ........................ 128/633 |
| 5,201,318 | 4/1993 | Rava et al. ............................ 128/665 |
| 5,345,941 | 9/1994 | Rava et al. ............................ 128/665 |

FOREIGN PATENT DOCUMENTS

| | | |
|---|---|---|
| 929050 | 5/1982 | U.S.S.R.. |
| WO90/00035 | 6/1989 | WIPO. |

OTHER PUBLICATIONS

"Autofluorescence of Various Rodent Tissues and Human Skin Tumour Samples" Anderson et al.
"Immunofluorescence studies on the occurrence and localization of the CEA-related biliary glycoprotein I (BFP I) in normal human gastrointestinal tissues". Svenberg et al., Publication of Karolinska Hospital.
"Laser Induced Flourescence Studies of Hematoporphyrin Derivative (HPC) in Normal and Tumor Tissue of Rat", Ankerst et al., *Applied Spectroscopy*, vol. 38, No. 6, 1984 pp. 890–896.
"Tissue characterization using laser-induced fluorescence", Anderson et al. *Tuesday Morning*, Apr. 28 pp. 46–48.
"Contrast enhancement in tumor localization using hemotoporphyrin derivative laser-induced fluorescence", Ankerst et al., *Friday Morning*, Jun. 22 pp. 234–235.
"Multicolor Imaging and Contrast Enhancement in Cancer Tumor Localization using laser-induced fluorescence in hematoporphyrin derivative-bearing tissue", Montan et al., *Wednesday Morning*, May 22, pp. 82–84.
"Spectral Characteristics in Tissue Diagnostics using Laser-Induced Fluorescnece", Ankerst et al., *ICALEO* vol. 43, 1984, pp. 52–60.
"Multispectral System for Medical Fluorescence Imaging", Anderson et al., *IEEE Journal of Quantum Electronics*, vol. QE–23 No. 10, Oct. 1987, pp. 1798–1805.

(List continued on next page.)

*Primary Examiner*—Angela D. Sykes
*Attorney, Agent, or Firm*—Hamilton, Brook, Smith & Reynolds

[57] ABSTRACT

The present invention relates to a method and apparatus for diagnosing the condition of gastrointestinal tissue. The method and apparatus excite fluorophores within a portion of gastrointestinal tissue with a laser to cause the fluorophores to emit fluorescent radiation. The presence of abnormal tissue is then determined by detecting the radiation emitted by the excited fluorophores and comparing the emitted radiation to a reference emission for fluorophores within normal tissue at predetermined wavelengths.

26 Claims, 46 Drawing Sheets

OTHER PUBLICATIONS

"Fluorescence Studies of Hematoporphyrin Dirative in Normal and Malignant Rat Tissue", Svanberg et al., *Cancer Research* Aug. 1986 pp. 3803–3808.

"Spectral Studies of GI Tissues: Optimizing Excitation and Emission Wavelengths for Discrimination of Normal and Adenomatous Tissues", Kortum Abstract.

"Tumor Localization by Means of Laser–Induced Fluorescence in Hematoporphyrin Derivative (HPD)–Bearing Tusue", Anderson et al. Proceedings of the Seventh International Conference *Laser Spectroscopy VII*, Jun. 24–28 1985.

"Multicolor imaging and contrast enhancement in cancer–tumor localization using laser–induced fluorescence in hematopotphyrin–derivative–bearing tissue", Montan et al., *Optics Letters*, vol. 10 No. 2 Feb. 1985 pp. 56–58.

Alfano, Robert R., et al., "Laser Induced Fluorescence Spectroscopy from Native Cancerous and Normal tissue", *Journal of Quantum Electronics*, AE20 (12):1507–1511, Dec. (1984).

Dal Fante, Marco, et al., "Behaviour of Haematoporphyrin Derivative in Adenomas and Adenocarcinomas of the Colon: a Microfluorometric Study", *Lasers in Medical Science*, 3:165–171, (1988).

Kapadia, Cyrus R., et al., "Laser–Induced Fluorescence Spectroscopy of Human Colonic Mucosa, Detection of Adenomatous Transformation", *Gastroenterology* 99 (1): (1990).

Yuanlong, Yang, et al., "Characteristic Autofluorescence for Cancer Diagnosis and Its Origin", *Lasers in Surgery and Medicine*, 7:528–532 (1987).

Cothren, R. M., Ph.D., et al., "Gastrointestinal tissue diagnosis by laser–induced fluorescence spectroscopy at endoscopy", *Gastrointenstinal Endoscopy*, 36 (2): 105–111, (1990).

SPECTRAL DIAGNOSIS OF DISEASED TISSUE

RELATED APPLICATION

This application is a continuation of application Ser. No. 07/768,732 filed Dec. 10, 1991, now abandoned, (U.S. Phase of Int'l PCT/US90/01914 filed Apr. 9, 1990) now abandoned, which is a continuation-in-part of U.S. Ser. No. 07/337,935 filed Apr. 14, 1989, now abandoned.

BACKGROUND OF THE INVENTION

The present invention relates to the field of diagnosis of bodily tissue, and more particularly, to the differentiation of normal from abnormal tissue using laser-induced fluorescence to provide diagnostic information regarding the condition of tissue.

Endoscopic diagnosis is based on the gross morphologic characteristics of tissue, including gastrointestinal and colonic abnormalities, for example. An appraisal of the pathologic condition of many lesions or abnormalities can be made by endoscopic observation alone, but there remains a margin for error that can be substantial for certain types of lesions. Microscopic assessment of biopsy specimens is often considered necessary for many lesions discovered during endoscopy. Furthermore, certain abnormalities of a microscopic nature such as dysplasia in chronic ulcerative colitis or Barrett's esophagus, for example, are usually unrecognizable by gross endoscopic observation.

Of critical concern in the diagnosis of gastrointestinal tissue is the presence and condition of polyps. A polyp of the colon can be defined as any lesion that protrudes above the surface of the surrounding mucosa. See Robbins, S. L., Cotran, R. S. and Kumar, E., *Pathogenic Basis of Disease*, 1984, pp. 863–869. There are two broad categories of mucosal polyps: Hyperplastic (~90%) and adenomatous (~10%). Adenomatous polyps are true neoplasms and sometimes harbor areas of carcinoma. Adenomatous polyps can be subdivided into three classes: tubular (~75%), tubulovillous (~5–15%), and villous (~10–15%). There is a general correlation between the type of polyp, and its size and potential for harboring cancer. Hyperplastic polyps are the smallest, tubular adenomas are next in size, and villous adenomas are largest. Hyperplastic polyps are almost always benign. Overall, the incidence of carcinomas in tubular adenomas is about 3–5%. However, somewhere between 25 and 50% of villous adenomas contain carcinomas (See Robbins, supra., at pp. 863–869).

Histologically, hyperplastic polyps are composed of well-formed glands and crypts lined by non-neoplastic epithelial cells, most of which are well differentiated. Tubular adenomas have slender stalks and rounded heads. They are composed of a central core of fibro-vascular tissue and are covered by an epithelium of elongated tubules and glands in which cells are not well differentiated. Marked nuclear hyperchromasia and an increase in the nuclear to cytoplasm ratio are usually present. A range of dysplasia and nuclear atypia is encountered. Villous adenomas are composed of finger-like pappillae covered by polypoid epithelium. Each papilla is composed of a fibro-vascular core covered by epithelium. Tubular adenomas having between 20–50% villous growth are referred to as tubulo-villous (See Robbins, supra., at pp. 863–869).

In familial multiple polyposis of the colon, the colon is covered by a myriad of neoplastic polyps after the second and third decades of life. The individual polyps are small and mostly tubular. Multiple polyposis inevitably develops into cancer (See Robbins, supra, at pp. 863–869).

Methods have been developed to detect the presence of abnormal or cancerous tissue using laser-induced-fluorescence spectroscopy. Typically, dyes or stains which are known to have a particular fluorescence spectrum and which are selectively retained by the abnormal tissue of interest, or which can be brought directly into contact with that tissue, are used to identify the diseased state of the tissue. More specifically, the emission spectrum produced by the fluorescing dye can be used to locate abnormal tissue within the body and identify its condition.

Laser catheter systems have been developed for the purpose of inserting a light transmitting device into the human body to provide endoscopic examination of the tissue located in front of the catheter. The light emitted by the stained tissue due to the induced fluorescence can be transmitted along the catheter and analyzed at the proximal end of the catheter to produce an emission spectrum for the tissue being illuminated.

Use of dyes or stains for diagnosis has a number of disadvantages. Typically, different tissue types require different materials which must be tested extensively prior to their use in humans. Thus, a need exists for a method and apparatus for not only observing polyps in gastrointestinal tissue but distinguishing between types of polyps without introducing stains or dyes.

SUMMARY OF THE INVENTION

The present invention relates to the use of fluorescence spectroscopy to diagnose the presence of abnormal tissue during in vivo examination and in biopsied samples. Samples of normal and polypoid gastrointestinal tissue removed from patients with familial multiple polyposis have been examined using methods of fluorescence spectroscopy. Patients having colonic adenomas, hyperplastic polyps, or normal mucosa were examined during endoscopy using the present methods of fluorescence spectroscopy. Specific ranges of excitation and emission wavelengths have been found to accurately diagnose the presence of abnormal tissue both in vivo and in vitro using "autofluorescence", that is, the fluorescence of tissue without the use of fluorescence enhancing agents.

The present methods of tissue spectroscopy can be utilized to differentiate normal colonic mucosa and hyperplastic polyps from adenomatous polyps without the use of fluorescing agents such as dyes or stains. Surgically resected specimens of either normal or abnormal gastrointestinal tissue, as well as the tissue examined in vivo, have been irradiated with laser radiation generally in the range between 200 and 450 nm. Various methods are used to analyze the emission spectra to assess the condition of the tissue being examined. Generally the emission wavelengths longer than 400 nm are used to differentiate normal and abnormal tissue. More specifically, differences between the emission spectra and reference spectra obtained from measurements of normal tissue are analyzed to determine functions which discriminate between normal and abnormal tissue. The standard deviation of emission spectra were calculated and used to assist in the determination of diagnostically significant wavelengths for gastrointestinal tissue. The methods of spectral diagnosis described herein can be used in vivo with a laser catheter system that can diagnose and treat the specific tissue of interest.

Specific morphological or biochemical constituents of the tissue under study have been identified in which fluorescence can be induced and whose to the fluorescence spectrum in the tissue is correlated with particular abnormalities.

The distinctive features identified in emission spectra as being diagnostically significant correspond to these chemical constituents and are used to measure the concentration of these constituents in the tissue. The spectra can be deconvolved to isolate the different components of the tissue and their relative contributions.

The above, and other features of the invention including various novel details in the methods described and certain combinations thereof, will now be more particularly described with reference to the accompanying drawings and pointed out in the claims. It will be understood that the particular methods of diagnosis embodying the invention are shown by way of illustration only and not as a limitation of the invention. The principle features of the invention may.be employed in various embodiments without departing from the scope of the invention.

BRIEF DESCRIPTION OF THE DRAWINGS

FIGS. 44a-f shows emission spectra of selected chromophore.

DETAILED DESCRIPTION

Low power laser illumination can induce endogenous tissue fluorescence (autofluorescence) with spectral characteristics that depend upon physicochemical composition of the tissue. Fluorescence emission and attenuation (reabsorption and scattering) can be measured and provide the basis of a diagnostic system adapted to endoscopy. Autofluorescence can be used to differentiate adenoma from normal mucosa for in vitro measurements for tubular adenomas found in patients with familial adenomatous polyposis. The following demonstrates that the excitation wavelength 370 nm was optimal for in vitro discrimination of adenomas from normal tissue, however the excitation wavelengths 330 nm and 430 nm have also be used to effectively distinguish normal from abnormal tissue. Thus a range of wavelengths has been identified that provides an effective diagnostic procedure.

The colonic adenoma provides a procedure that reveals definite endoscopic and pathologic differences between normal and abnormal (adenomatous) tissue. Laser induced fluorescence (LIF) spectroscopy has clinical significance in relation to the problem of the "adenoma-carcinoma" sequence that is known to underlie the development of colon cancer. It is well established that endoscopic differentiation of adenomatous from nonadenomatous polyps is not possible in the case of small lesions. Management of these polyps may be problematic in a number of ways. A biopsy is necessary for accurate diagnosis, but should a lesion prove to be an adenoma it may be difficult to locate it a second time for definitive treatment. The immediate treatment of diminutive polyps upon discovery means that patients with nonadenomatous lesions incur an unnecessary, albeit small, risk of a complication as well as the additional cost of treatment. Although LIF spectroscopy improves the management of small colon polyps, the method has additional applications with respect to the diagnosis of other mucosal disorders that are more difficult to recognize endoscopically. The benign adenoma is similar to dysplastic epithelium found in other conditions so that information derived from LIF spectroscopy of adenomatous tissue can be applied to the recognition of dysplastic mucosa in disorders such as Barrett's esophagus or chronic ulcerative colitis.

Figure 1:
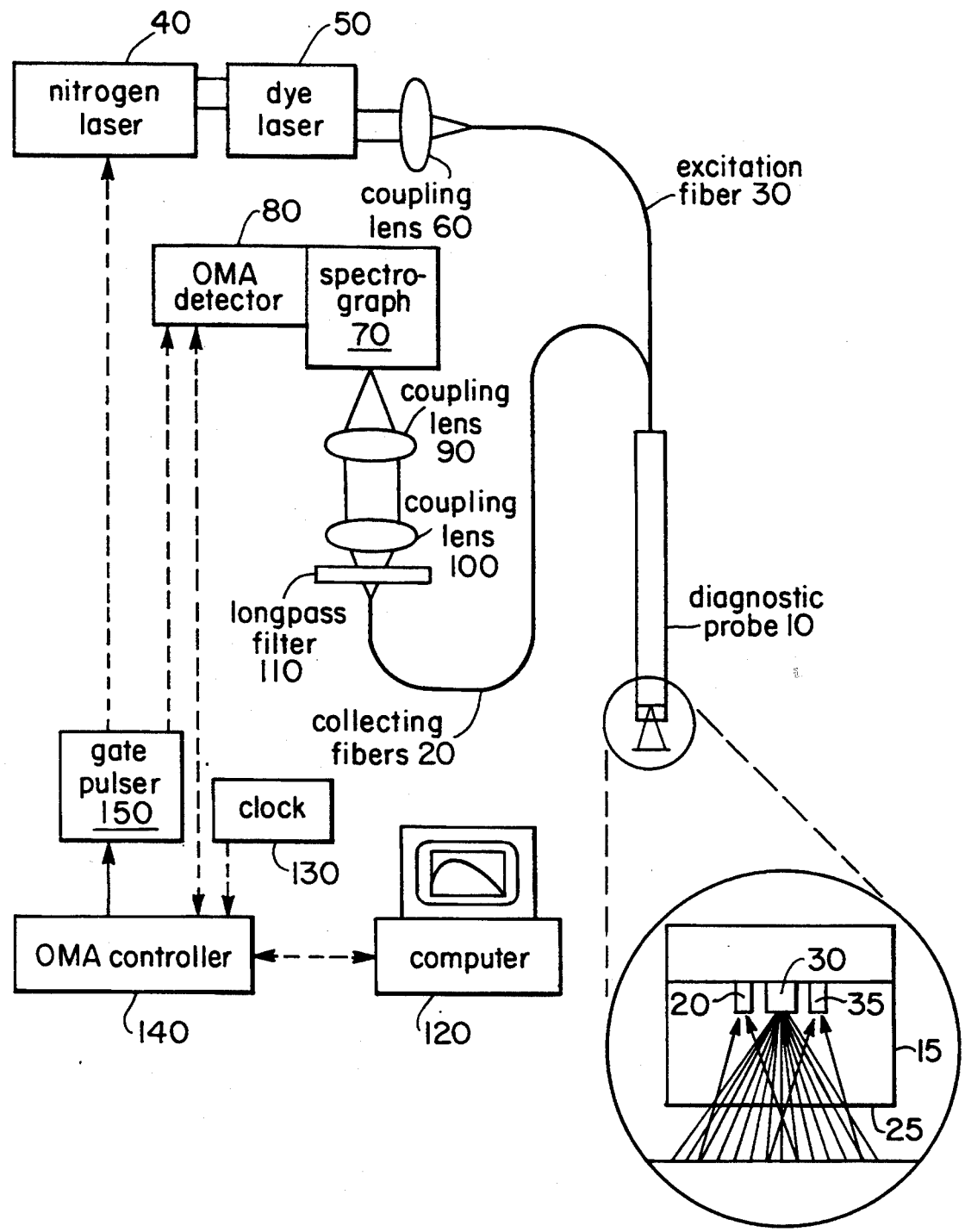
FIG. 1 illustrates a system for collecting spectra that are used to diagnose tissue condition.
Figure 1A:
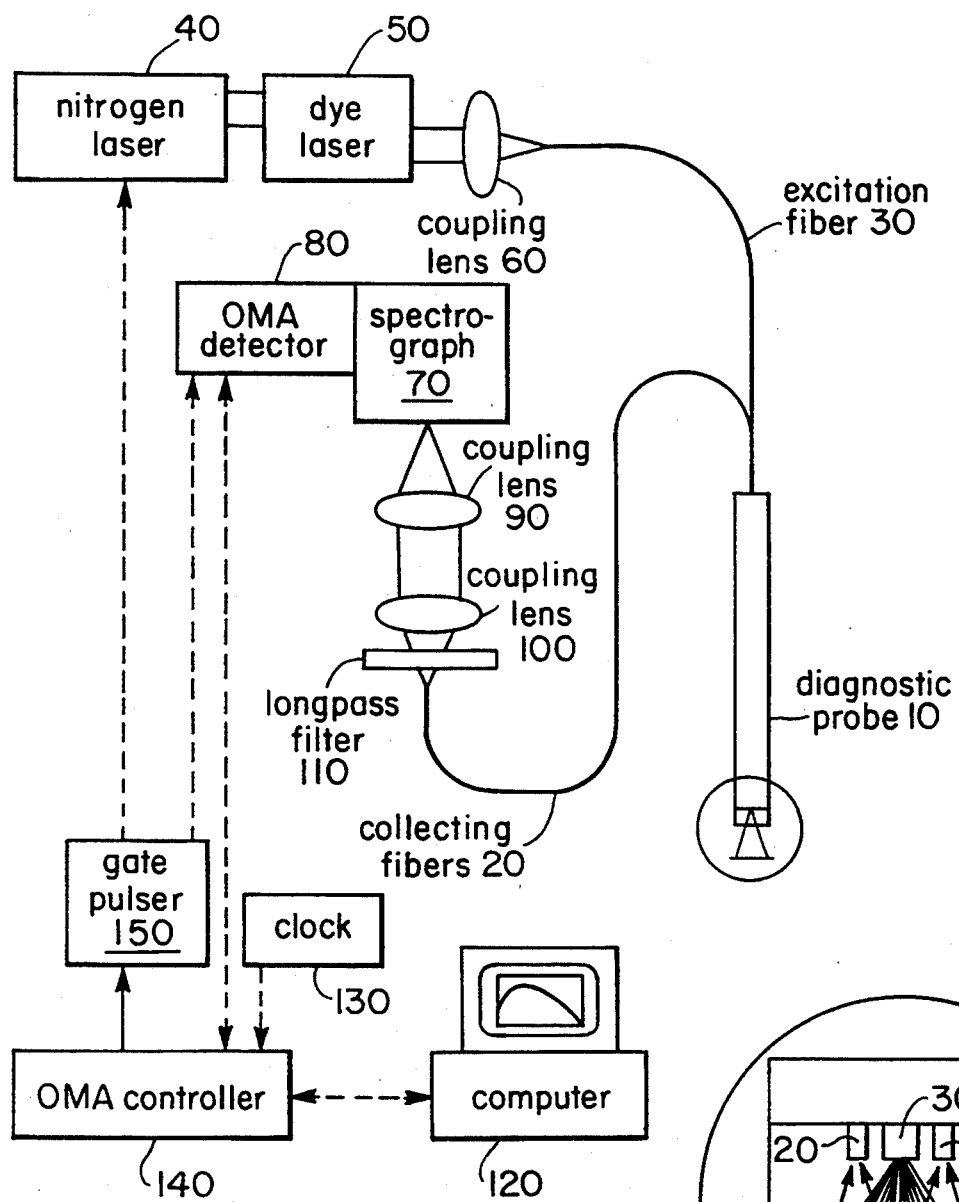
Figure 1B:
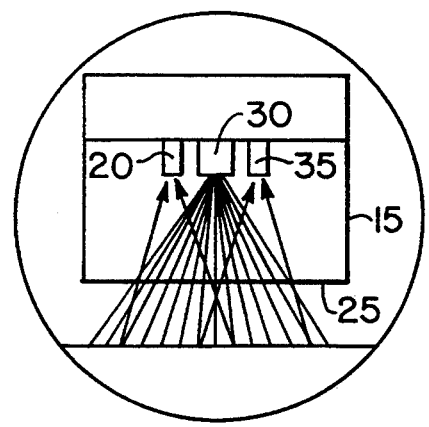

A spectrofluorometry system employed to collect mucosal fluorescence spectra in vivo is illustrated in FIG. 1. An optical fiber fluorescence probe 10 was constructed that could be passed through the accessory channel of a standard colonoscope. The probe 10 delivers monochromatic light at 370 nm produced by a nitrogen laser 40-pumped dye laser 50 through a centrally placed excitation optical fiber 30. This light forms a 1 mm diameter excitation spot at the distal tip 25 of a 1 mm diameter transparent quartz outer shield 15. This system can be used to deliver excitation light spanning the spectral region 360 nm–1.0 μm. At 370 nm excitation, the laser furnishes an average power of 270 μW at the distal tip, delivered in 3 nanosecond pulses at 20 Hz. Nine smaller peripherally placed optical fibers 20 surround the central excitation fiber. These collect the emitted tissue fluorescence only from the surface area directly illuminated by the excitation light. The system has a well-defined excitation and collection geometry so that light that is scattered to the tissue surrounding the illuminated area is not collected. By substantially reducing the amount of light collected from the non-illuminated area more uniform spectroscopic measurements are obtained.

The proximal ends of the nine collection fibers 20 were imaged at the entrance slit of an imaging spectrograph 70 coupled to a gated optimal multichannel detector 80 under computer control from optimal multichannel controller 140 and computer 120. A 399 nm long pass, low fluorescence filter 110 was used to block scattered excitation light from the detector. Coupling lens 90, 100 directed the filtered light to the spectrograph 70 input. A 1.0 microsecond collection gate pulser 150 synchronized by clock 130 to the laser pulse effectively eliminated the effects of the colonoscope's white illumination light during collection of the weaker tissue fluorescence.

The use of fluorescence spectroscopy to differentiate gastrointestinal tissues as normal or adenomatous is based upon excitation in a range of wavelengths between 200 and 450 nanometers with the 370 nm excitation providing the highest correlation. Intensities of emission spectra collected between 300 and 600 nm were analyzed to assess the diagnostic significance of the spectroscopic method. Generally, three groups of data have been taken in vitro based upon certain differences in the experimental procedure and analysis that was utilized to assess the spectra.

The procedure followed for the first group of samples included a total reflectance spectrum that was measured using a integrating sphere absorption spectrophotometer. A spectofluorimeter was used to measure fluorescence excitation and emission spectra of each sample. Excitation spectra were measured at emission wavelengths varying from 350 to 600 nm in 50 nm steps. Peaks in the excitation spectra were noted, and emission spectra were measured at corresponding excitation wavelengths. The first group was analyzed using ratios of emission intensities at wavelengths that produced a high degree of correlation between the actual condition of the tissue and the spectrally determined condition.

The second group of in vitro samples used the same procedure for measuring the emission spectra, but a different method of analyzing the spectra. In particular, difference and discriminant functions were defined which produced diagnostically significant information regarding the samples examined. Finally, the gratings in an emission monochromator were changed from 500 nm blaze to 250 nm blaze for those samples in the second group. This allowed for greater efficiency at UV wavelengths, and thus, for a greater signal-to-noise ratio in this region of the spectrum.

For a third group of in vitro samples, a slightly different procedure was followed. A total reflectance spectrum was measured using an absorption spectrophotometer. Fluorescence emission spectra were recorded at 290, 330, 350, 370 and 476 nm excitation. These excitation wavelengths were chosen as they correspond to the most consistent excitation peaks present in both the normal and adenomatous samples of the first group. In recording these fluorescence spectra, several improvements were made in the fluorimeter. The excitation beam size was reduced from ~2×10 mm to ~2×3 mm, making it possible to excite only specific polypoid regions of samples. In addition, this allowed the measurement of calibrated intensity Information for the samples of the third group, as the excitation beam size was always smaller then the sample surface area.

All of the spectra described in FIGS. 1–9, 13–14, 19–20, and 24 have been corrected for the non-uniform spectral response of the collection system.

Excitation spectra of samples in the first group (FIGS. 2–7) indicated that excitation peaks at 290, 330, 350, 370, and 376 nm were common to most normal and adenomatous tissues. Therefore, emission spectra were recorded at each of these excitation wavelengths for each sample in the second group, and most of those in the first group.

At each excitation wavelength the following data analysis procedure was followed. Fluorescence spectra of normal and tumor tissues were normalized to 1 at a particular wavelength. Normalization wavelengths were chosen at the point corresponding to the maximum fluorescence intensity in the normal tissue fluorescence spectrum. This generally corresponded to a region in which the emission of normal and adenomatous tissues were similar.

Figure 2A:
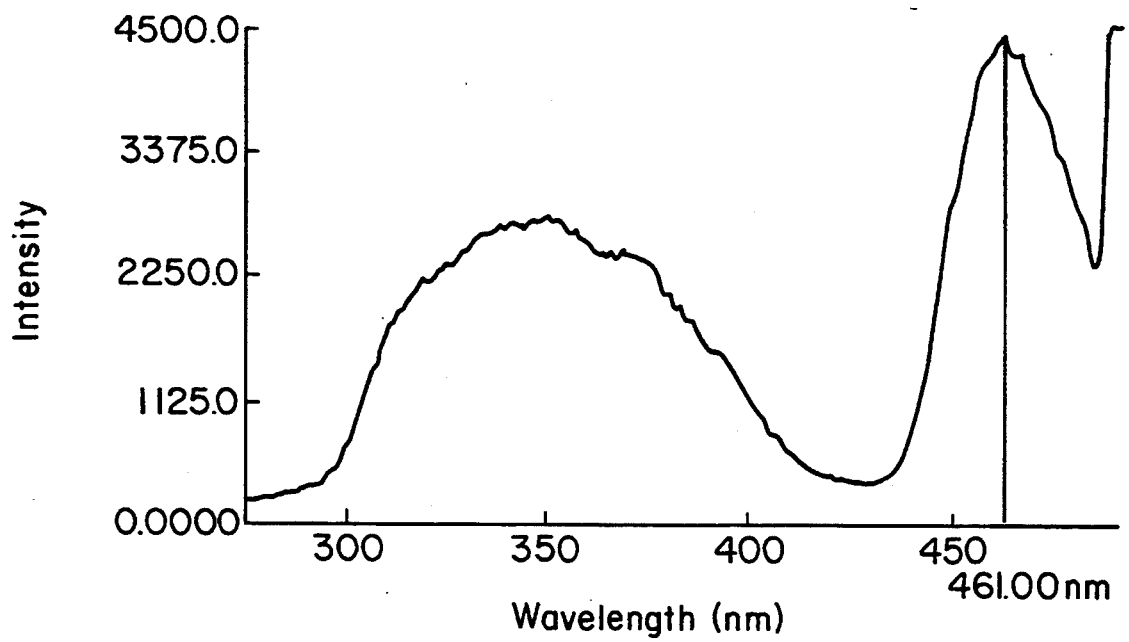
FIG. 2 illustrates excitation spectra of (a) normal and (b) polyp tissues at an emission wavelength of 500 nm.
FIG. 2c illustrates emission spectra of normal and (d) polyp tissues at an excitation wavelength of 290 nm.
Figure 2B:
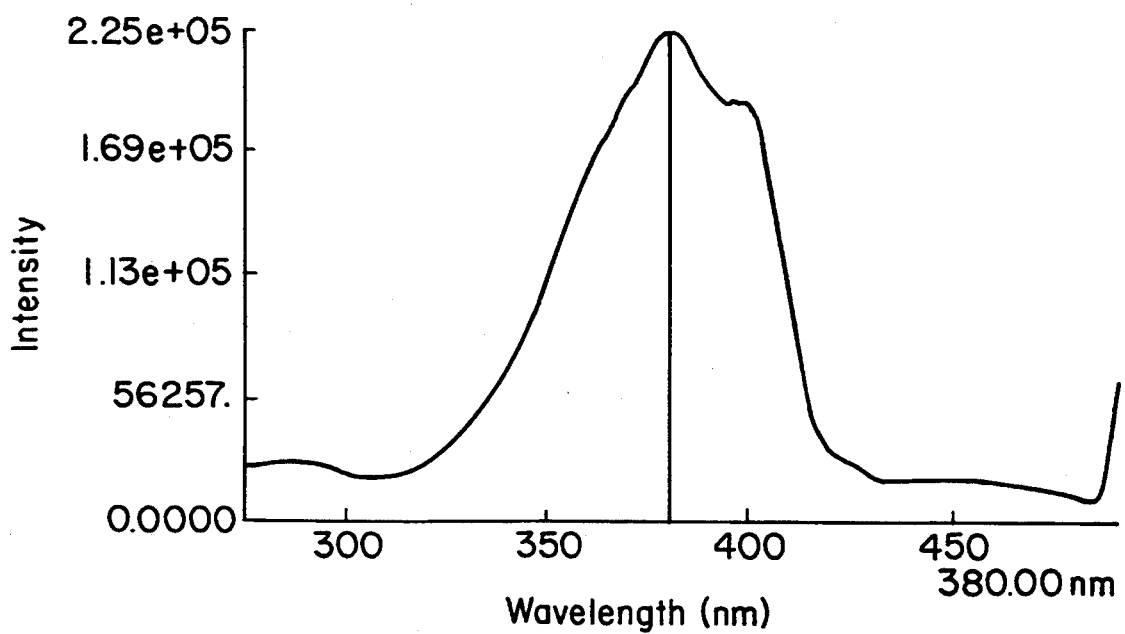

FIG. 2(a) is a plot of fluorescence emission intensity versus excitation wavelength in nanometers for normal tissue, at 500 nm emission. A broad excitation peak is present from 300–400 nm, with several sub-maxima at 310, 330, 350 and 370 nm. A second excitation peak is found at 460 nm. About half of the polyp samples showed a similar excitation spectrum, however, the other half showed an excitation spectrum typical of that in FIG. 2(b). This shows a narrower excitation peak at 380 nm with a shoulder at 400 nm. A smaller excitation peak at 460 nm is also present. Emission spectra were collected at all peaks of the various excitation spectra; however, emission spectra obtained with 290, 350, and 370 nm excitation are particularly suited for differentiating normal and polyp samples. Results obtained with these wavelengths will be described here.

Figure 2C:
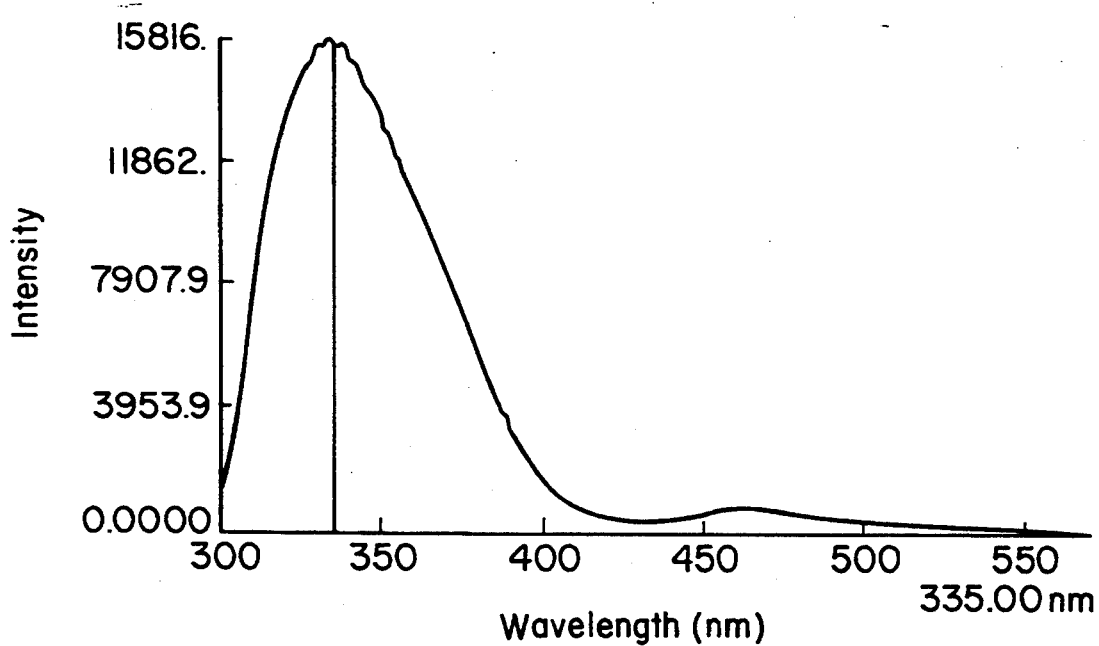
Figure 2D:
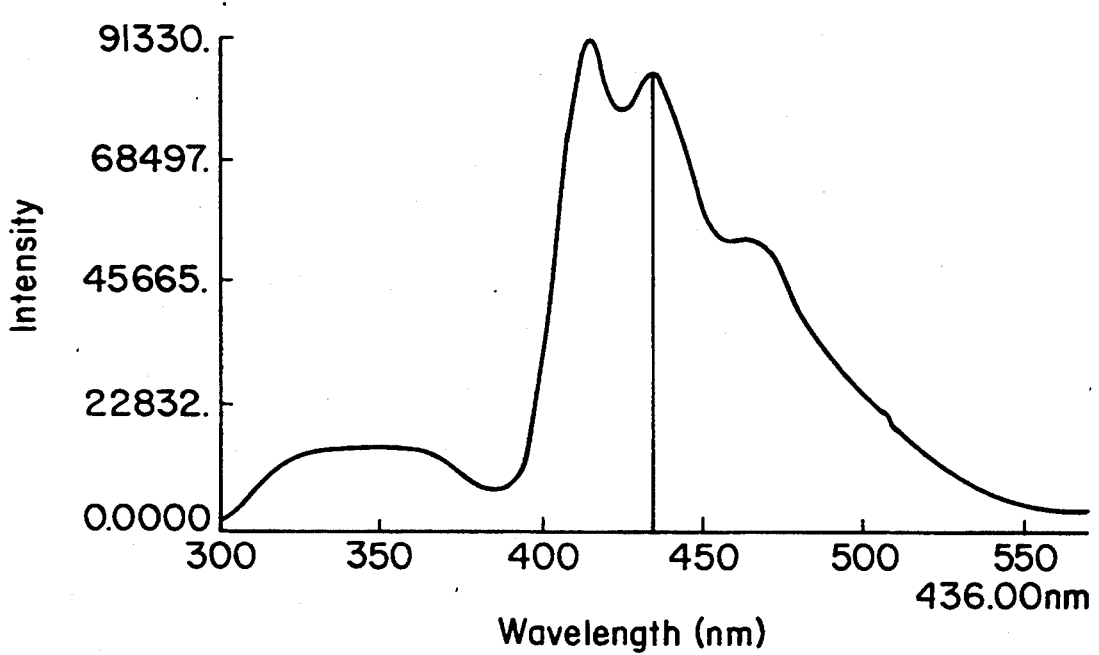

FIG. 2(c) shows typical emission spectra at 290 nm excitation for normal tissues. About half of the polyp tissues showed similar emission spectra. The other half (marked with an asterisk in Table 1) had spectra typical of those shown in FIG. 2(d). This unique emission profile always correlated with the unique excitation profile shown in FIG. 2(b). Several differences between FIGS. 2(c) and (d) are immediately obvious. The polyp spectrum shows a peak near 340 nm and a three-peaked structure at 415, 440 and 460 nm, whereas the normal spectrum exhibits a peak at 340 nm and only a single peak at 460 nm. This 460 nm peak is more intense, relative to the 340 nm peak, in polyp spectra. Also, the peak at 340 nm appears to be broader, on the long wavelength side, in spectra of polyp tissues.

To correlate features of these fluorescence spectra to tissue type in a quantitative way for all samples, several empirical methods have been devised, including ratios of fluorescence intensities at the following wavelengths: 335/365, 335/440, 440/390, 415/425, and 440/457. Although many combinations of wavelengths were tried, these were found to clearly indicate separation of samples according to sample type. The value of these ratios versus tissue type are shown in FIG. 3(a–d). The following table lists the average values and standard deviations for each ratio vs. tissue type.

TABLE 1

| Ratio | Average Value (± std. dev.) for: Normal | Polyp |
|---|---|---|
| 335/365 | 1.63 ± 0.13 | 1.24 ± 0.11 |
| 335/440 | 39.2 ± 6.1 | 10.8 ± 11.2 |
| 440/390 | 0.12 ± 0.009 | 2.67 ± 3.32 |
| 415/425 | 1.66 ± 0.11 | 1.11 ± 0.10 |
| 440/457 | | |

Figure 3A:
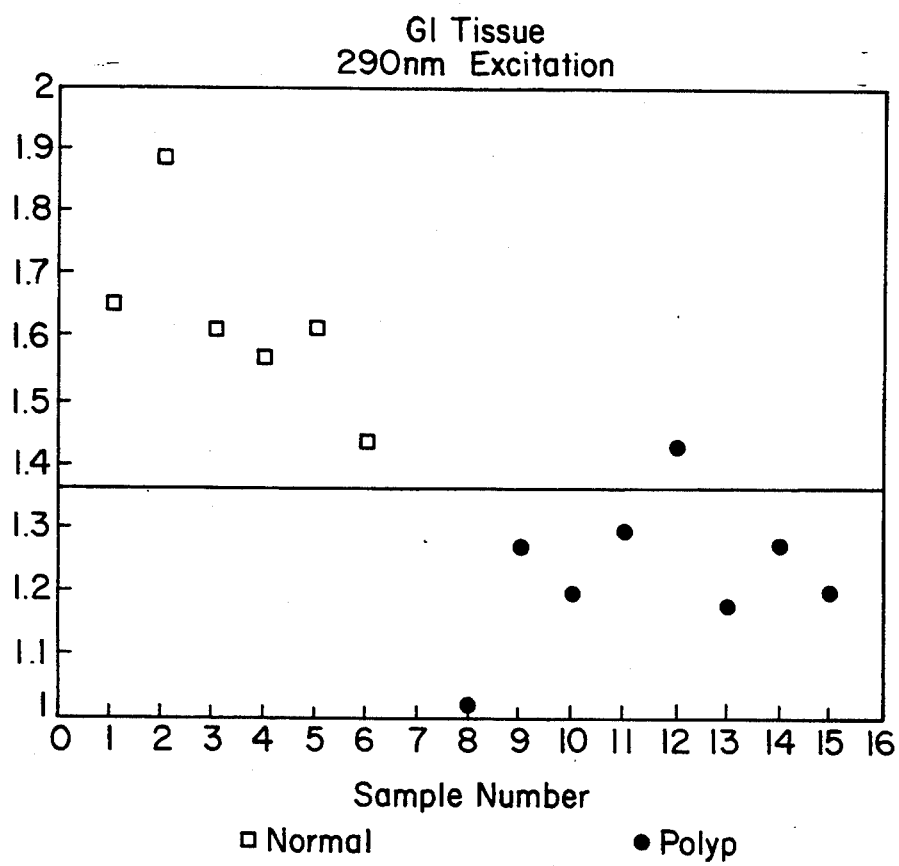
FIG. 3 shows values of intensity ratios at (a) 335 nm/365 nm, (b) 335 nm/440 nm, (c) 440 nm/390 nm, (d) 415 nm/425 nm, and (e) 440 nm/457 nm. In each figure, the solid lines indicate a criterion for determining tissue type from the value of the ratio. In (a) and (b), 94% accuracy is achieved with this criterion; in (c) and (d), the accuracy is 100%.
Figure 3B:
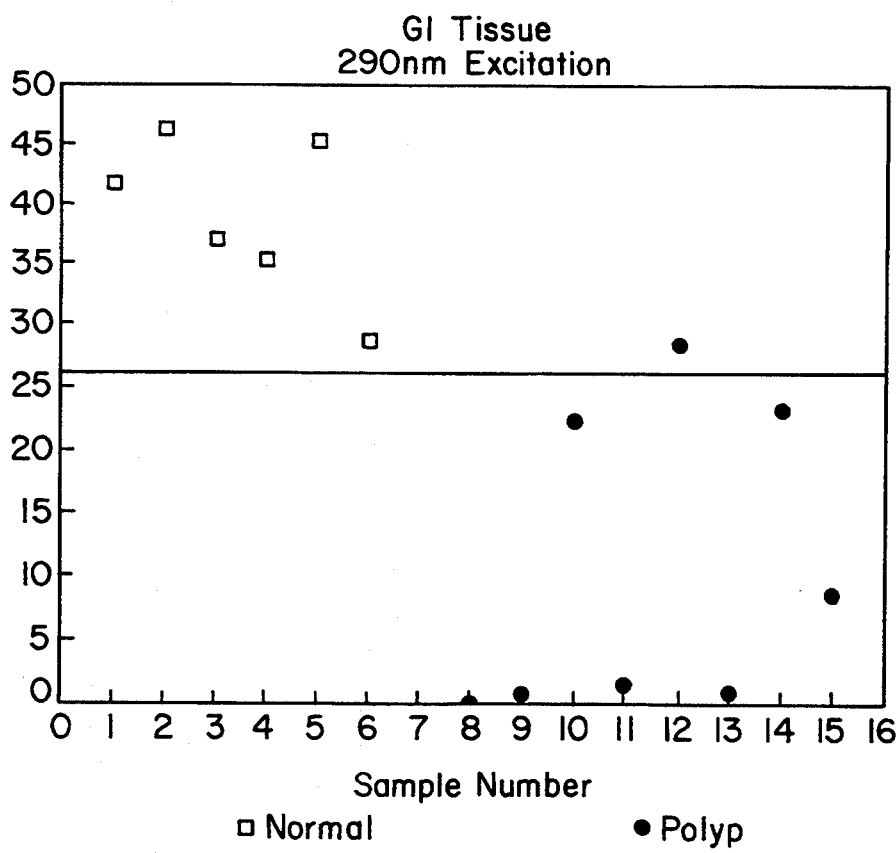
Figure 3C:
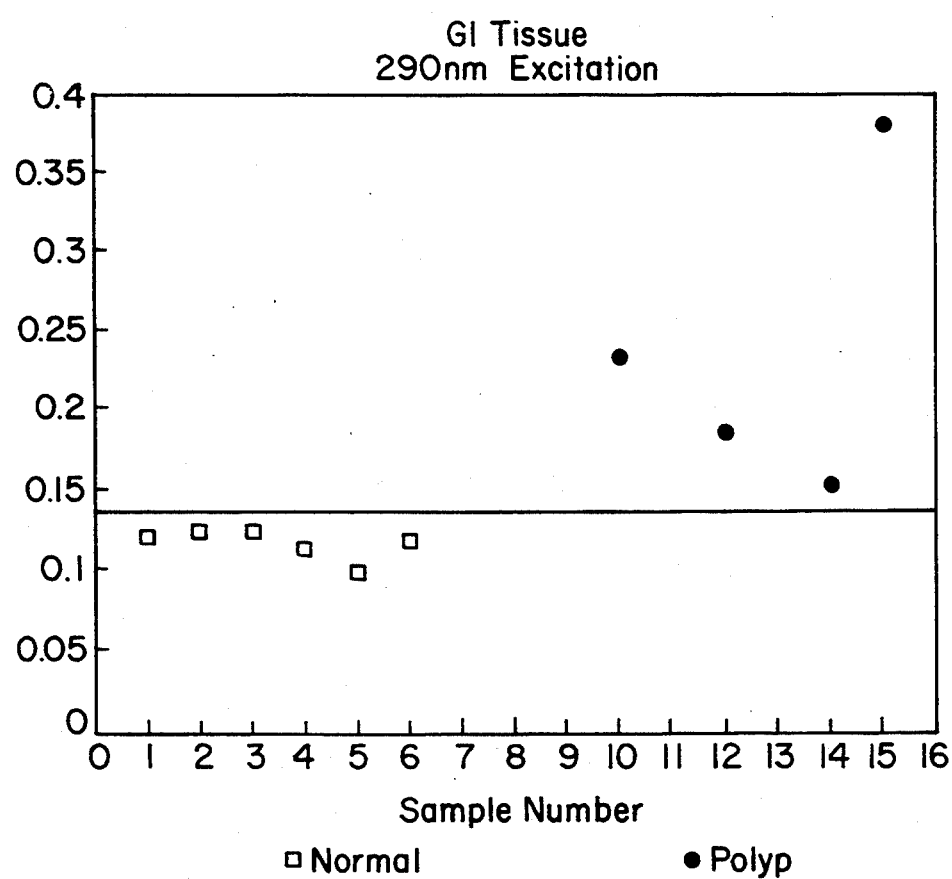
Figure 3D:
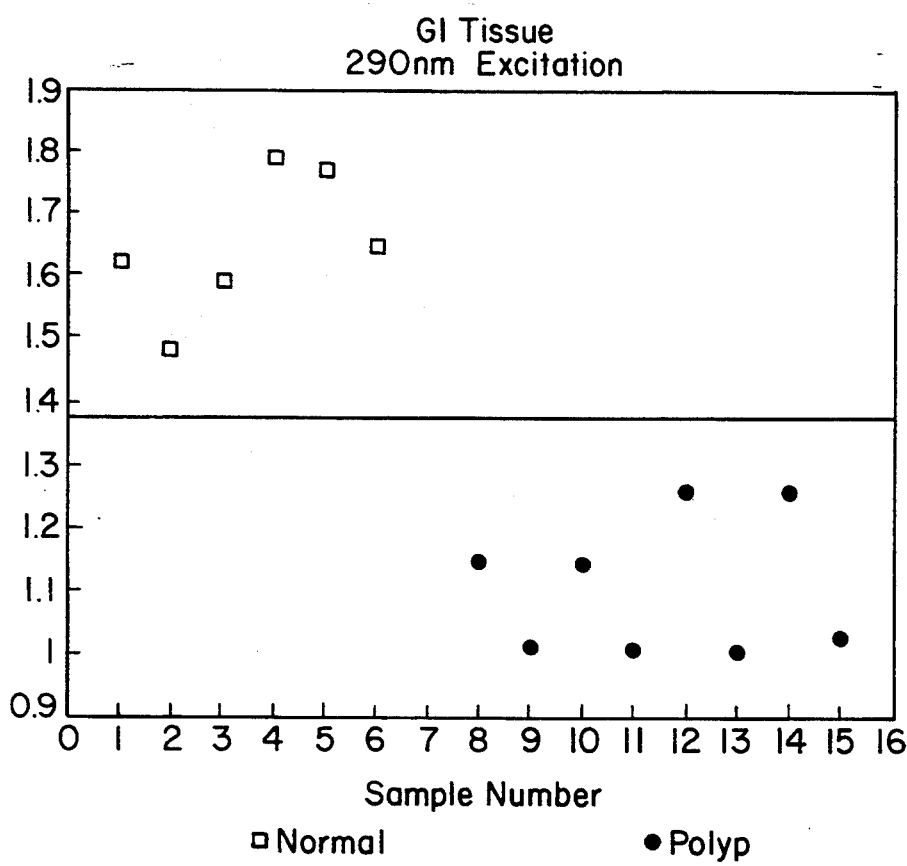
Figure 3E:
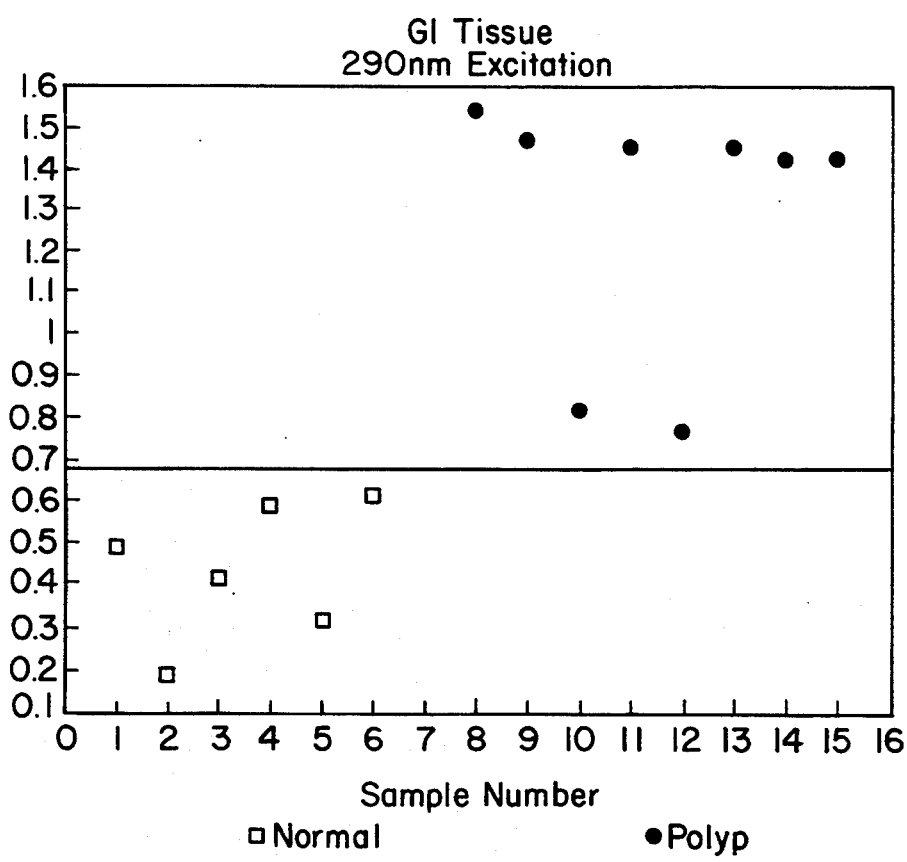

FIGS. 3(a) and 3(b) show that the ratios 335/365 and 335/440 can be used to diagnose tissues as normal or polyp correctly in 94% of the cases studied. 100% accuracy is achieved with the ratios 440/390, 415/425 and 440/457 as indicated in FIGS. 3(c–e). In particular, the ratio 415/425 indicates little variation in its value for samples of a given tissue type and there is a large separation between the average values of normal and polyps tissues.

A complete separation is achieved although only about half of the polyp spectra showed these characteristic differences presented in FIG. 2. There are differences between the spectra of normal and polyp tissues which allow differentiation of tissue type in all cases.

Figure 4A:
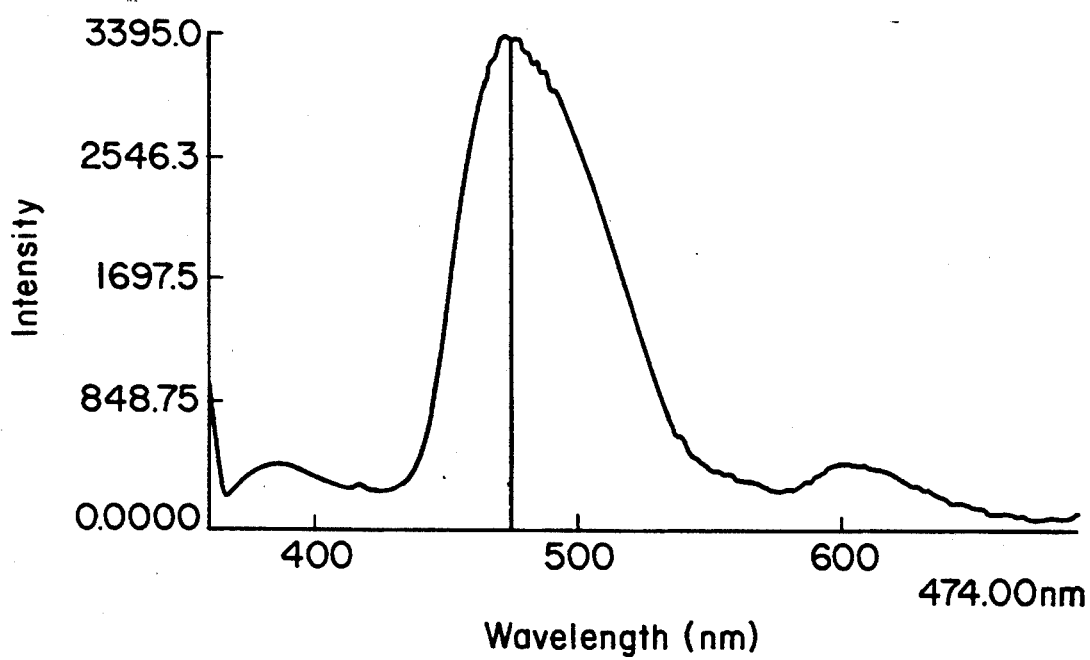
FIG. 4 illustrates emission spectra of (a) normal and (b) polyp tissues. Excitation wavelength was 350 nm.
Figure 4B:
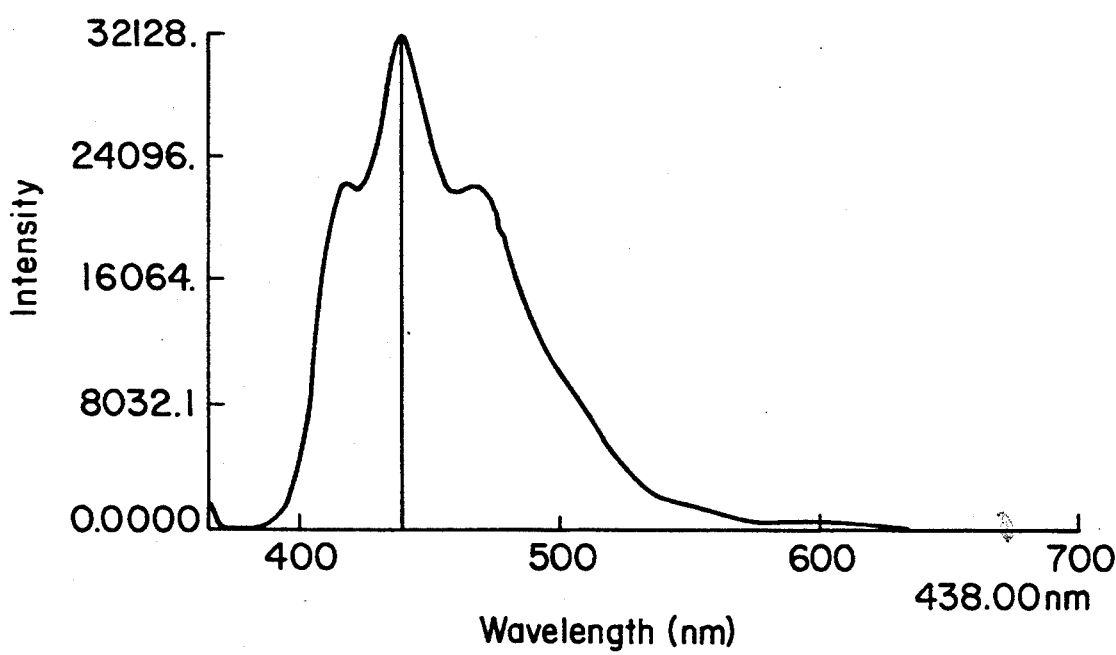
Figure 5A:
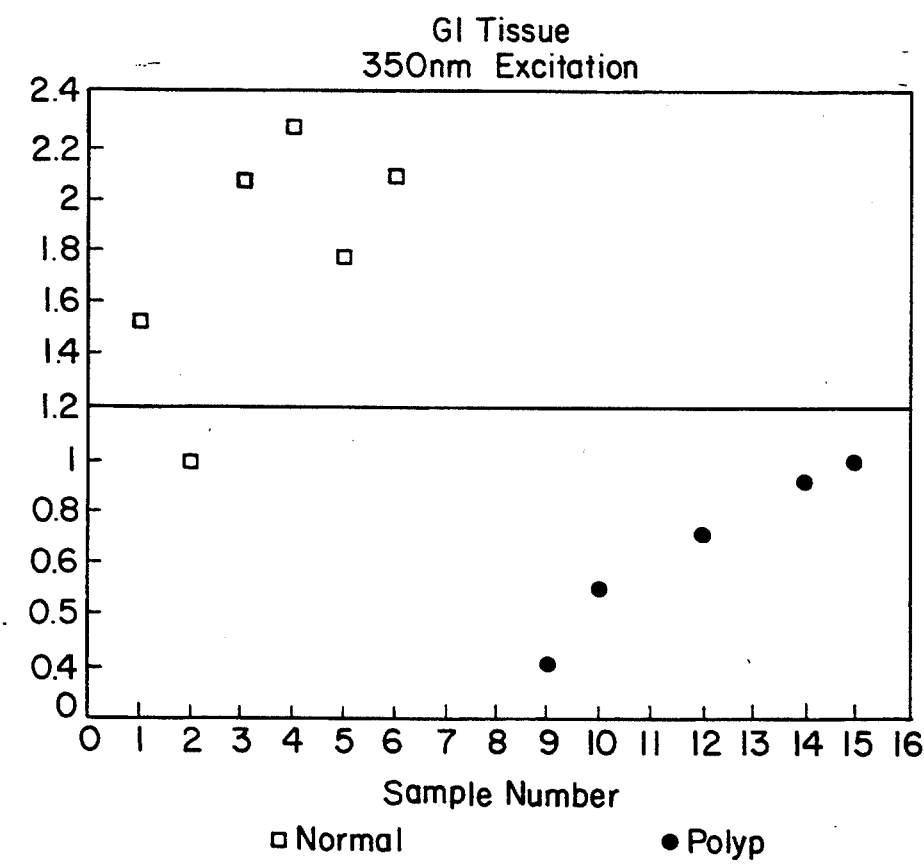
FIG. 5 shows values of intensity ratios at (a) 387/365, (b) 387/427, (c) 415/425, (d) 440/457, (e) 495/440 and (f) 475/440. In each figure, the solid lines indicate a criterion for determining tissue type from the value of the ratio. In (a–c), 91% accuracy is achieved with this criterion; in (d–f), the accuracy is 100%.
Figure 5B:
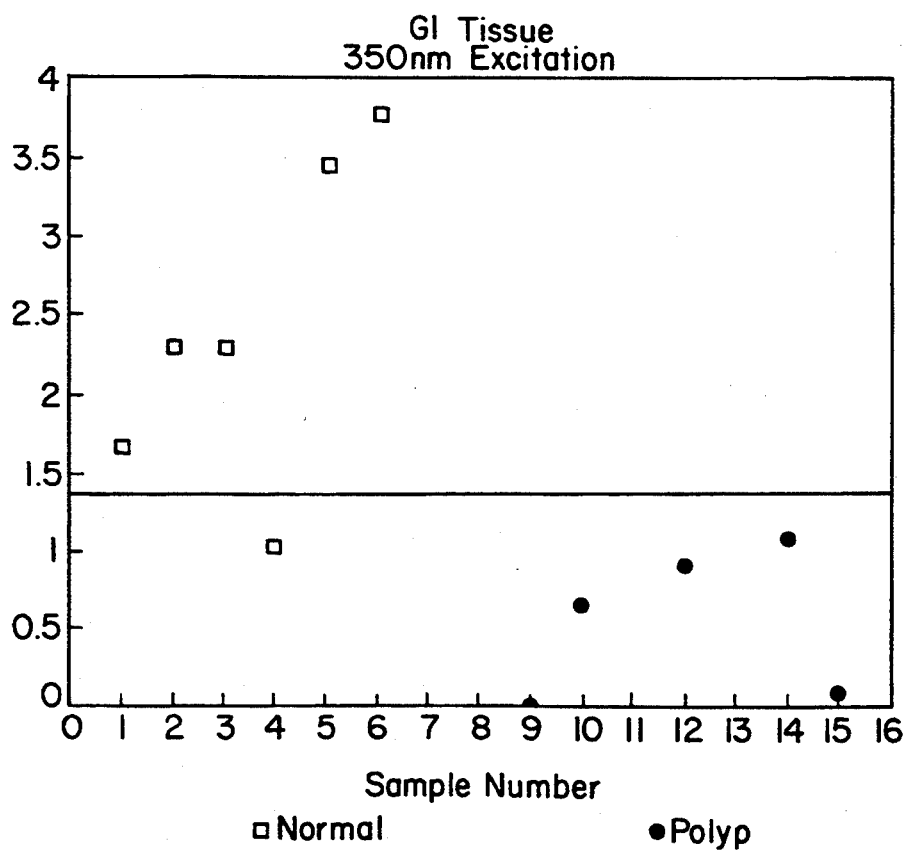
Figure 5C:
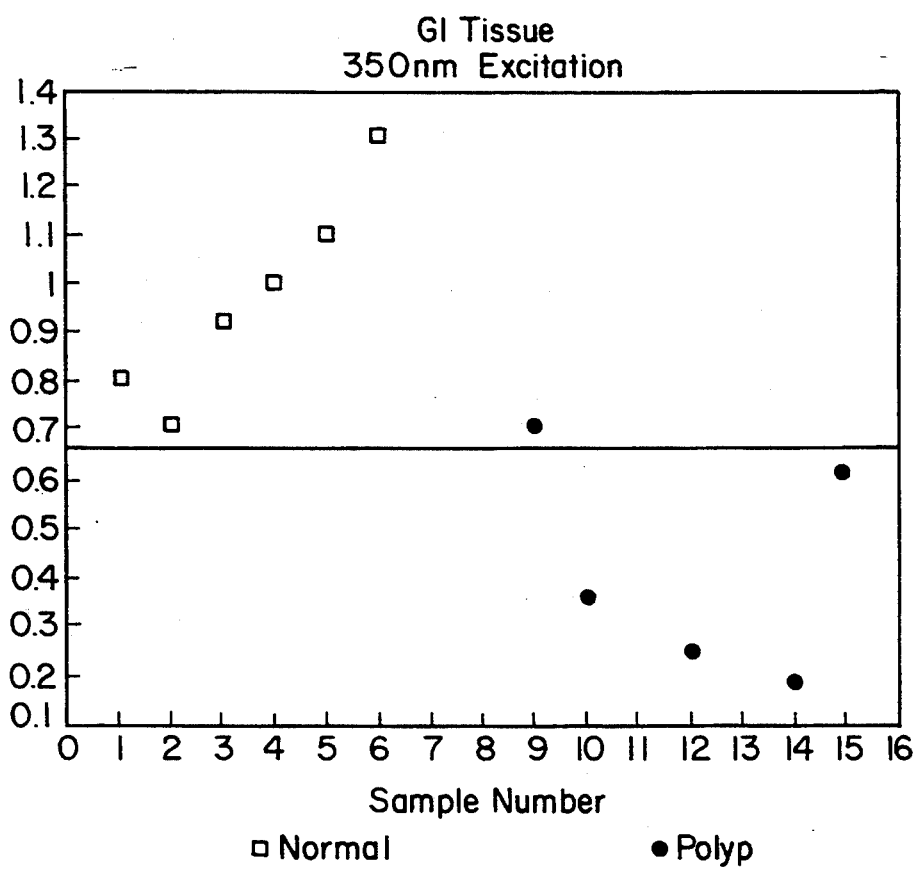
Figure 5D:
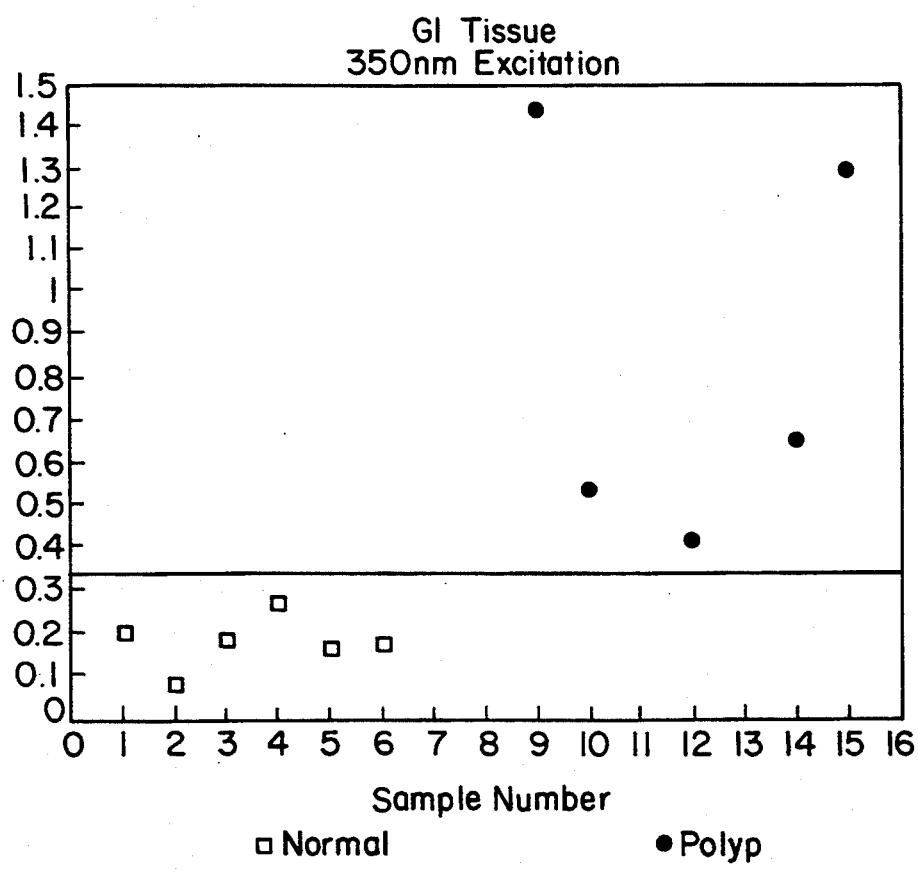
Figure 5E:
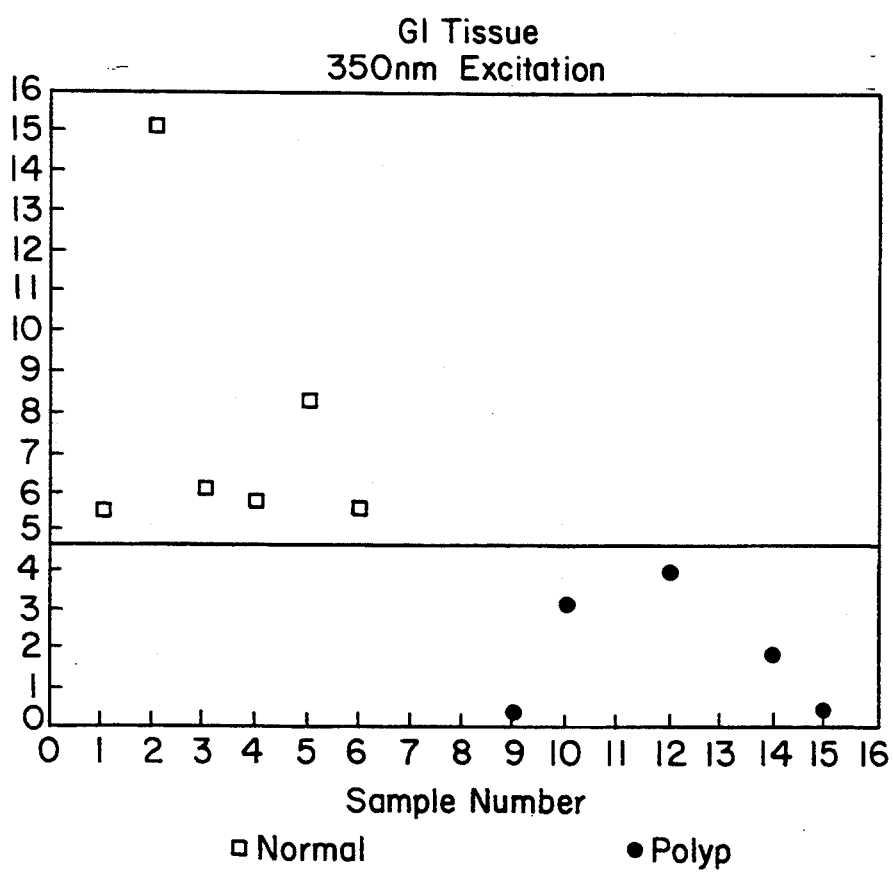
Figure 5F:
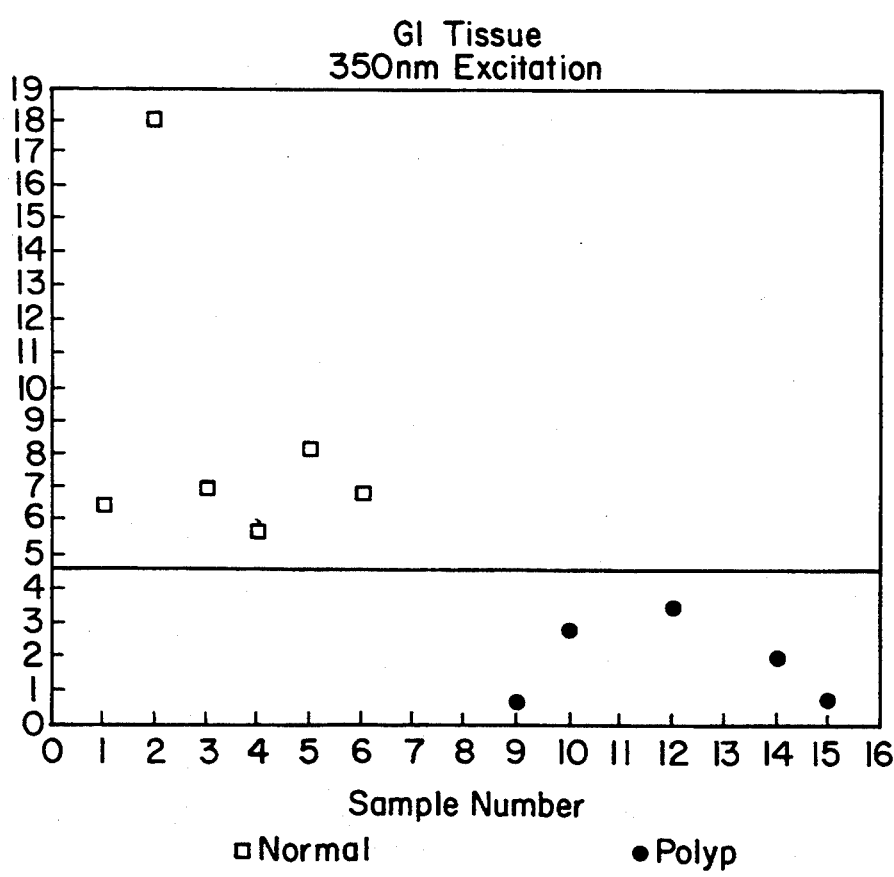

FIG. 4(a) shows fluorescence emission spectrum characteristic of normal tissue. FIG. 4(b) shows a spectrum characteristic of polyp tissues. Other polyp spectra were similar to normal tissue spectra and polyp tissues respectively with 350 nm excitation. The normal spectrum exhibits a peak at 387 nm, and a peak at 470 nm. Subsequent maxima in this peak are created by reabsorption of hemoglobin, and are present at 540 and 580 nm or 560 nm depending on whether the hemoglobin was in the oxy-or deoxy-state. The polyp spectrum on the other hand shows a three peak structure with maxima at 415, 440 and 460 nm.

To correlate features of these fluorescence spectra to tissue type in a quantitative way for all samples, we defined several empirically defined parameters, ratios of fluorescence intensities at the following wavelengths: 387/365, 387/427, 415/425, 440/457, 495/440 and 475/440. Although many combinations of wavelengths were tried, these were also found to indicate separation of samples according to sample type. The value of these ratios versus tissue type are shown in FIG. 5(a–f). The following table lists the average values and standard deviations for each ratio vs. tissue type.

TABLE 2

| Ratio | Average Value (± std. dev.) for: Normal | Polyp |
|---|---|---|
| 387/365 | 1.80 ± 0.43 | 0.68 ± 0.28 |
| 387/427 | 2.37 ± 0.96 | 0.53 ± 0.42 |
| 415/425 | 0.98 ± 0.19 | 0.42 ± 0.20 |
| 440/457 | 0.18 ± 0.05 | 0.87 ± 0.42 |
| 495/440 | 7.76 ± 3.43 | 2.01 ± 1.45 |
| 475/440 | 8.76 ± 4.22 | 1.94 ± 1.12 |

FIGS. 5(a–c) show that the first three empirically defined ratios can be used to diagnose tissue type correctly in 91% of all cases studied. FIGS. 5(d–f) illustrate that 100% accuracy can be achieved using the ratios 440/457, 495/440 and 475/440. With the last ratio there is a large separation between the value of the ratio for all normal and polyp samples.

Figure 6A:
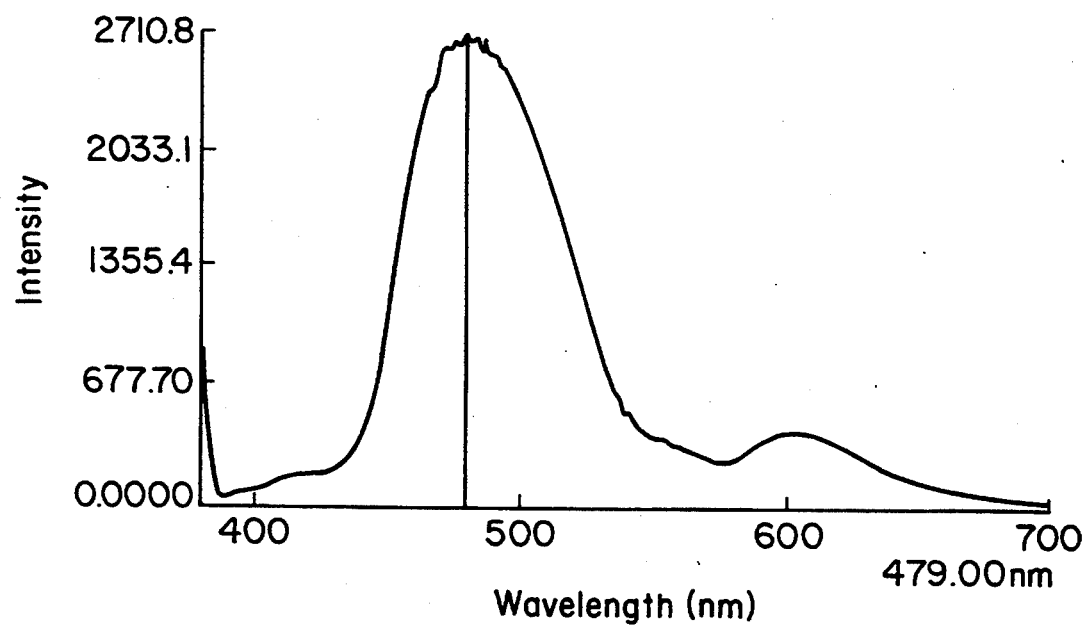
FIG. 6: Typical emission spectra of (a) normal and (b) polyp tissues. Excitation wavelength was 370 nm.
Figure 6B:
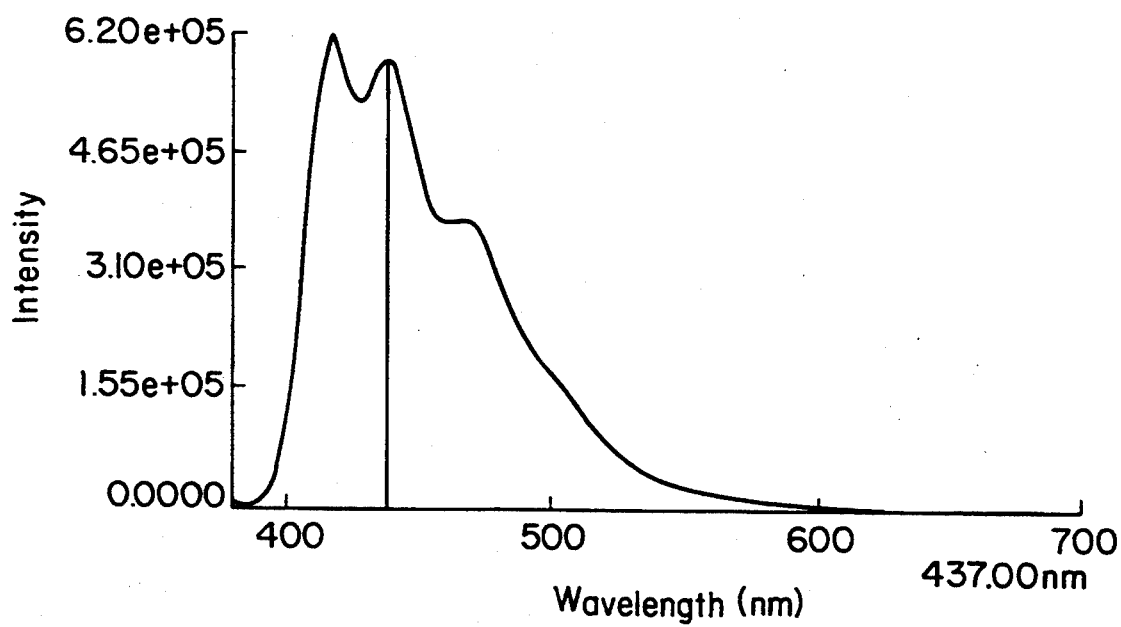

FIG. 6(a) shows a typical emission spectrum of normal tissue with 370 nm excitation. Certain polyp samples showed emission spectra similar to this. FIG. 6(b) illustrates the emission spectrum characteristic for polyp samples. Normal samples showed a small peak at 420 and a large peak at 480 nm with subsidiary maxima produced by hemoglobin reabsorption. Polyp samples again showed the three peaked structure at 415, 440 and 460 nm.

Figure 7A:
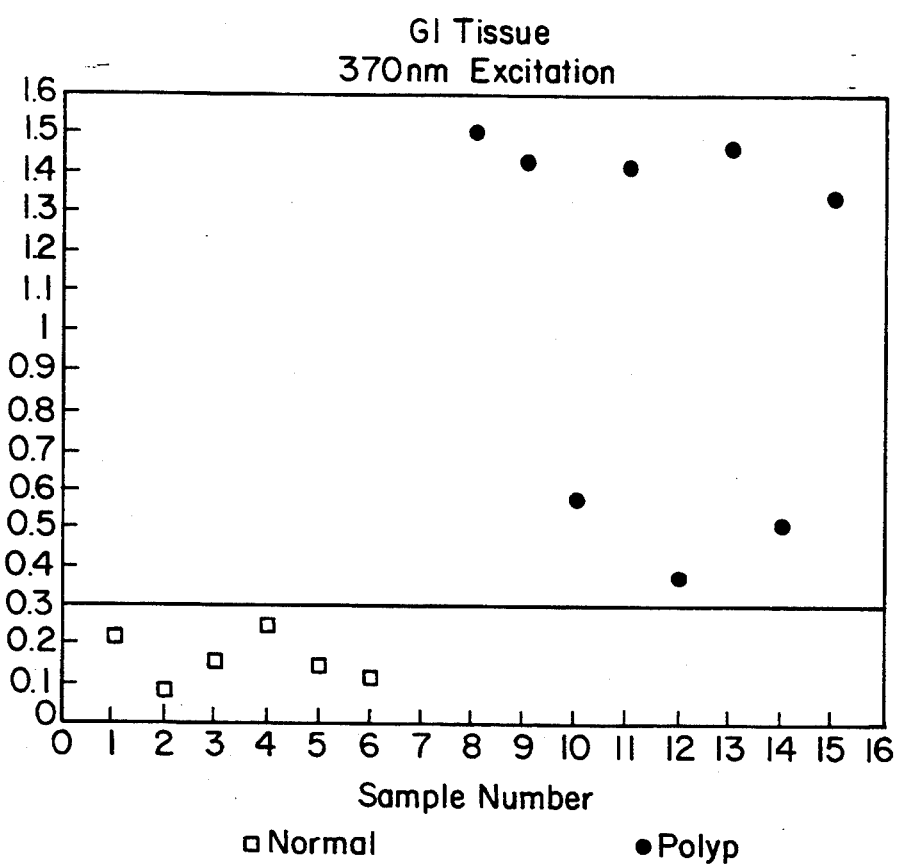
FIG. 7: Values of intensity ratios at (a) 440/457, (b) 480/440 and (c) 440/390. In each figure, the solid lines indicate a criterion for determining tissue type from the value of the ratio: In each case, 100% accuracy is achieved.
Figure 7B:
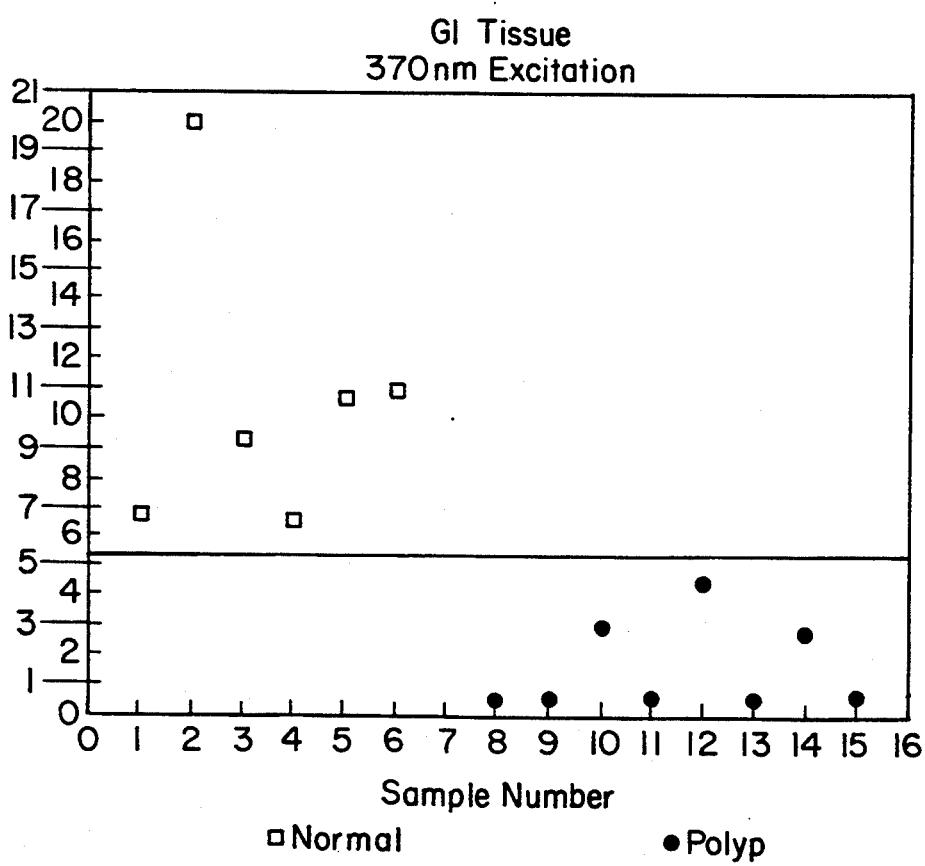
Figure 7C:
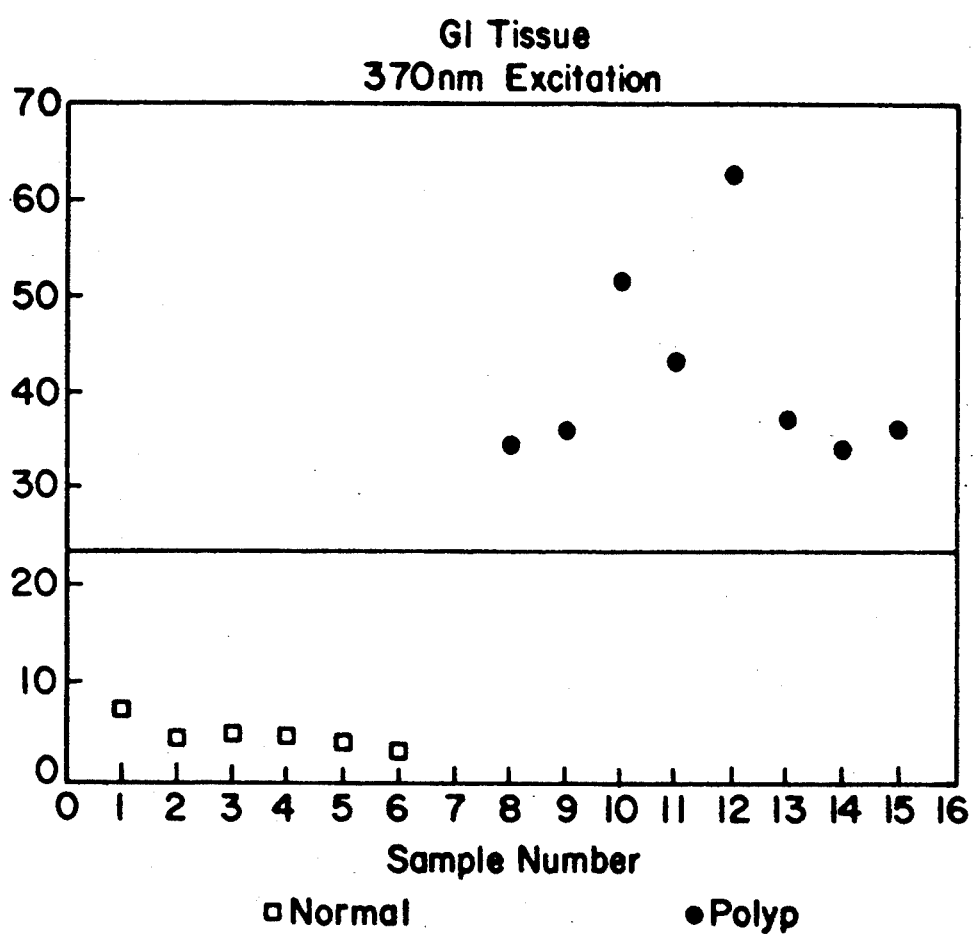

To correlate features of these fluorescence spectra to tissue type in a quantitative way for all samples, we defined several empirical algorithms, ratios of fluorescence intensities at the following wavelengths: 440/457, 480/440 and 440/390. Although many combinations of wavelengths were tried, these were found to indicate separation of samples according to sample type. The value of these ratios versus tissue type are shown in FIGS. 7(a-c). The following table lists the average values and standard deviations for each ratio vs. tissue type.

TABLE 3

| | Average Value (± std. dev.) for: | |
|---|---|---|
| Ratio | Normal | Polyp |
| 440/457 | 0.16 ± 0.06 | 1.09 ± 0.46 |
| 480/440 | 10.71 ± 4.47 | 1.62 ± 1.44 |
| 440/390 | 4.57 ± 1.31 | 41.98 ± 9.59 |

FIGS. 7(a-c) illustrate that each of these three ratios was able to achieve separation of tissue by type accurately in 100% of cases studied. In particular, the ratio 440/390 provided the larges.t degree of separation between normal and polyp tissues.

For the analysis of the second and-third groups of tissue, the results of which are illustrated in FIGS. 8-27, the following methods were employed. An average normal spectrum $F_N(\lambda)$ and adenomatous tissue spectrum $F_{Ad}(\lambda)$ were calculated from this normalized data. In addition, standard deviation spectra were calculated for the normal $\alpha_N(\lambda)$ and adenomatous $\alpha_{Ad}(\lambda)$ tissue spectra. An average difference spectrum was calculated, as $F_{Ad}(\lambda) - F_N(\lambda)$, to determine differences in the fluorescence lineshapes of normal and adenomatous tissues. Finally, to determine emission wavelengths at which differences between normal and adenomatous tissues were most consistently different an average discriminant spectrum $D(\lambda)$ was calculated as:

$$D(\lambda) = \frac{F_{AD}(\lambda) - F_N(\lambda)}{\sigma_{Ad}^2(\lambda) + \sigma_N^2(\lambda)}$$

As the absolute value of $D(\lambda)$ increases, so does the statistical ability to discriminate between normal and adenomatous samples. Wavelengths corresponding to peaks in $D(\lambda)$ were used in constructing empirical methods to differentiate normal and adenomatous tissues based on their individual difference spectra, $F_{Ni}(\lambda) - F_N(\lambda)$ and $F_{Adi}(\lambda) - F_N(\lambda)$.

Figure 8A:
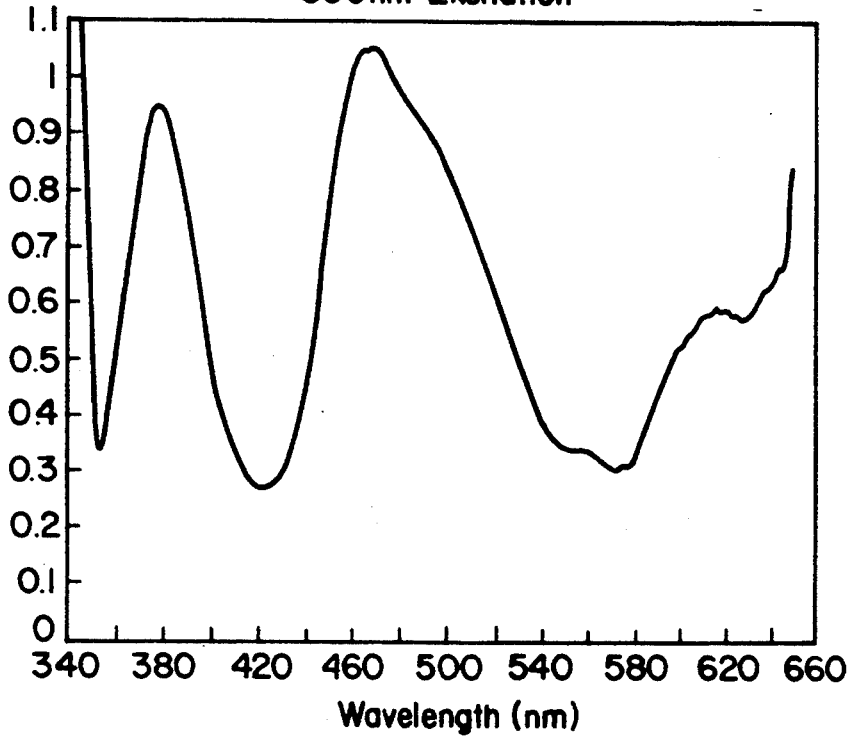
FIGS. 8a and 8b illustrate average normalized fluorescence spectra of normal and adenomatous tissues at 330 nm excitation.
Figure 8B:
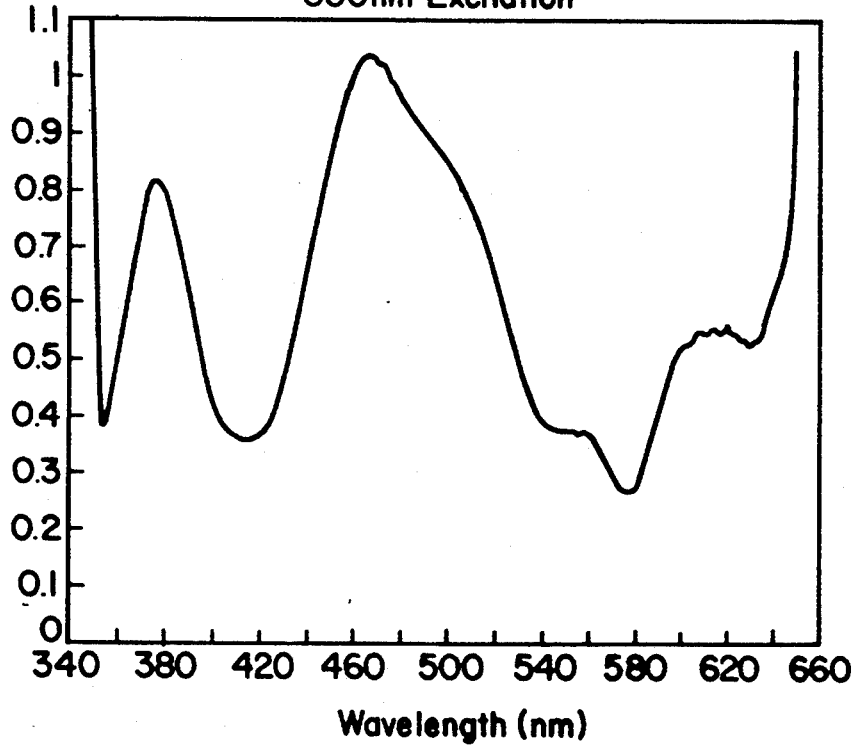
Figure 9A:
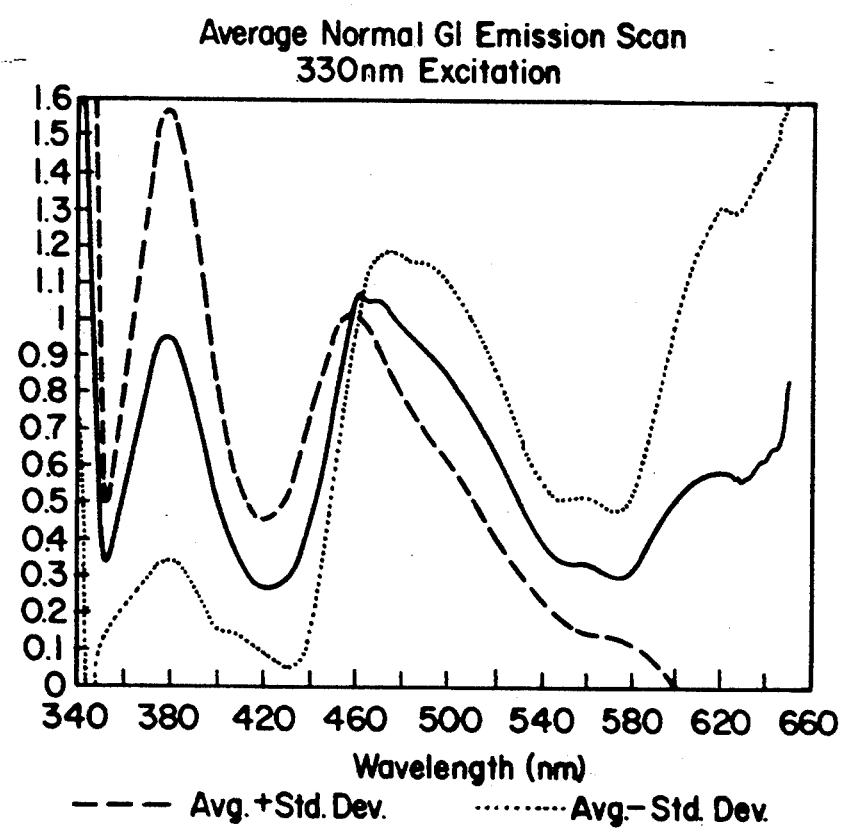
FIGS. 9a and 9b illustrate the spectra of FIGS. 8a and 8b, respectively, with positive and negative standard deviation spectra superimposed thereon.
Figure 9B:
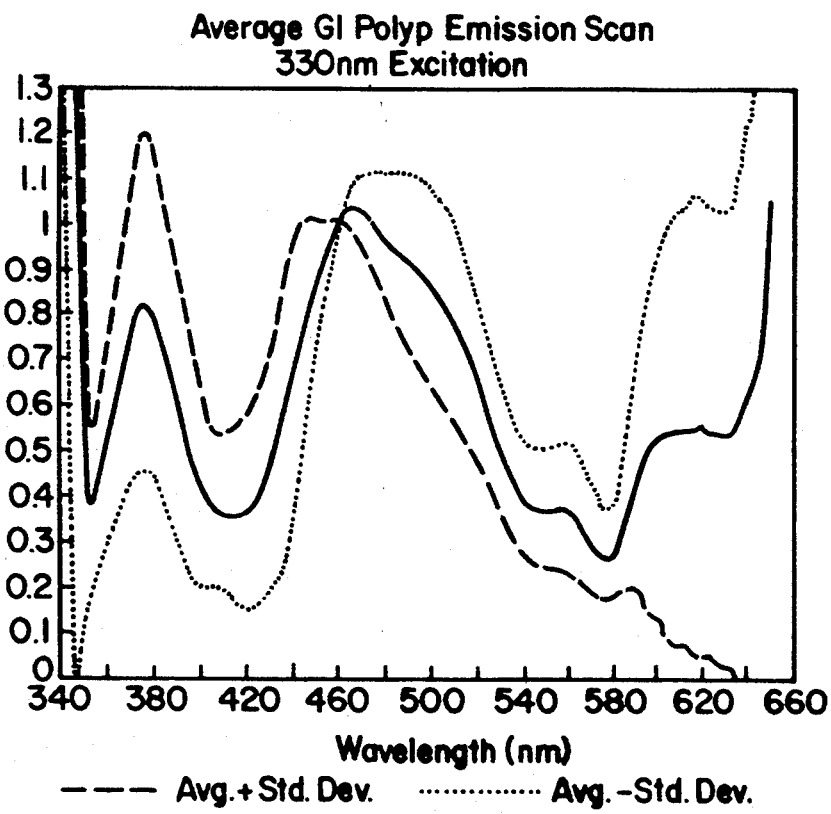

FIGS. 8(a) and (b) show average normalized fluorescence spectra of normal and adenomatous tissues at 330 nm excitation. For both tissues, fluorescence peaks are found at 380 and 460 nm. In addition, valleys in the fluorescence spectra due to hemoglobin reabsorption can be observed at 420, 540 and 580 nm. FIGS. 9(a) and (b) show these same average spectra, but with average ± standard deviation spectra superimposed. This illustrates that the most variable regions of the spectrum are near the 380 and 600 nm peaks.

Figure 10:
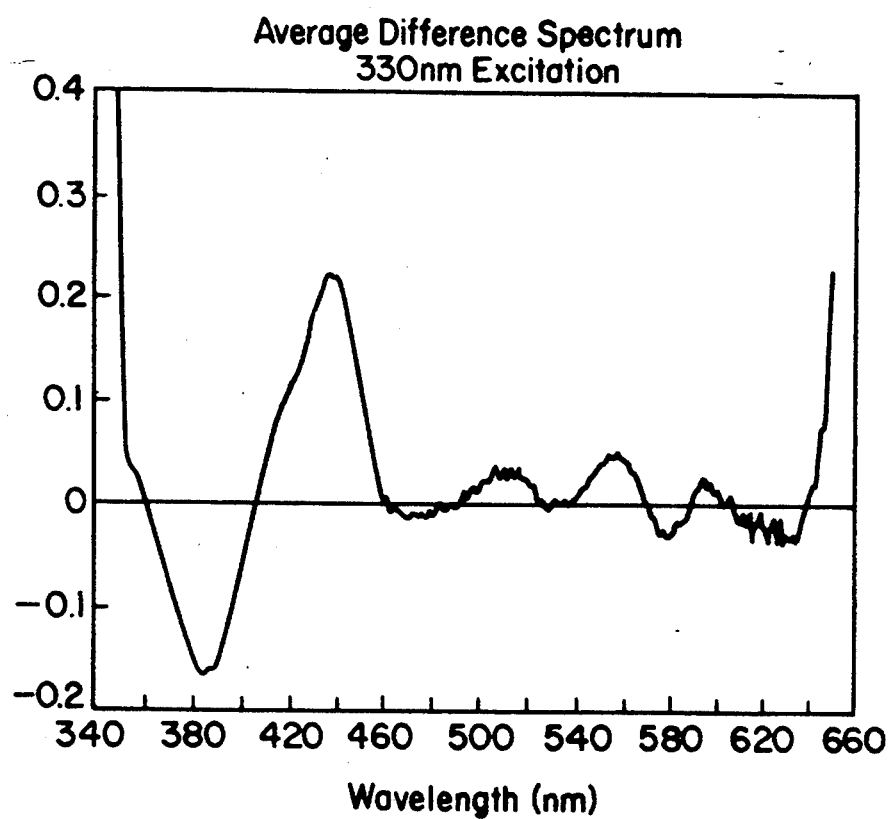
FIG. 10 illustrates an average difference spectrum at 330 nm excitation.

To better illustrate the differences in normal and adenomatous tissue fluorescence spectra at 330 nm excitation, FIG. 10 shows the average difference spectrum. Two major differences are apparent. On average, normal tissue displays relatively more intense fluorescence at 380 nm, while adenomatous tissue exhibit relatively more intense fluorescence at 440 nm. In addition, smaller differences are present near 550 nm, with adenomatous tissues exhibiting relatively more fluorescence in this region of the spectrum.

Figure 11:
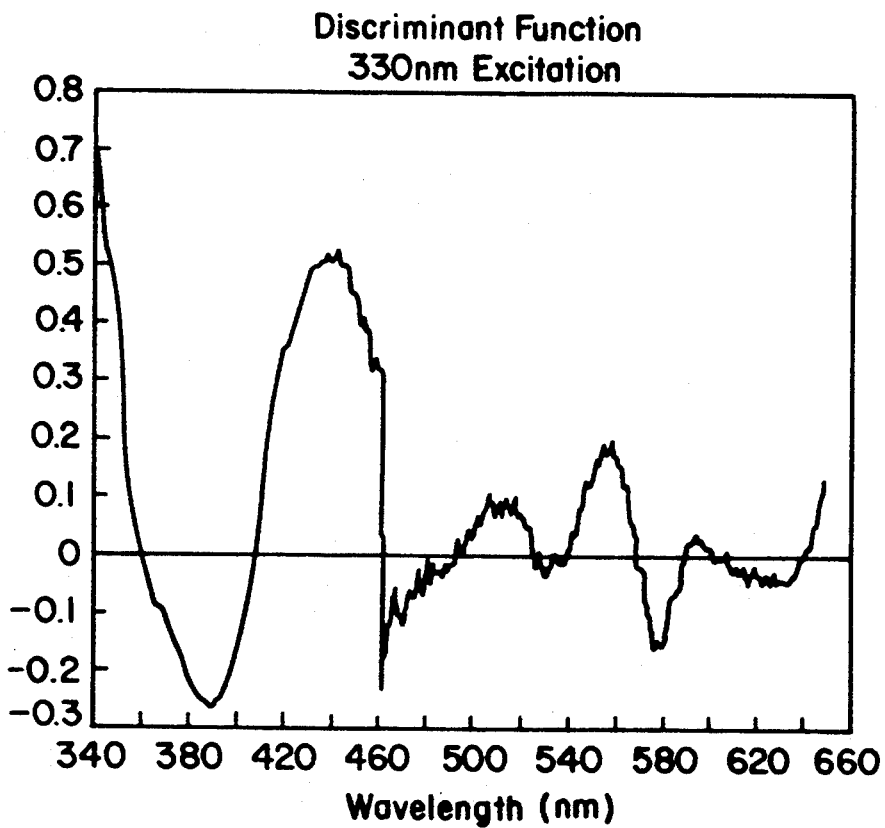
FIG. 11 illustrates the discriminant function at the 330 nm excitation.

FIG. 11 illustrates the discriminant function, $D(\lambda)$, at this excitation wavelength. This Figure shows B the same characteristic differences as the average difference spectrum; however, it shows that the most statistically consistent difference is that at 440 nm. The differences at 380 and 550 nm are approximately equally consistent. The peaks of $D(\lambda)$ are useful in defining empirical methods to differentiate the individual normal and adenomatous tissue spectra. The values of the relative fluorescence intensities at 384, 438 and 558 nm were determined for each individual difference spectrum $F_{Ni}(\lambda) - F_N(\lambda)$ and $F_{Adi}(\lambda) - F_N(\lambda)$.

Figure 12:
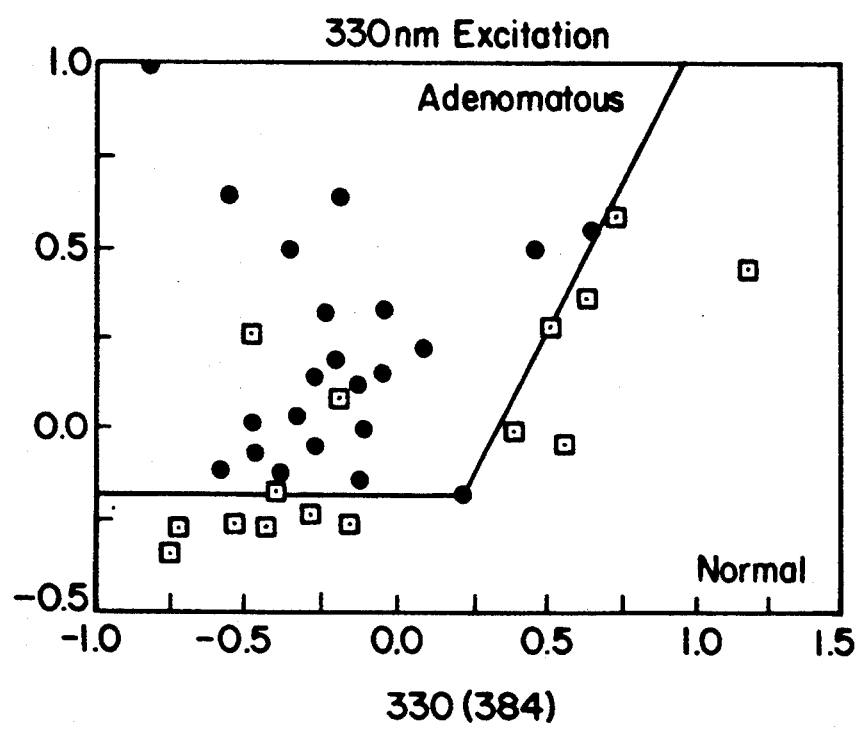
FIG. 12 graphically illustrates a combination diagnostic/algorithm based upon emission wavelengths at 438 and 384 nm.

Although none of these individual values is highly accurate as a diagnostic method, a combination of these values at 438 and 384 nm, as shown in FIG. 12, was found to be a useful. In this case, the method represented by the solid line correctly diagnoses 34 of the 38 samples.

Figure 13A:
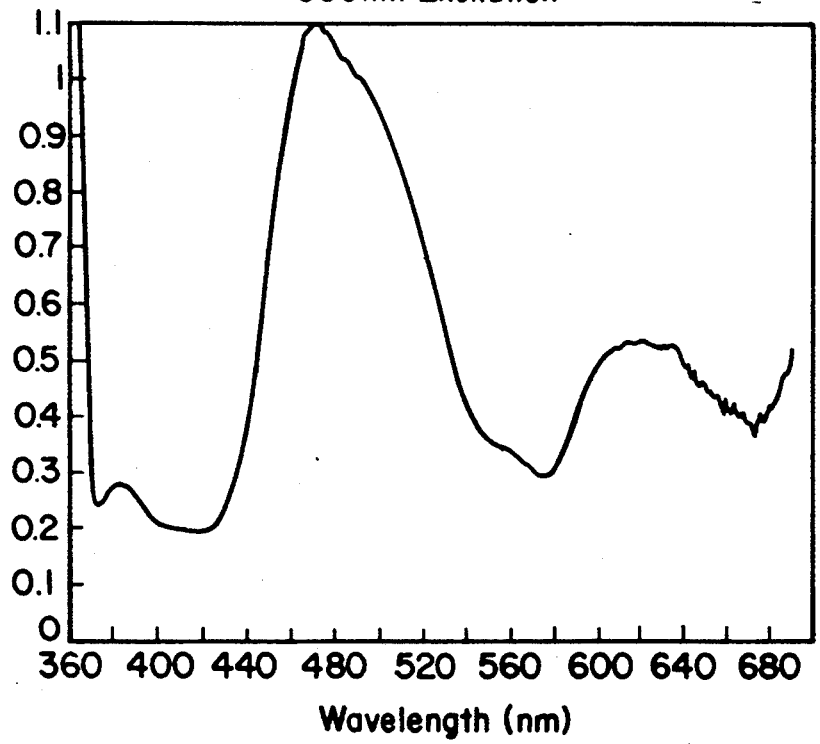
FIGS. 13a and 13b illustrate average fluorescence spectra at 350 nm excitation.
Figure 13B:
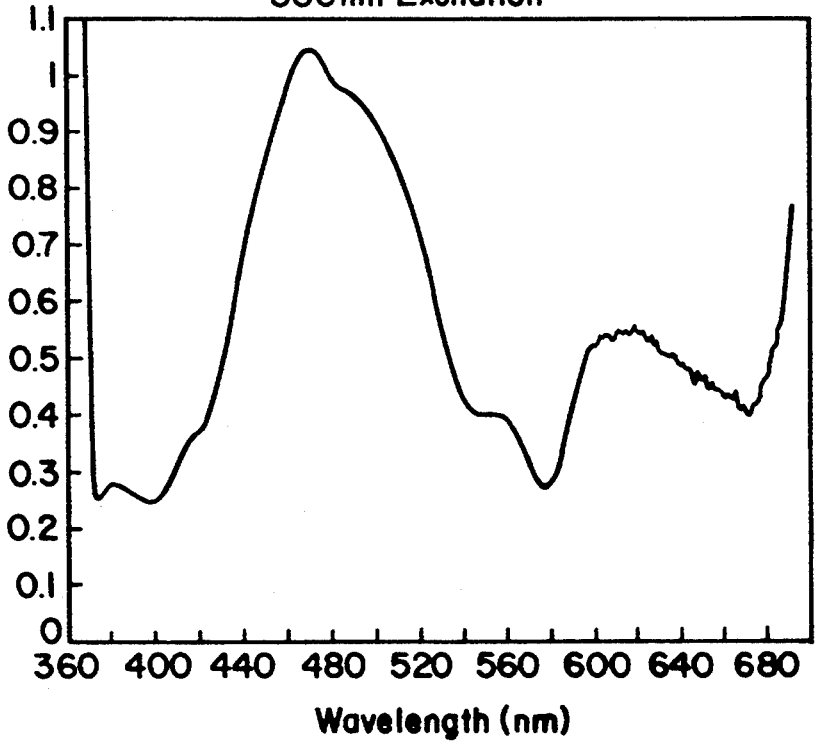
Figure 14A:
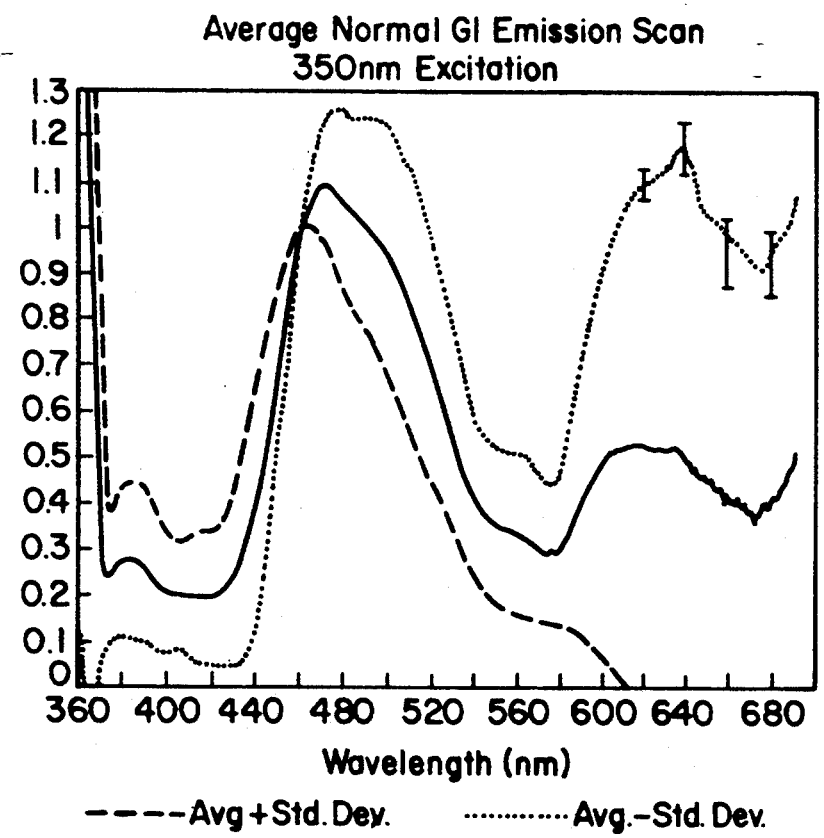
FIGS. 14a and 14b illustrate the spectra of FIGS. 13a and 13b, respectively, with positive and negative standard deviations imposed thereon.
Figure 14B:
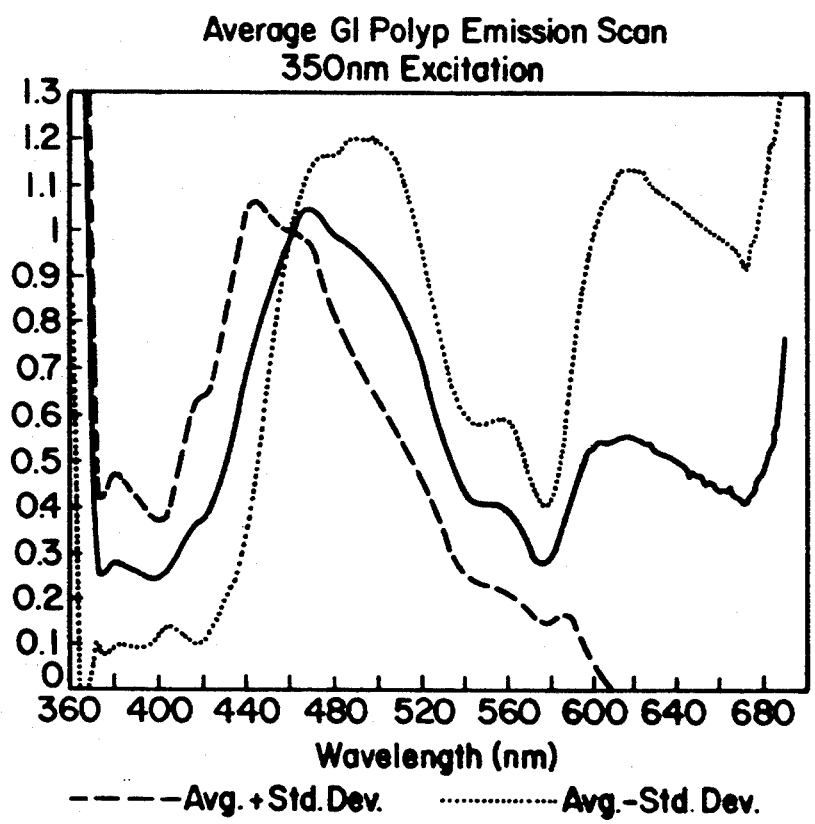

FIGS. 13(a) and (b) show average 350 nm fluorescence spectra of normal and adenomatous tissues. FIGS. 14(a) and (b) illustrate these same spectra ± standard deviations. Both tissue types exhibit peaks at 380 and 460 nm. In addition, hemoglobin absorption valleys are present at 420, 540 and 580 nm. FIG. 14 illustrates that the most variable region of the fluorescence spectrum is that at 600 nm for both types of tissue.

Figure 15:
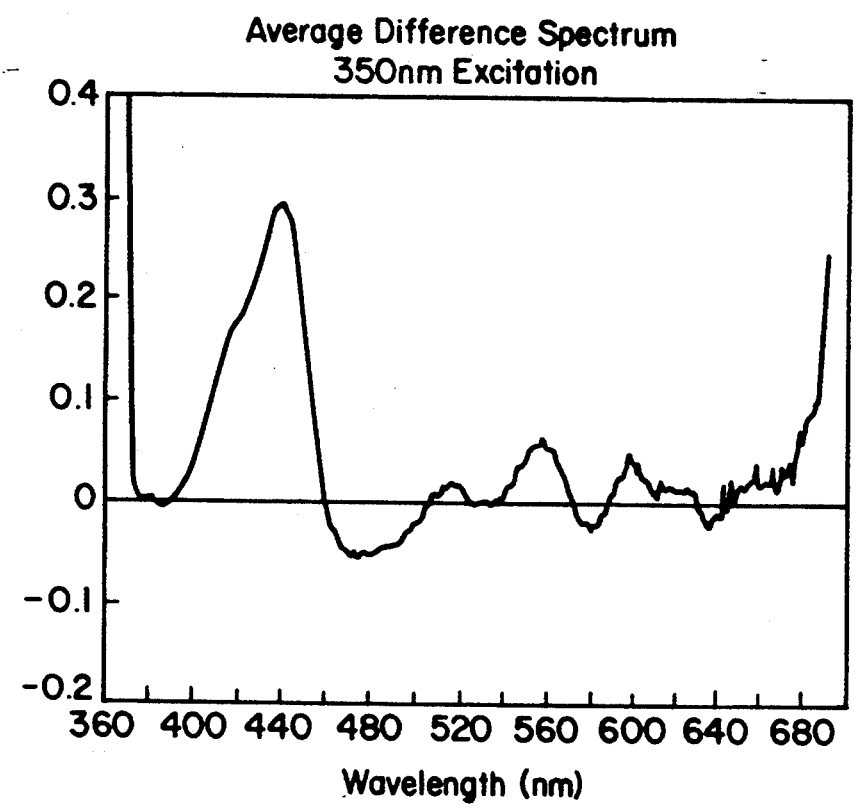
FIG. 15 illustrates an average difference spectrum at the 350 nm excitation.

FIG. 15 shows the average difference spectrum at 350 nm excitation. The major difference is the greater relative fluorescence intensity at 440 nm for adenomatous tissues. Again, a smaller difference is present at 550 nm, with adenomatous tissues having higher relative fluorescence intensity at this wavelength. Normal tissues, on the other hand, exhibit relatively more fluorescence at 470 nm.

Figure 16:
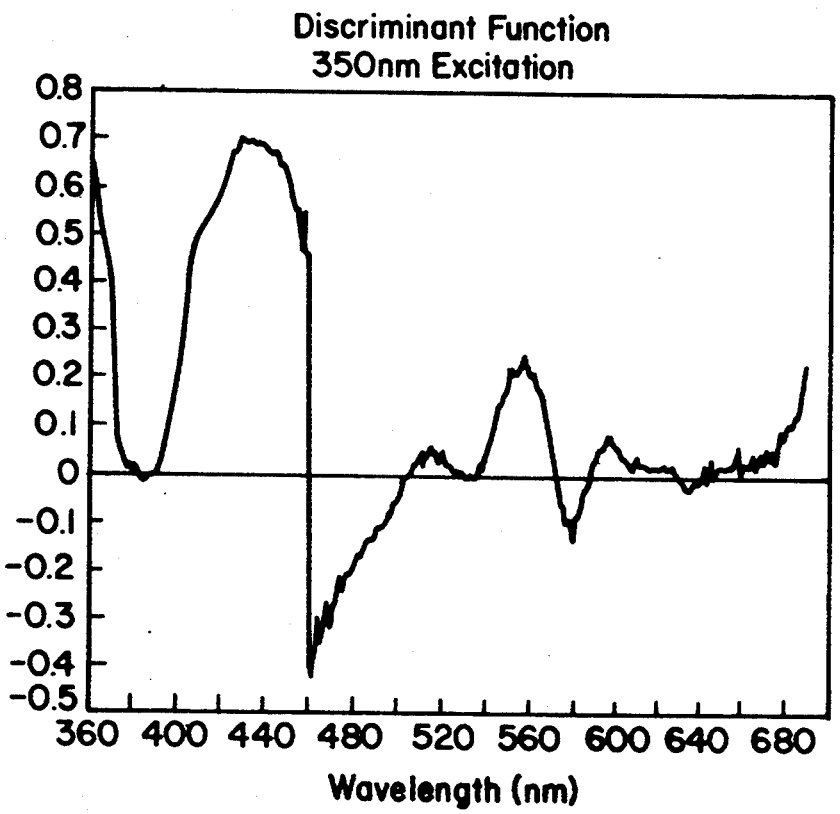
FIG. 16 illustrates the discriminant function at the 350 nm excitation.

$D(\lambda)$ is shown in FIG. 16, and is discriminant spectrum at the 350 nm excitation. The peaks of $D(\lambda)$ were used in choosing wavelengths to define empirical algorithms for differentiating normal and adenomatous tissues, based on their individual difference spectra $(F_{Ni}(\lambda) - F_N(\lambda)$ and $F_{Adi}(\lambda) - F_N(\lambda))$. Values of these difference spectra at 436, 476, and 558 nm were determined for each sample.

Figure 17:
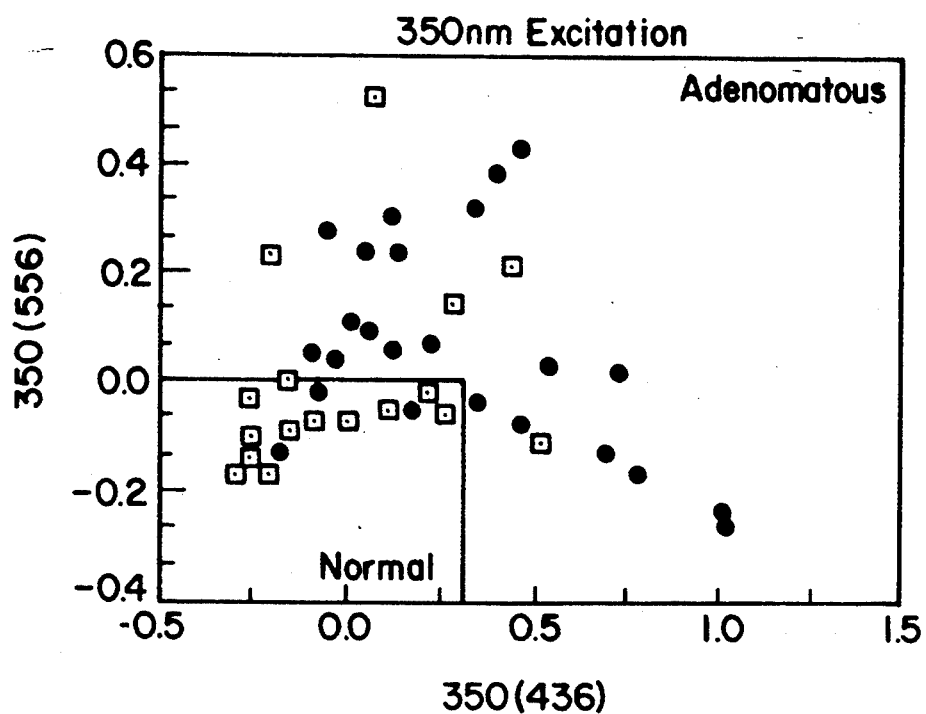
FIG. 17 graphically illustrates a combination diagnostic/algorithm based upon emission wavelengths at 436 and 556 nm.
Figure 18:
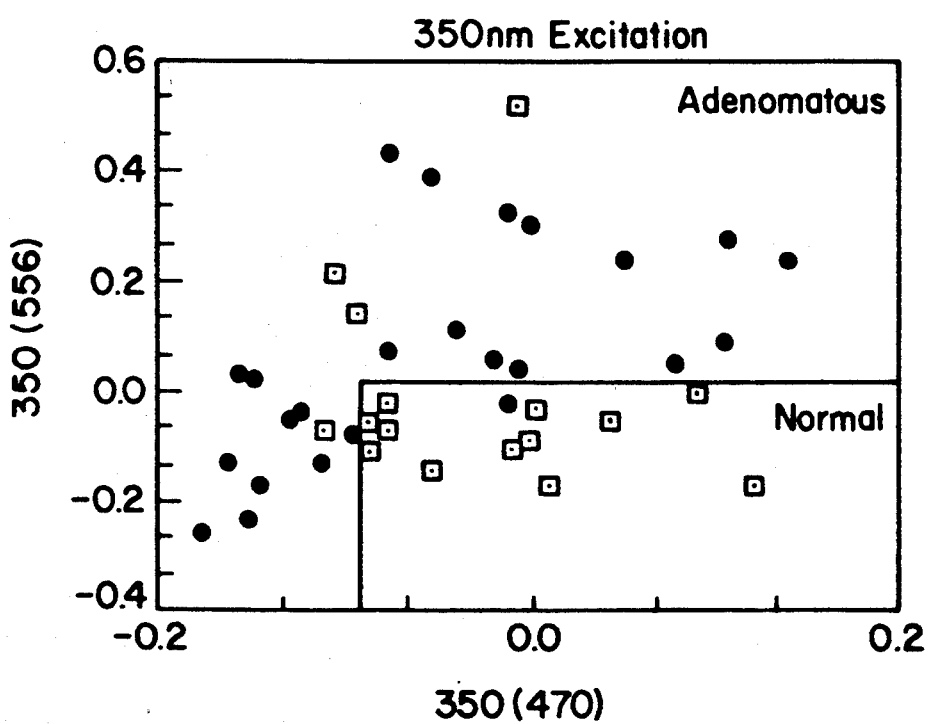
FIG. 18 graphically illustrates a combination diagnostic/algorithm based upon emission wavelengths at 470 and 556 nm.

Again, to achieve accurate identification of tissue type, it was necessary to consider a binary classification scheme with two of these values. FIGS. 17 and 18 show two such classification schemes. Using 436 and 556 nm, it is possible to correctly diagnose tissue type, with 470 and 556 nm the likelihood of a correct diagnosis is further increased.

Figure 19A:
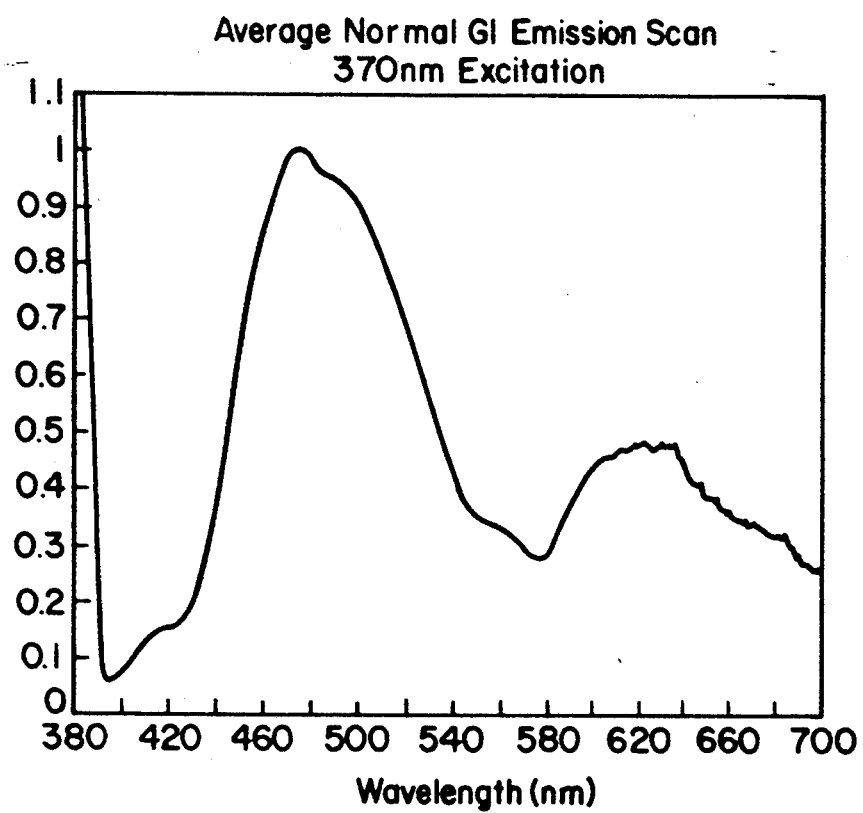
FIGS. 19a and 19b illustrate fluorescence spectra for normal and adenomatous tissue at 370 nm excitation.
Figure 19B:
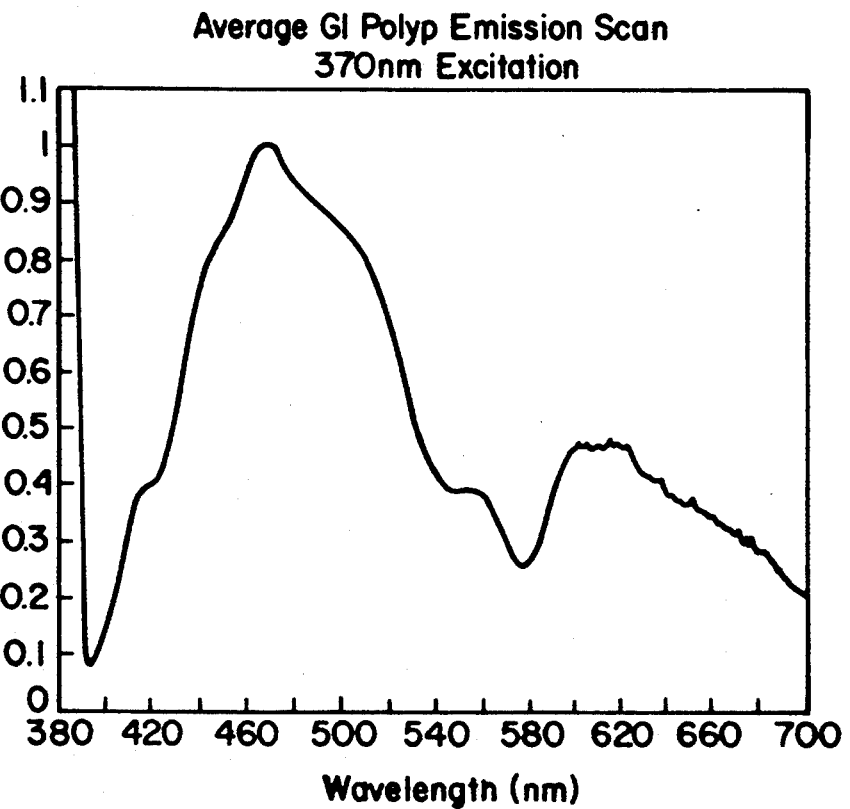
Figure 20A:
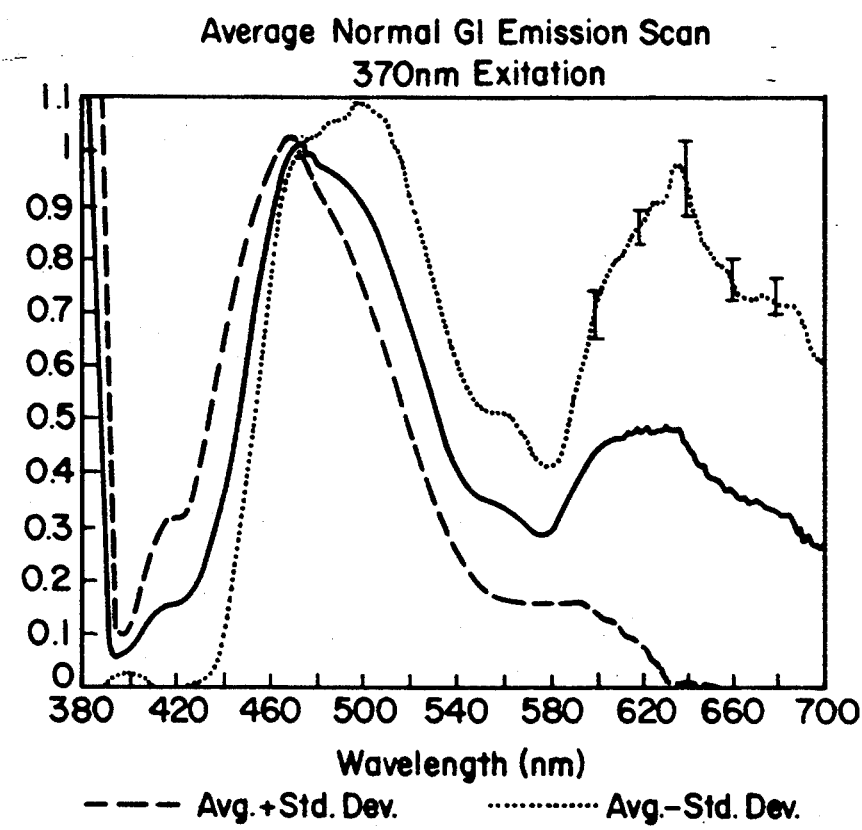
FIGS. 20a and 20b show the spectra of FIGS. 19a and 19b, respectively, with positive and negative standard deviations imposed thereon.
Figure 20B:
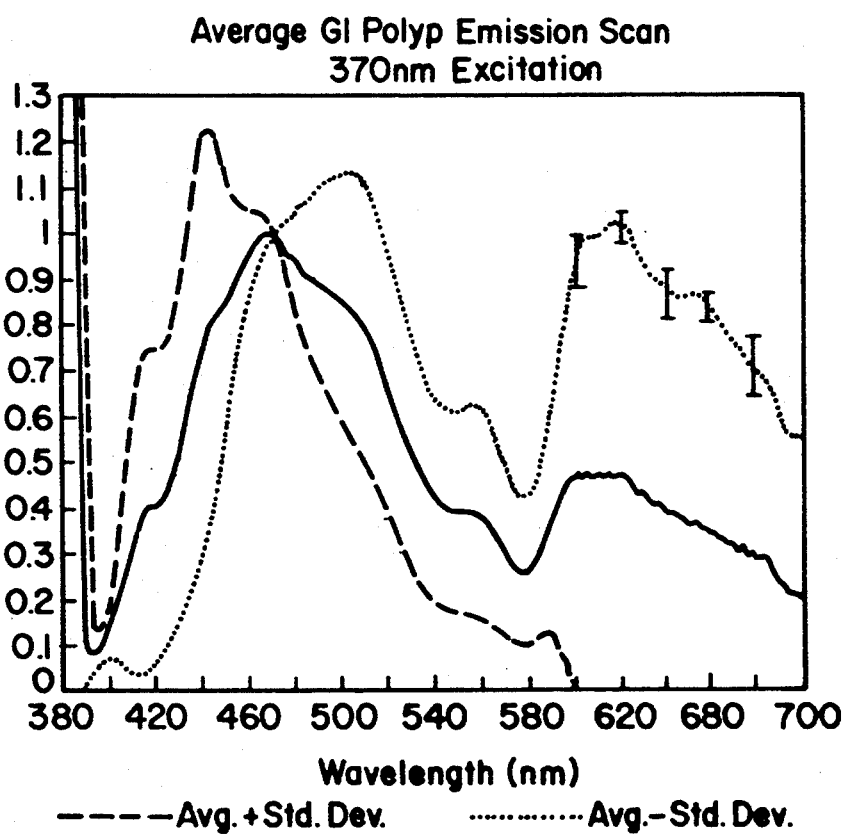

FIGS. 19(a) and (b) show average 370 nm excited fluorescence spectra for normal and adenomatous tissues. Both tissue types exhibit emission peaks at 470 nm, and hemoglobin absorption valleys at 420, 540 and 580 nm. However, an additional peak at 440 nm is now apparent in the fluorescence spectra of adenomatous tissues. FIGS. 20(a) and (b) which indicate average spectra±standard deviations, show that again the 600 nm emission region is most variable.

Figure 21:
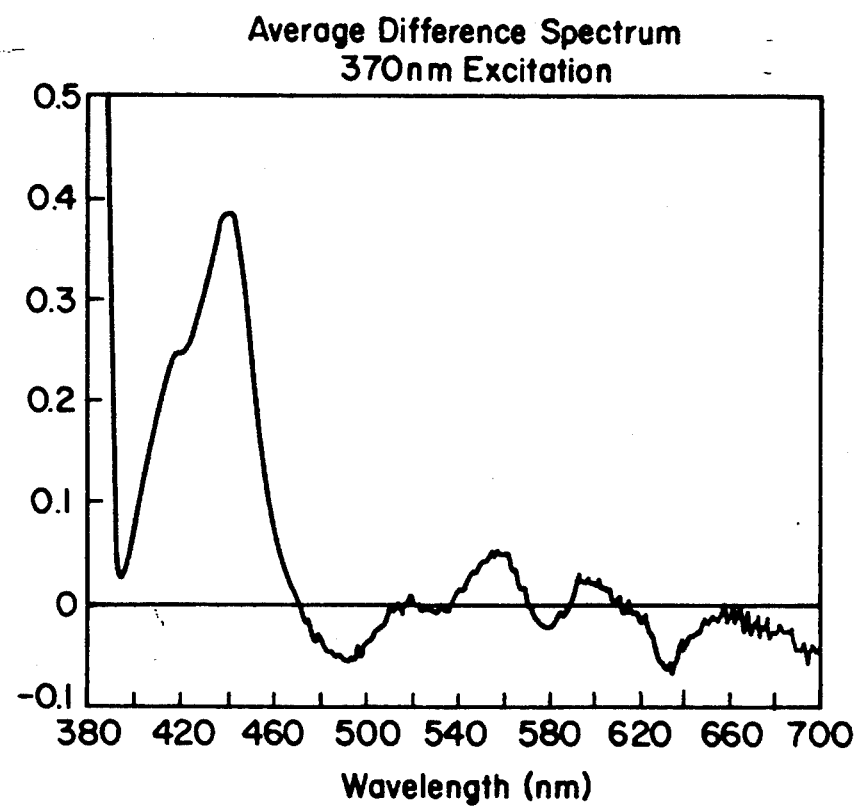
FIG. 21 illustrates an average difference spectrum at the 370 nm excitation.
Figure 22:
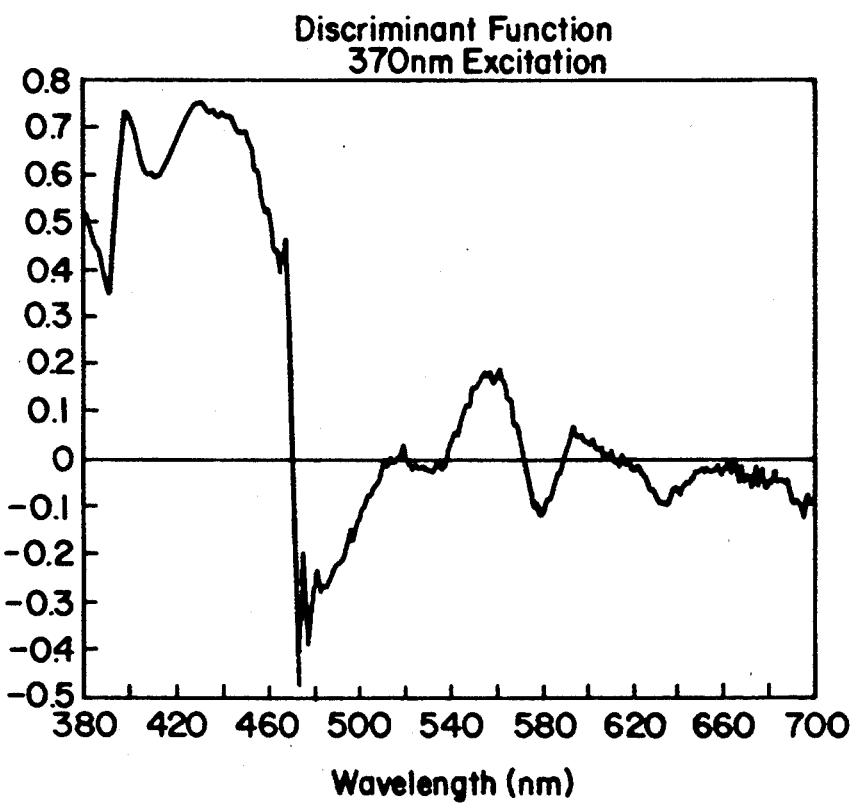
FIG. 22 illustrates the discriminant function at the 370 nm excitation.

FIG. 21 the average difference spectrum, indicates greater relative fluorescence intensity at 440 nm in adenomatous tissue. Again, small differences exist at 485 and 560 nm. The discriminant spectrum (FIG. 22), shows that the 440 nm peak is statistically most consistent. Again, the values of the individual difference spectra at each of these wavelengths was determined for each sample.

Figure 23:
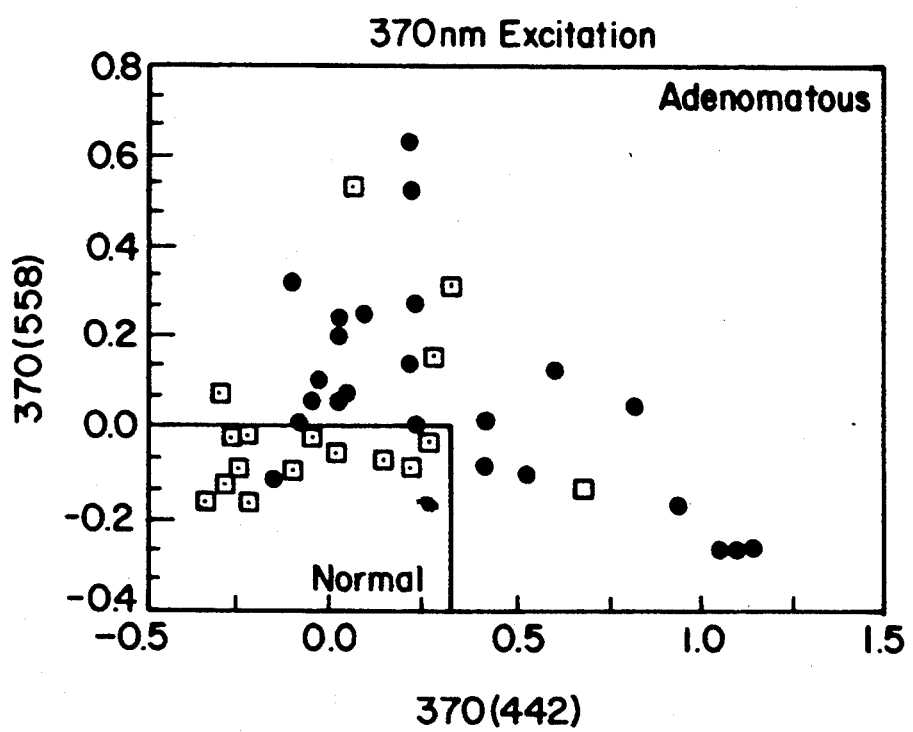
FIG. 23 graphically illustrates a combination diagnostic/algorithm based upon emission wavelengths at 442 and 558 nm.

Again, it was found that a combination of two of these values was required for an accurate empirical diagnostic algorithm. FIG. 23 shows one possible combination utilizing information at 442 and 558 nm.

Figure 24A:
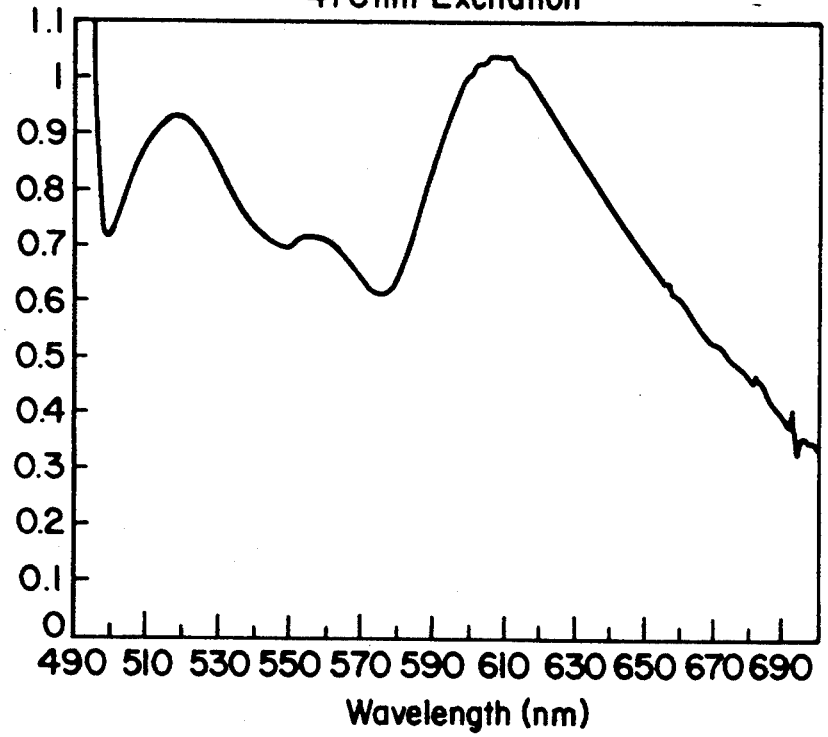
FIGS. 24a and 24b illustrate average normalized fluorescence spectra of normal and adenomatous tissues at 476 nm excitation.
Figure 24B:
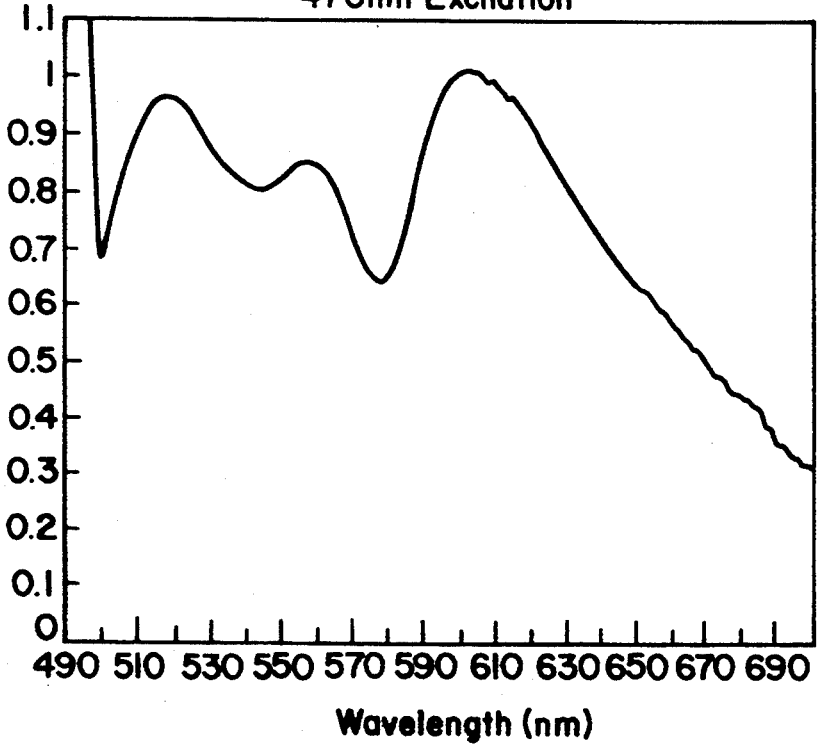
Figure 25A:
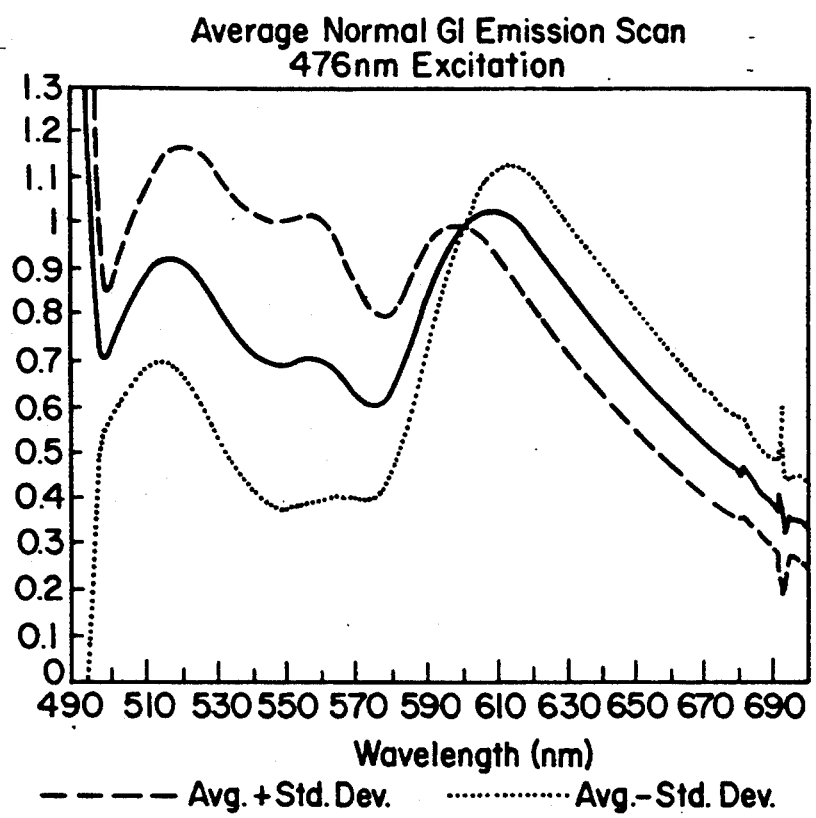
FIGS. 25a and 25b show the spectra of FIGS. 24a and 24b, respectively, with positive and negative standard deviations imposed thereon.
Figure 25B:
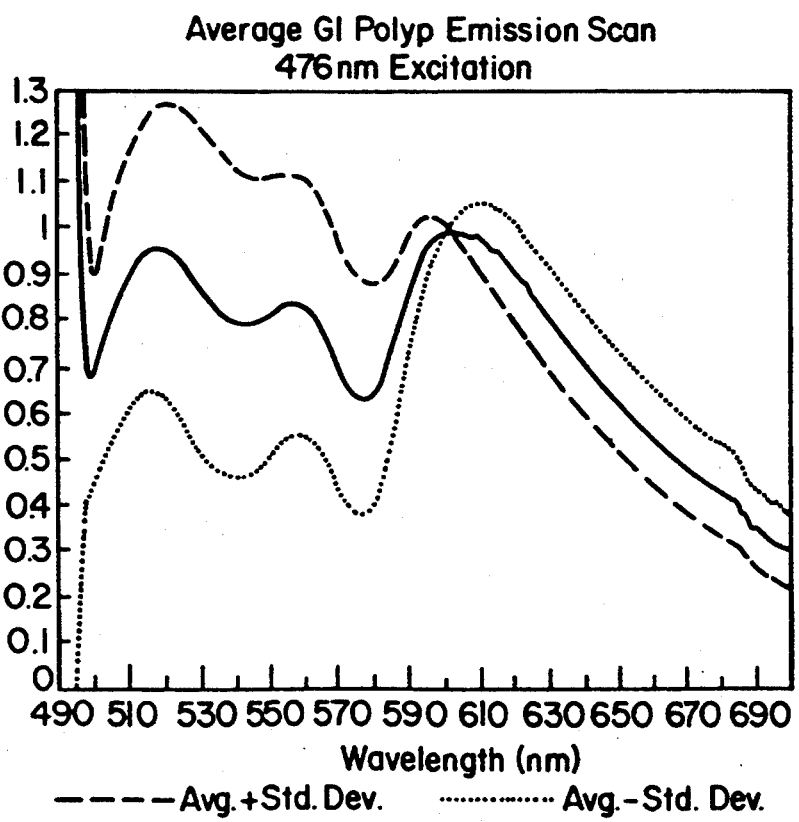

FIGS. 24(a) and (b) show average normalized fluorescence spectra of normal and adenomatous tissues with 476 nm excitation. These spectra are strikingly similar to typical arterial fluorescence spectra at this excitation wavelength. A fluorescence peak is present at 520 nm, with subsequent maxima at 550 and 600 nm produced by hemoglobin reabsorption. Average spectra±standard deviation spectra, shown in FIGS. 25(a) and (b) illustrate that the most variable region of these spectra are from 500 to 580 nm.

Figure 26:
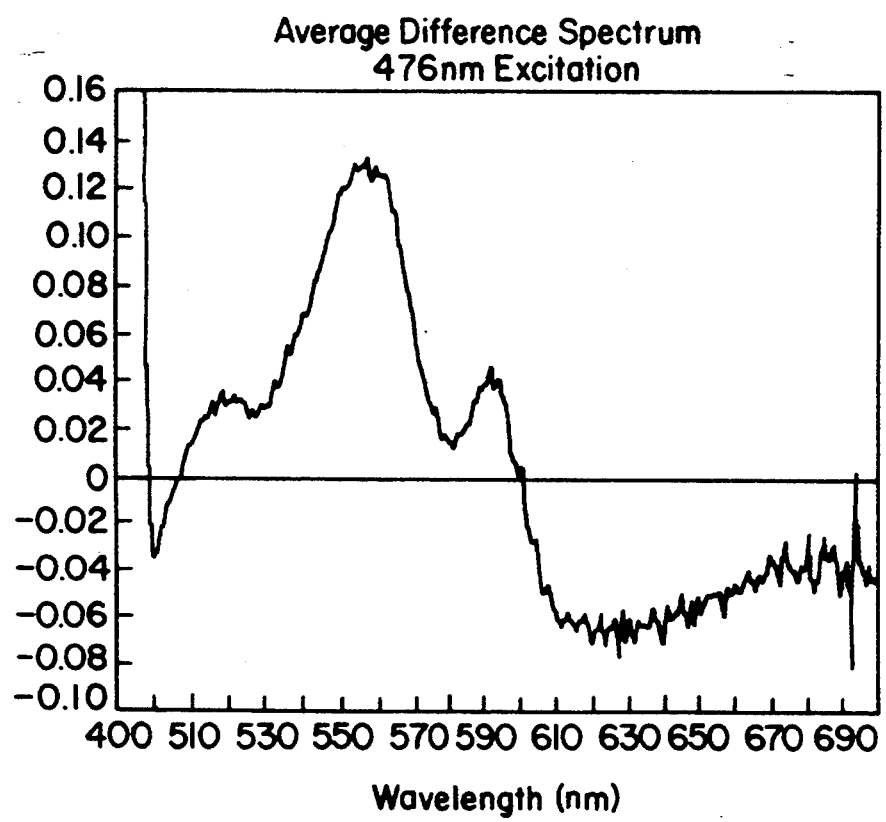
FIG. 26 illustrates an average difference spectrum at the 476 nm excitation.
Figure 27:
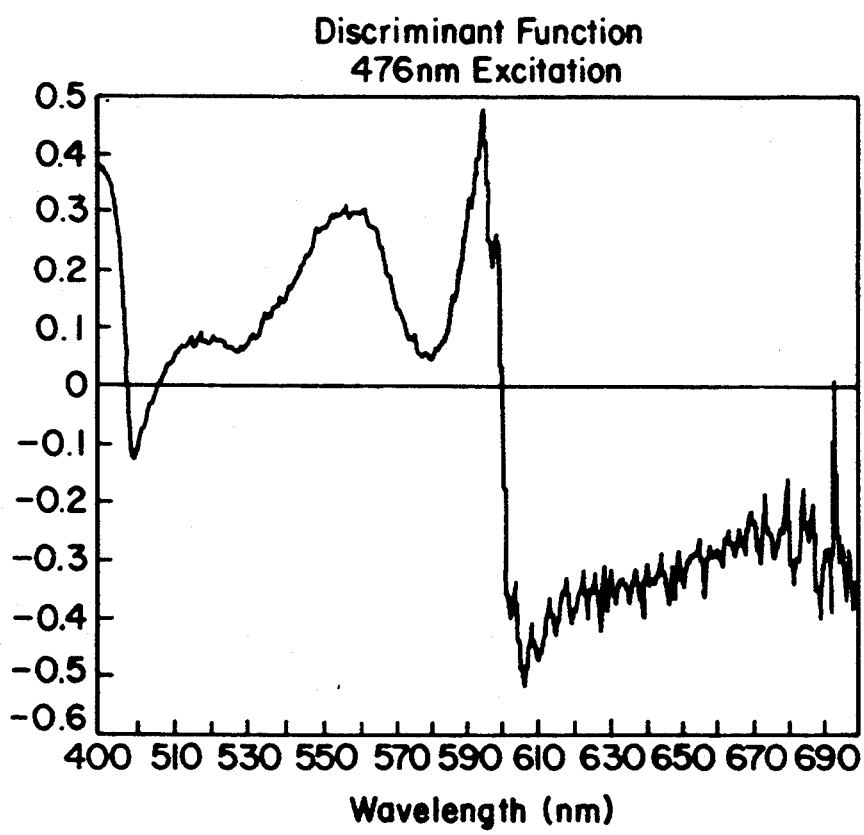
FIG. 27 illustrates the discriminant function at the 476 nm excitation.

At this excitation, normal tissues exhibit relatively more fluorescence at 630 nm, while adenomatous tissues show a relative increase in fluorescence intensity at 556 nm (FIG. 26). The discriminant function, FIG. 27 also illustrates these differences.

Three excitation wavelengths, 330, 350 and 370 nm, can be used in differentiating normal and adenomatous human colon tissue. At these excitation wavelengths, several fluorescence bands were identified where the relative fluorescence intensity of normal and adenomatous tissue differed. These are summarized in Table 4. Basically, four bands were noted at (330, 385) (330–370, 440), (350–370, 470) and (330–370, 560). Utilizing individual relative fluorescence difference spectra at these wavelengths, simple binary diagnostic procedures were defined. At each of these excitation wavelengths a correct diagnosis was achieved in greater than 80% of the samples.

TABLE 4

| λ Excitation | λ Difference Peak | Magnitude |
|---|---|---|
| 330 | 380 | −0.15 |
|  | 435 | 0.20 |
|  | 560 | 0.05 |
| 350 | 440 | 0.30 |
|  | 470 | −0.05 |
|  | 560 | 0.05 |
| 370 | 440 | 0.40 |
|  | 480 | 0.05 |
|  | 560 | 0.05 |

Figure 28:
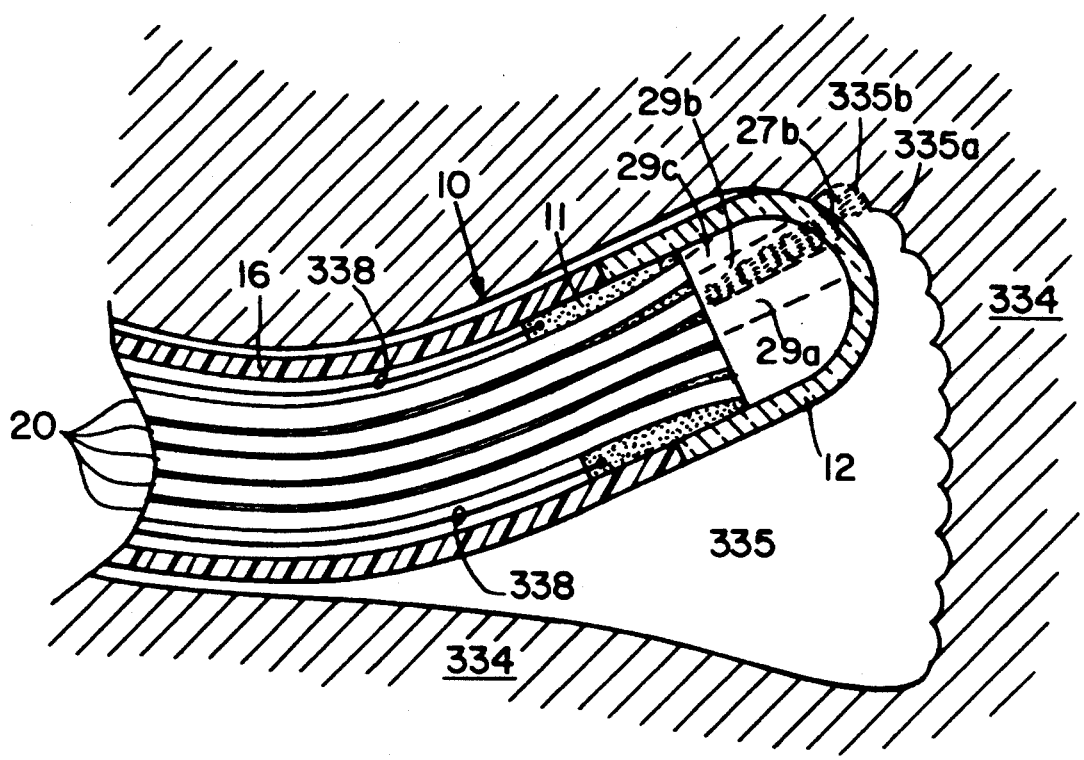
FIG. 28 illustrates the use of a laser catheter device for the in vivo diagnosis and treatment of tissue in accordance with the invention.

FIG. 28 illustrates the use of a laser catheter 10 used for the diagnosis and or removal of selected tissue 334. One or more fibers 20 may be positioned within a catheter tube 16 wherein the movement of the distal end of the catheter can be controlled by guidewires 338. The fibers 20 are held within tube 16 by plug material 11 such that a light spot pattern 27b is formed on the distal surface of an optical shield 12 positioned on the end of the catheter when a laser beam is connected to the proximal ends of the fibers 20 to project light onto the shield along paths 29a–c. Low energy diagnostic laser radiation can be used to perform the diagnostic procedure described herein or high power laser radiation can be used to remove "nibbles" of material 335 a and b. Systems and methods used in conjunction with the diagnosis and treatment of tissue in accordance with the invention are described in U.S. Pat. No. 4,913,142 incorporated herein by reference.

Figure 29A:
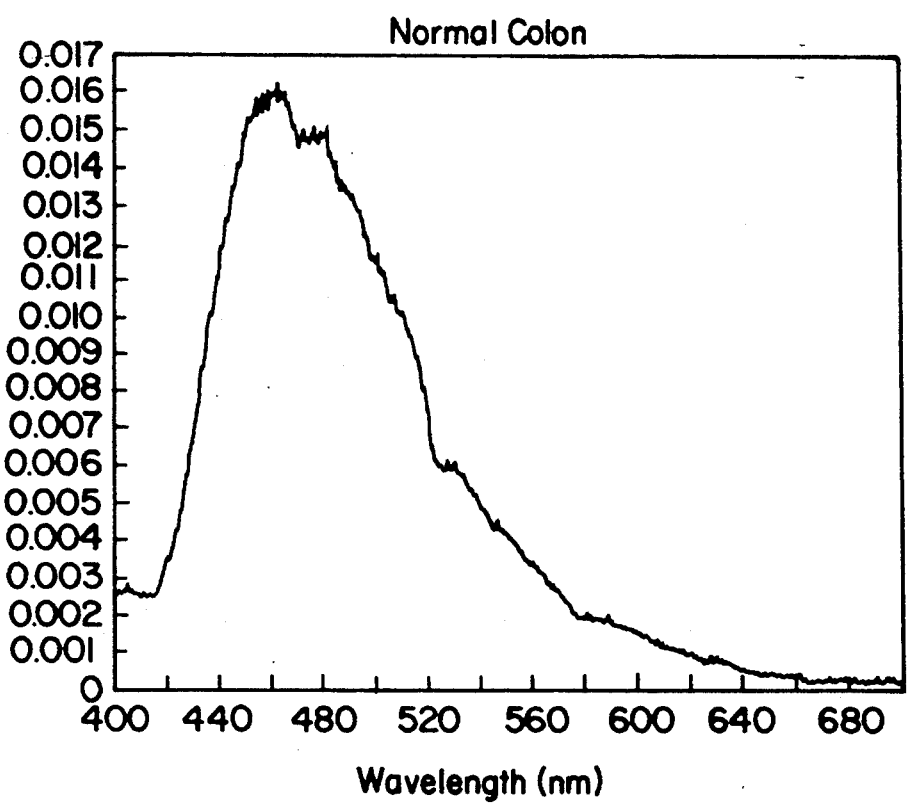
FIGS. 29a and b are average fluorescence spectra of normal colon and adenomatous colon tissue at an excitation wavelength of 369.9 nm.

FIG. 29A shows the average fluorescence emission spectrum of another set of samples of normal colon obtained with the spectral catheter system; the excitation wavelength was 369.9 nm. Two intense emission peaks are present near 460 and 480 nm. Valleys can be observed near 420, 540 and 580 nm. The small peak at 520 nm is an artifact due to a large decrease in the spectral response of the detection system at this wavelength. This spectrum is fairly similar to that obtained with the fluorimeter for normal tissue at 370 nm excitation, except that the peaks are slightly blue shifted here, the 480 nm peak is slightly more pronounced and the valleys are much less pronounced.

These differences can be understood in terms of the different collection geometries of the two systems. The collection geometry of the catheter system is well defined, that of the fluorimeter is not; thus, the attenuation contributions to spectra obtained with the fluorimeter will be greatly enhanced relative to those obtained with the catheter system. The valleys at 420, 540 and 580 nm are due to the attenuation effects of oxy-hemoglobin. They are more pronounced in spectra obtained with the fluorimeter. The attenuation contribution at 420 nm affects the observed maximum of the peak near 470 nm. In the spectrum obtained with the fluorimeter, there is relatively more attenuation at 420 nm, and the peak is observed at 470 nm. In the spectrum obtained with the catheter, there is relatively less attenuation at 420 nm, thus the observed position of the peak is blue shifted to 460 nm. This blue shift allows for better resolution of the second maximum at 480 nm in spectra obtained with the catheter.

Figure 29B:
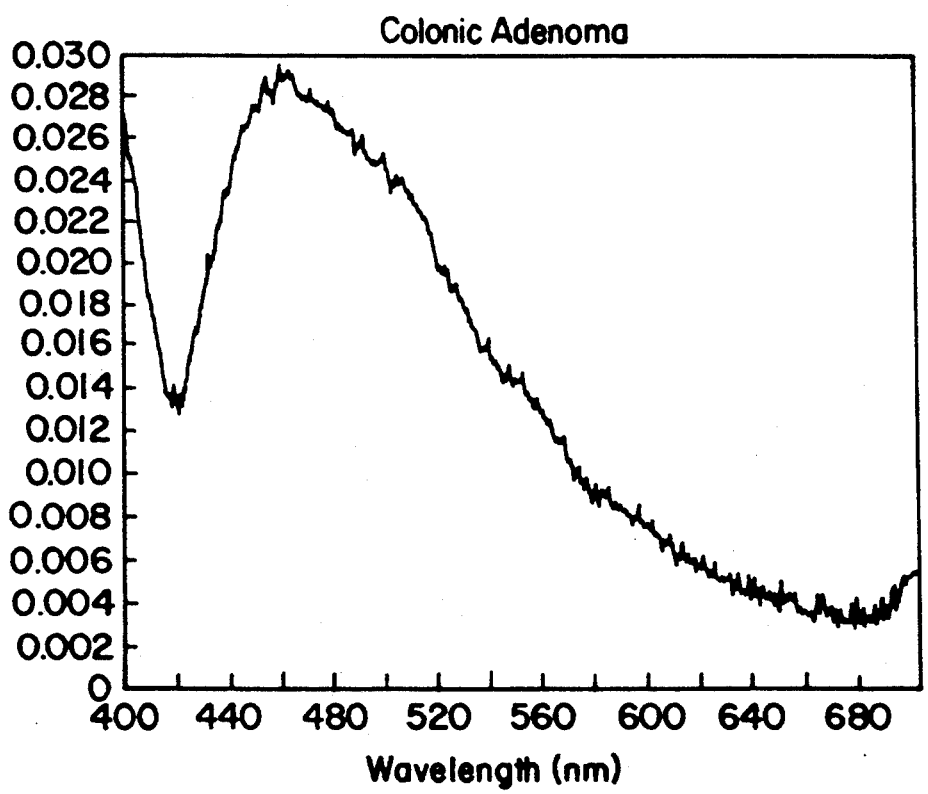

FIG. 29B also shows the average fluorescence emission spectrum of samples of adenomatous colon. Here, absolute fluorescence intensities have been preserved. This spectrum shows fluorescence peaks at 460 and 500 nm with valleys near 420, 540 and 580 nm. This spectrum is similar to that obtained with the fluorimeter except the valleys are less pronounced. Although, there is relatively more fluorescence in the 400–460 nm region of the adenoma spectra obtained with the catheter, the shoulder present at 450 nm in the spectra some of the adenomas obtained with the fluorimeter is not prominent in the adenoma spectra obtained with the catheter.

Figure 30A:
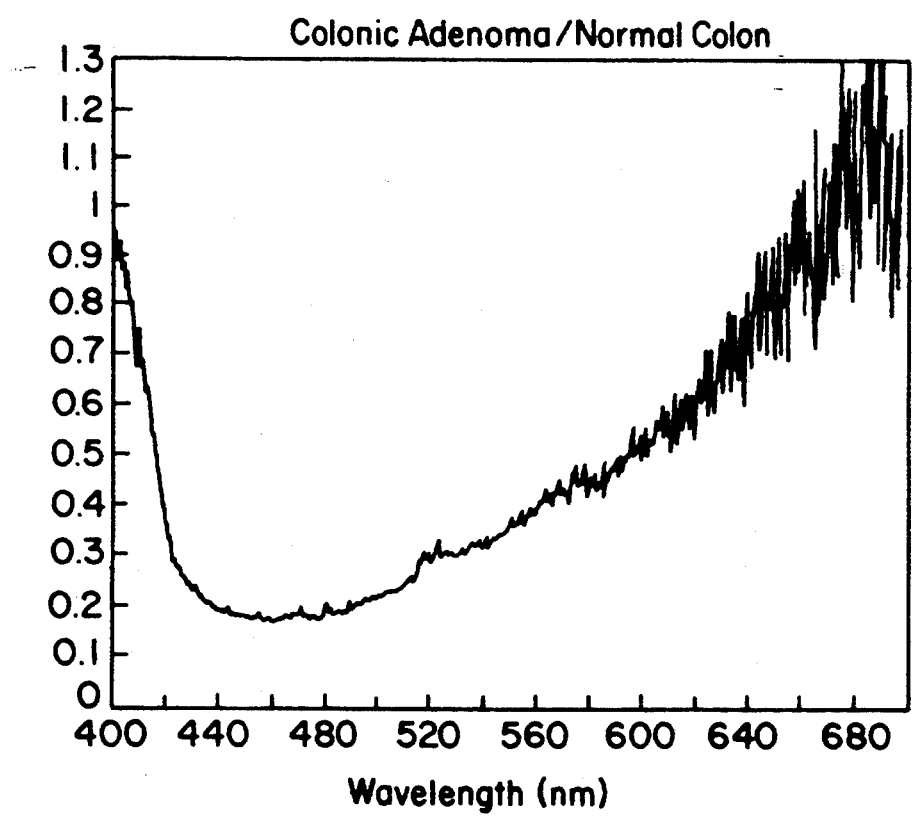
FIGS. 30a and b are graphical illustrations of the ratio and difference between the averaged and normal tissue spectra of FIG. 29, respectively.

The differences in the average spectra presented in FIGS. 29A and B include a larger fluorescence intensity in normal colon at 460 nm, a difference in the position of the second largest peak, at 480 in normal tissue and 500 nm in adenomatous tissue, and more pronounced valleys at 420, 540 and 580 nm in adenomatous tissue. These differences are characterized quantitatively in FIG. 30A, which shows the ratio of the average adenoma spectrum to the average normal tissue spectrum. This ratio spectrum is characterized by four regions: a downward sloping region from 400–480 nm, a flat region from 400–480 nm, an upward sloping region from 480–650 nm where the ratio is <1 and an upward sloping region from 650–700 nm where the ratio is >1.

These can be related to the differences in the average fluorescence spectra discussed qualitatively above. The downward sloping region from 400–420 nm reflects the blue region of the spectrum in which the relative fluorescence intensity of the adenomas is relatively greater than that of normal tissues. The flat region from 430–480 nm represents peak at 460 nm, where the fluorescence intensity of normal tissue is greater than that of adenomatous tissue. The relatively flat ratio in this region indicates that the fluorescence lineshape of this peak is the same in normal and adenomatous tissue. The upward sloping region from 480–650 nm represents a region where the absolute difference in the fluorescence intensity of normal and adenomatous tissue is decreasing, and is due to the red shift in the position of the second most intense maximum in the spectra of adenomatous tissues. Above 680 nm, the absolute fluorescence intensity in the adenoma spectrum is slightly greater than that in the normal spectrum. This difference peaks near 680 nm.

Figure 30B:
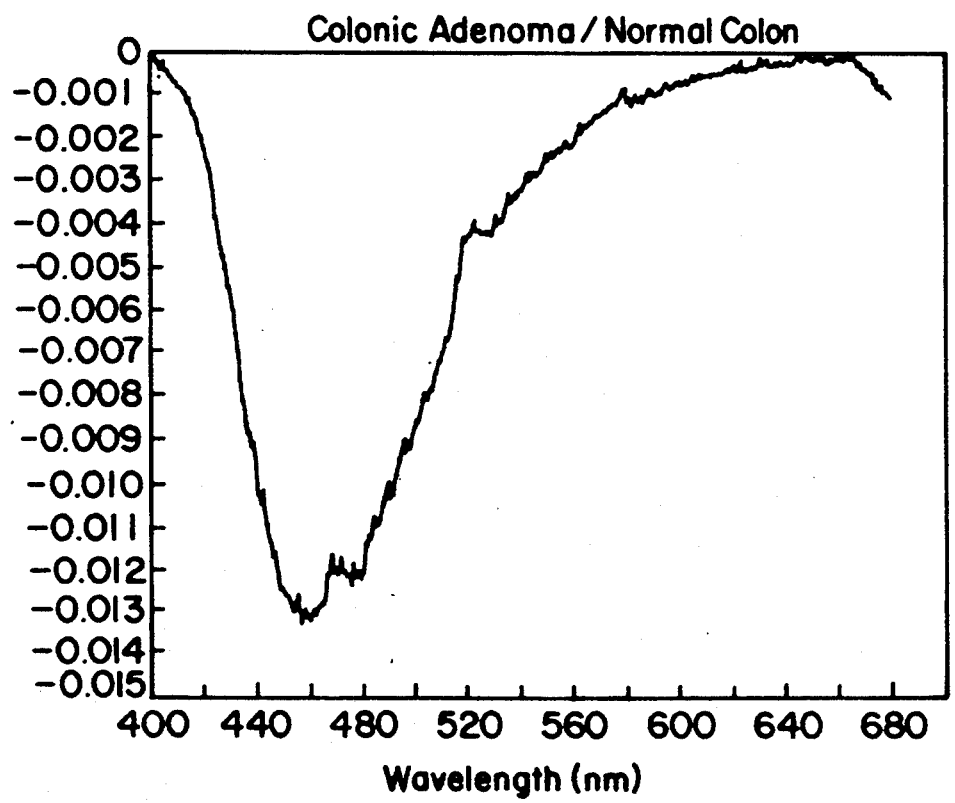

FIG. 30B shows the difference of the average adenoma and normal tissue spectra. This spectrum essentially reflects the same features observed in the ratio spectrum, except that the differences observed at 680 nm in the ratio spectrum are not a feature of the difference spectrum. Table 5 lists the locations of the local maxima and minima in the ratio and difference spectra shown in FIG. 16.

TABLE 5

Peaks in Average 370 nm Excited Difference and Ratio Spectra of Normal and Adenomatous Colon Tissue

| Emission λ | Maxima or Minima | Ratio, Difference or Both |
|---|---|---|
| 404 nm | Max | Both |
| 460 nm | Min | Both |
| 480 nm | Min | Difference |
| 516 nm | Min | Difference |
| 532 nm | Min | Difference |
| 600 nm | Min | Ratio |
| 680 nm | Max | Ratio |

Figure 31A:
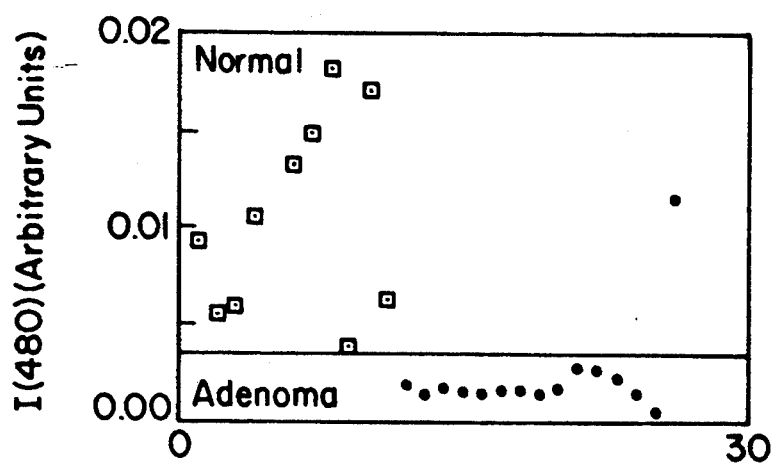
FIGS. 31a, b and c illustrate diagnostic methods used in distinguishing normal or adenoma based upon excitation at 369.9 nm.
Figure 31B:
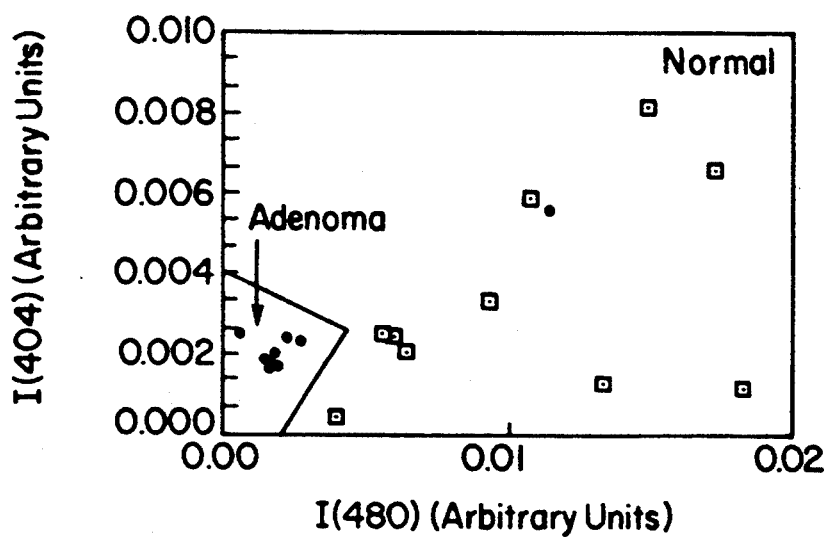
Figure 31C:
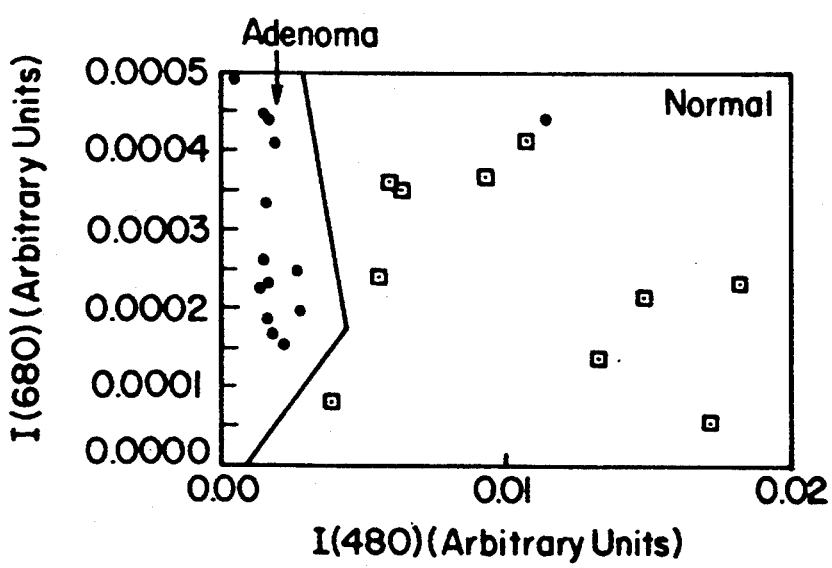

Empirical methods for the presence of adenoma were defined with the fluorescence intensities at emission wavelength listed in Table 5 using the method outlined above. FIGS. 31 a, b, c shows three diagnostic methods which are defined with this procedure. The emission intensity at 480 nm proved to be an effective diagnostic method for adenoma. FIG. 31a shows that a simple method represented by a straight line at I(480) - 0.003 is capable of correctly diagnosing 96% of the samples as normal or adenoma. Equally effective binary diagnostic methods could also be defined using the emission intensity at 480 nm with that at either 404 nm or 680 nm. These are shown in FIGS. 3b and 31c respectively. Here, again the methods represented by the two straight lines correctly classify 96% of the samples as normal or adenomatous. It should be pointed out, that, with this data set, the addition of another parameter does not improve the performance of the method. However, in the binary scatter plots there are fewer data points which fall near the decision surface. Thus, as the size of the data set is increased, these methods may prove to be more effective than the method based on fluorescence intensity at a single emission wavelength. The specificity, sensitivity and predictive value of these methods for detecting adenoma are 93%, 100% and 100% respectively. In all cases the same adenomatous sample is incorrectly diagnosed as normal.

Figure 32A:
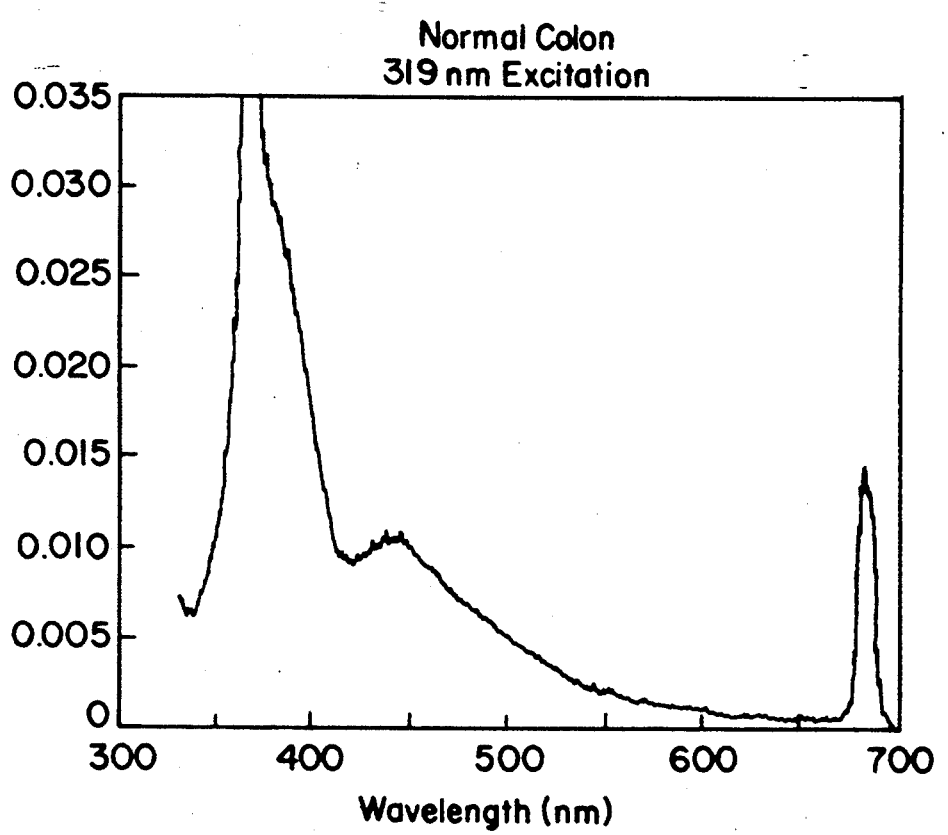
FIGS. 32a and b are averaged, normalized spectra of normal and adenomatous colon, respectively obtained at 319.9 nm excitation.
Figure 32B:
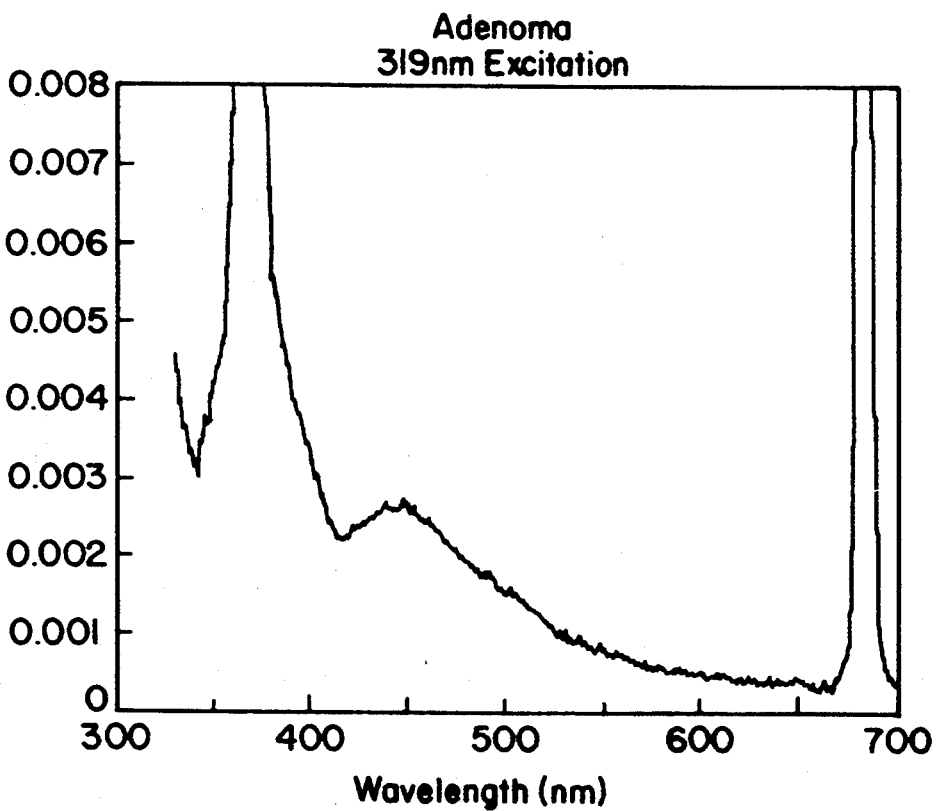
Figure 33A:
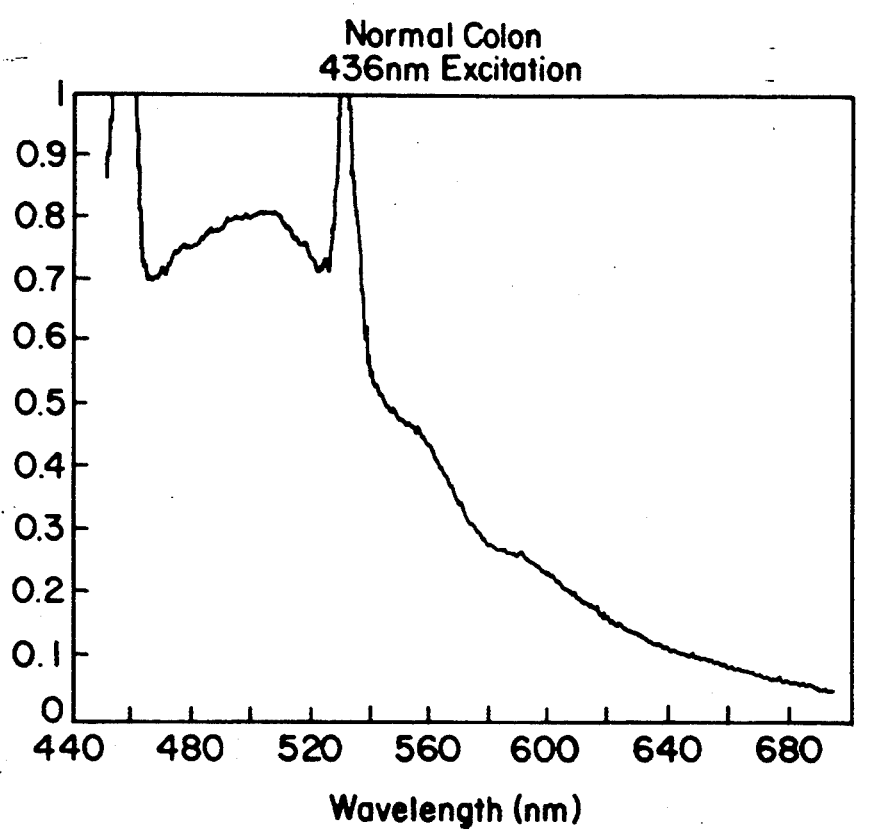
FIGS. 33a and b are averaged, normalized spectra of normal and adenomatous colon, respectively, obtained at 435.7 nm excitation.

In addition, fluorescence emission spectra were collected from this same set of samples at 319.9 and 435.7nm excitation. Although an analysis of this data will not be presented here, for reference, the average, normalized spectra of normal and adenomatous colon at these excitation wavelengths are shown in FIGS. 32a and b, and FIGS. 33a and b.

The patients in which in vivo measurements were taken were prepared for colonescopy by ingestion of an oral lavage solution (colyte). The Colyte was tested in vitro and does not interfere with LIF spectra collection.

Colonoscopy was performed using a standard procedure and colonoscope. In each patient, the probe 10 was passed through the accessory channel of the colonoscope and its outer shield 15 was placed in direct contact with the surface of mucosal polyps and/or control nonpolypoid normal-appearing mucosa. This contact displaced residual colonic contents and/or mucous. Direct contact was also necessary to fix the distance between the mucosa and the distal end 35 of the probe's optical fibers, so that reliable calibrated fluorescence intensity information could be obtained.

Fluorescence emission spectra were collected from 350–700 nm with a resolution of 0.6 nm. After three spectra were obtained, the probe was removed and then repositioned two to four additional times with three spectra obtained at each placement. This process yielded nine to 15 individual spectra per site. No appreciable fluorescence photo-bleaching was observed. A biopsy for histologic examination was then performed of the mucosal site analyzed by the probe. Polyps were treated by standard electrosurgical snare polypectomy or coagulation-biopsy ("hot biopsy") in the case of diminutive polyps. Tissues were categorized histologically as normal, hyperplastic polyp, tubular adenoma, tubulovillous adenoma, villous adenoma, or as tissue insufficient for diagnosis.

Spectra were corrected for non-uniform spectral response of the detection system by using a calibrated lamp. The fluorescence intensity of a standard fluorescence paper was measured prior to study in each patient and was used to calibrate the fluorescence intensity of the tissue spectra. The spectral baseline was corrected to zero by substracting a constant background (dark current) which was measured along with each spectrum.

Data were reduced by computing an average spectrum and a standard deviation from the corrected spectra obtained from each site. The average spectrum per site was used in all further data manipulations. These average per site spectra were grouped according to histologic categories into the following categories: normal, adenoma, and hyperplastic polyp. For each histologic category the average and standard deviation spectra were calculated. The results were compared using a one-sided student t-test and p values of less than 0.05 were considered significant.

LIF spectra were obtained in vivo and analyzed from adenomas, hyperplastic polyps, and histologically normal areas. The adenomas ranged in size from 2–11 mm (average 5 mm) while the hyperplastic polyps measured 2–5 mm (average 3 mm). The adenomas were classified as tubular, villous, or tubulovillous. The laser caused no tissue damage that could be detected at the light microscopic level.

Figure 33B:
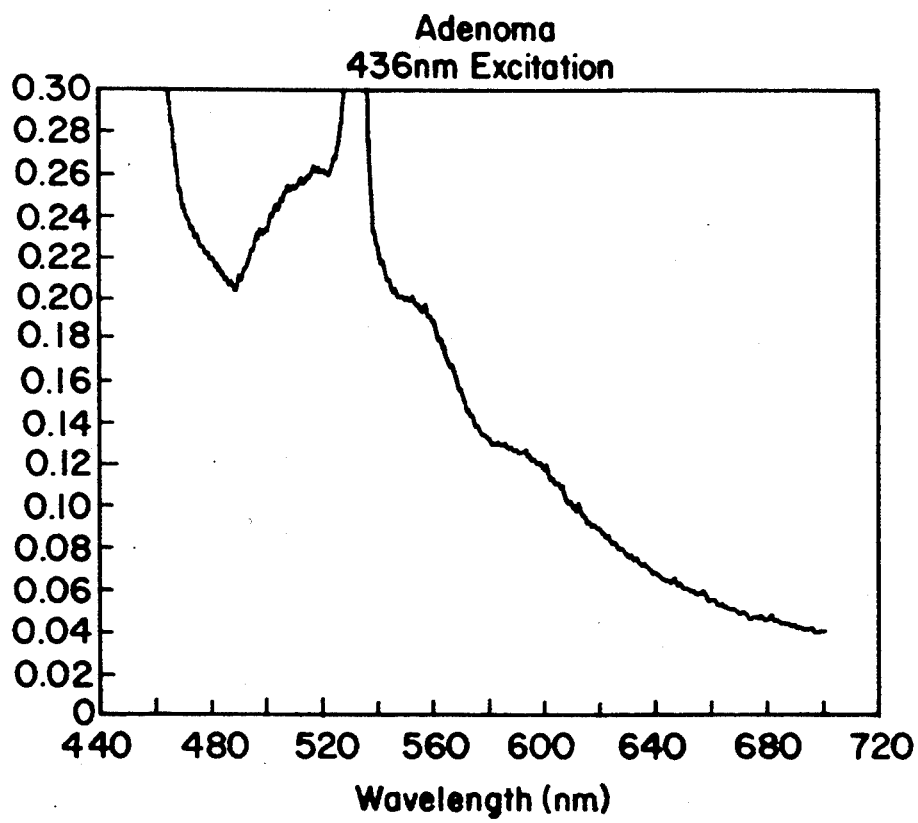
Figure 34:
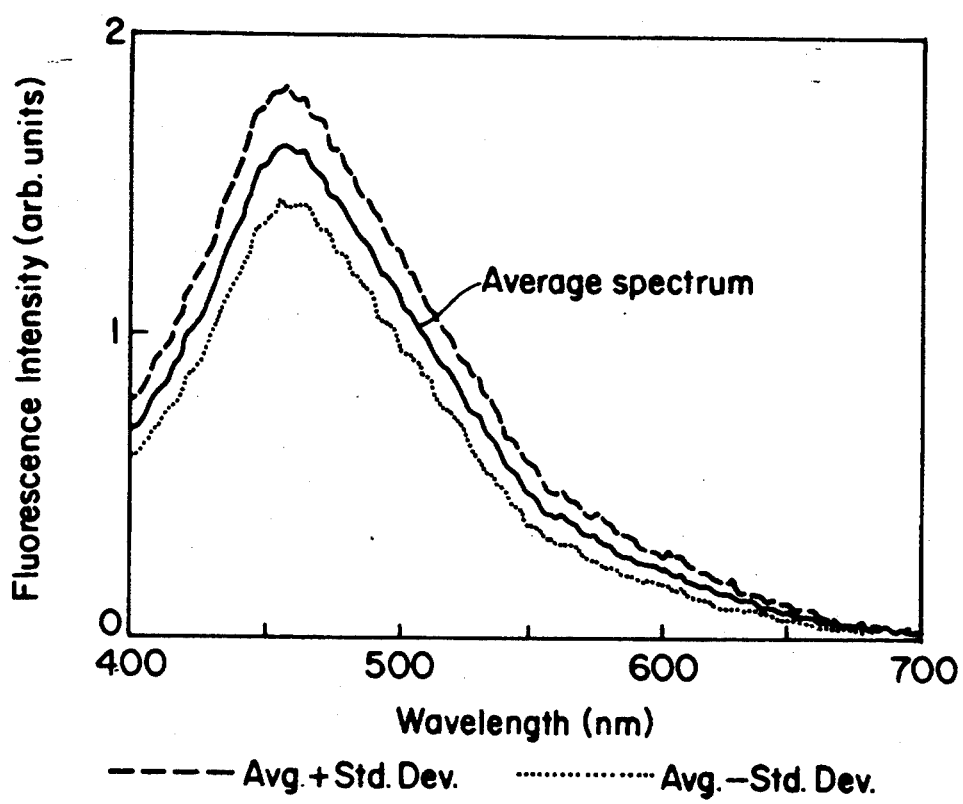
FIG. 34 illustrates an average spectrum with $\delta$ standard deviation for normal colon.
Figure 35:
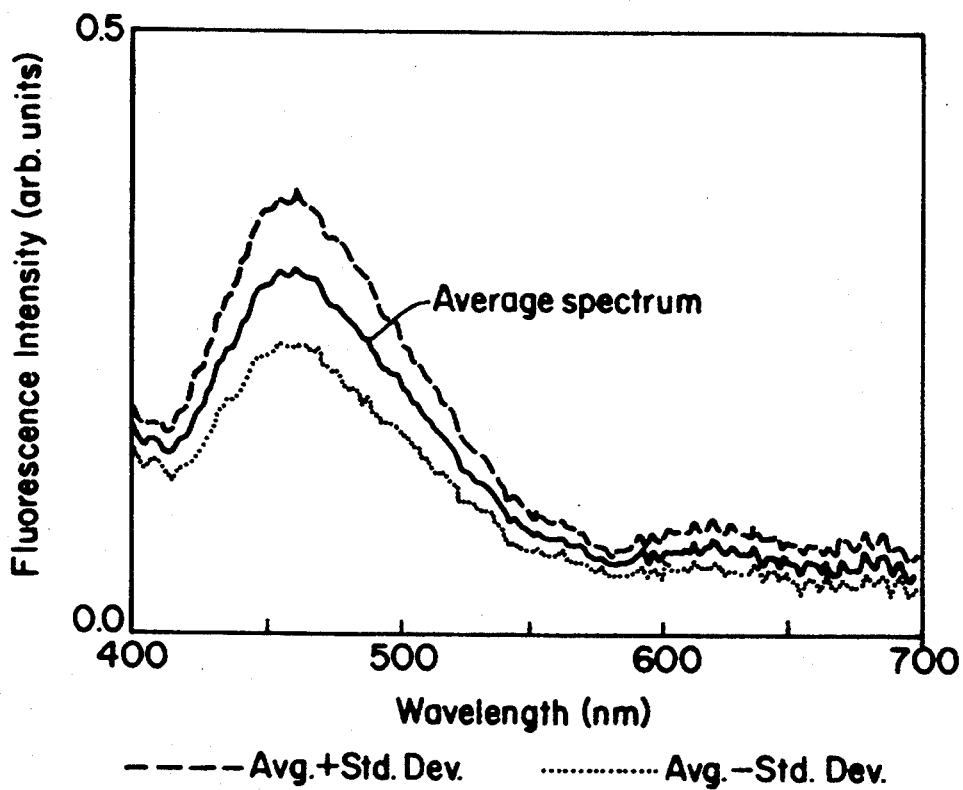
FIG. 35 illustrates an average spectrum with $\delta$ standard deviation for adenoma.
Figure 36:
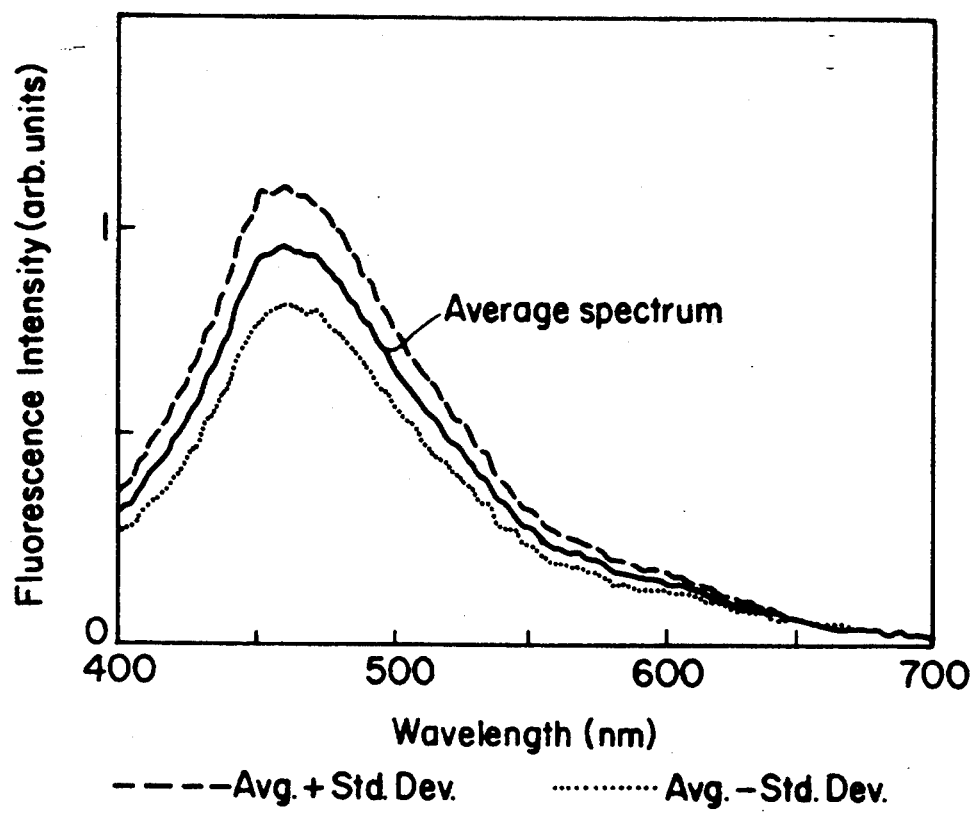
FIG. 36 illustrates an average spectrum $\delta$ standard deviation for hyperplastic polyp.
Figure 37:
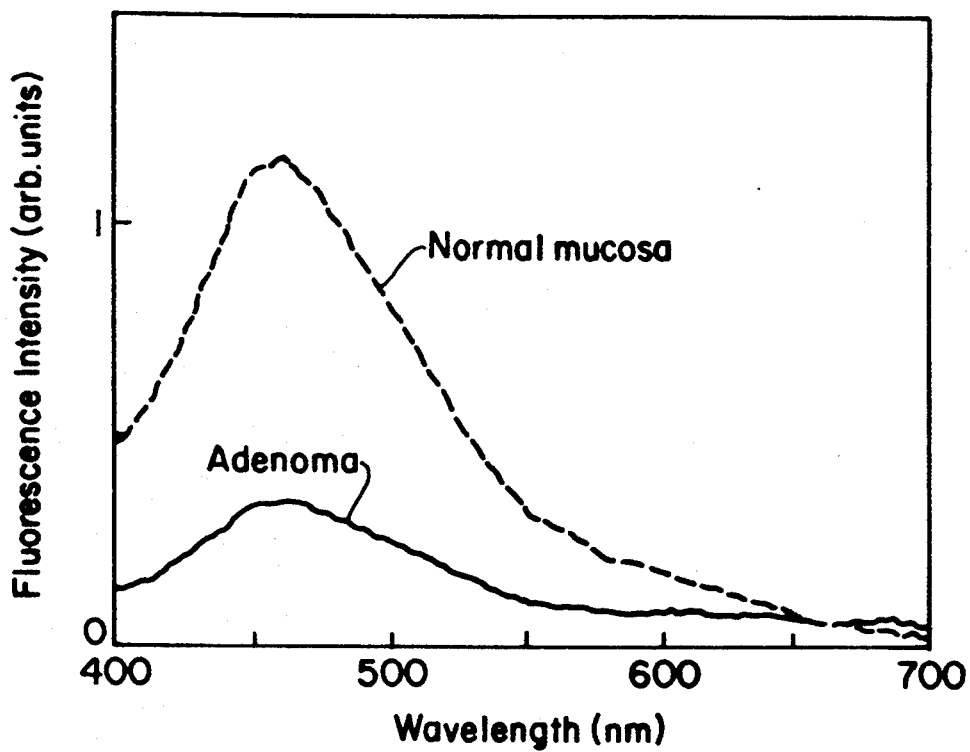
FIG. 37 illustrates an average spectrum for adenoma superimposed on an average spectrum for normal colon.
Figure 38:
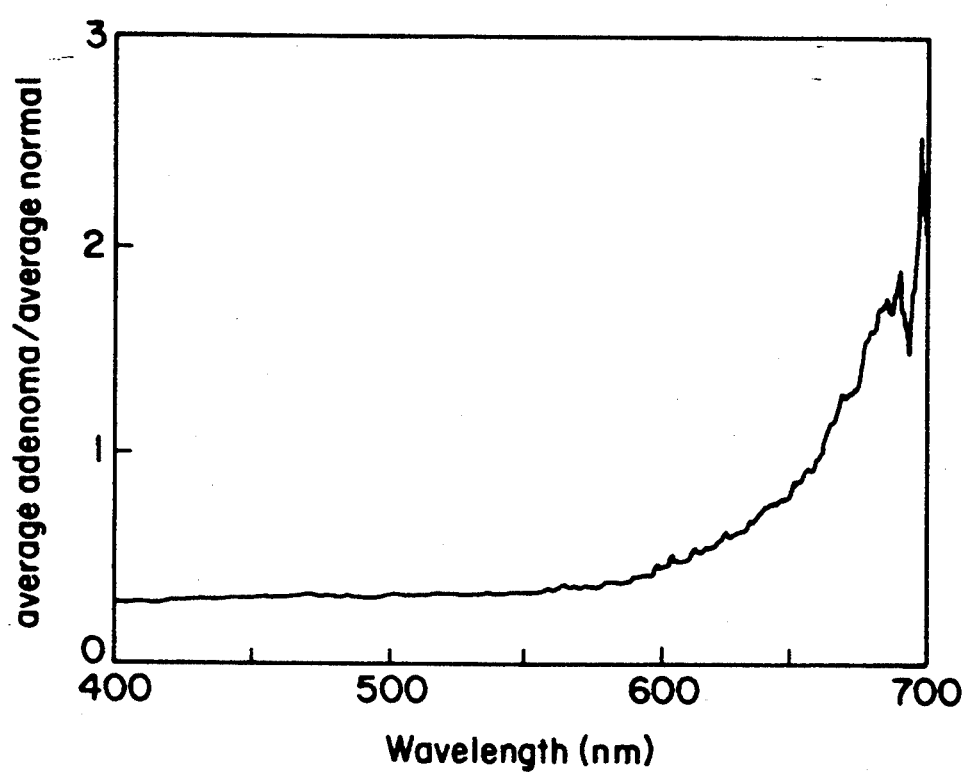
FIG. 38 illustrates the calculated ratio of the average adenoma spectrum to the normal spectrum.

FIGS. 34, 35 and 36 illustrates typical average LIF spectra±standard deviation for spectra obtained from a representative normal colon, adenoma, and hyperplastic polyp, respectively at 370 nm excitation. These data emphasize that the LIF spectra obtained in vivo were reproducible with standard deviations of less than 20%. Superficially, the spectra of normal colon, adenoma, and hyperplastic polyp appeared to have a similar lineshape but closer inspection demonstrated differences, especially between the spectra obtained from normal colon and adenoma. FIG. 37 illustrates the average of all adenoma spectra superimposed upon the average of all normal spectra. The spectra showed differences in two areas. The fluorescence intensity at 460 nm was approximately four times greater in normal mucosa as compared to adenoma. In addition, the fluorescence intensity at wavelengths greater than 650 nm was consistently greater in adenoma when compared to normal. These differences are quantitatively illustrated in FIG. 33 which shows the calculated ratio of the average adenoma spectrum to normal. At wavelengths less than 560 nm the ratio of fluorescence intensities of adenoma to normal was constant and less than one. This indicated that there were no differences in the lineshape of the spectra, but the values of fluorescence intensities differed. At wavelengths greater than 560 nm, the lineshape of the spectra differed and the relatively increased fluorescence of adenomas manifested itself as an upward slope in this graph (see FIG. 38). Analysis of these data suggested that for diagnostic purposes analysis can be simplified to a study of the fluorescence intensities at two wavelengths, 460 nm and 680 nm. As FIG. 38 indicates, below 560 nm the lineshape of the spectra of adenoma and normal were similar and the ratio of fluorescence intensities constant and less than one. This indicated that similar diagnostic information can be obtained at any wavelength in this region. Experimentally, fluorescence intensity information can be measured most easily at 460 nm, as this corresponds to the peak fluorescence intensity for both adenoma and normal mucosa and there is less noise in the measurement of fluorescence in regions of high fluorescence intensity. At wavelengths greater than 560 nm the spectra of adenoma and normal mucosa differed, with the differences maximal near 680 nm. This wavelength corresponded to a peak in the fluorescence of adenoma.

There were slight differences in the spectral lineshapes in the subcategories of adenomas (tubular adenoma, tubulovillous adenoma, and villous adenoma). The fluorescent lineshape of the villous adenomas examined differed from the tubular adenomas in that the 620 and 680 nm subsidiary peaks were less distinct. However, there were no significant differences between the average fluorescence intensities in the subcategories of adenomas at 460 nm or 680 nm.

Figure 39:
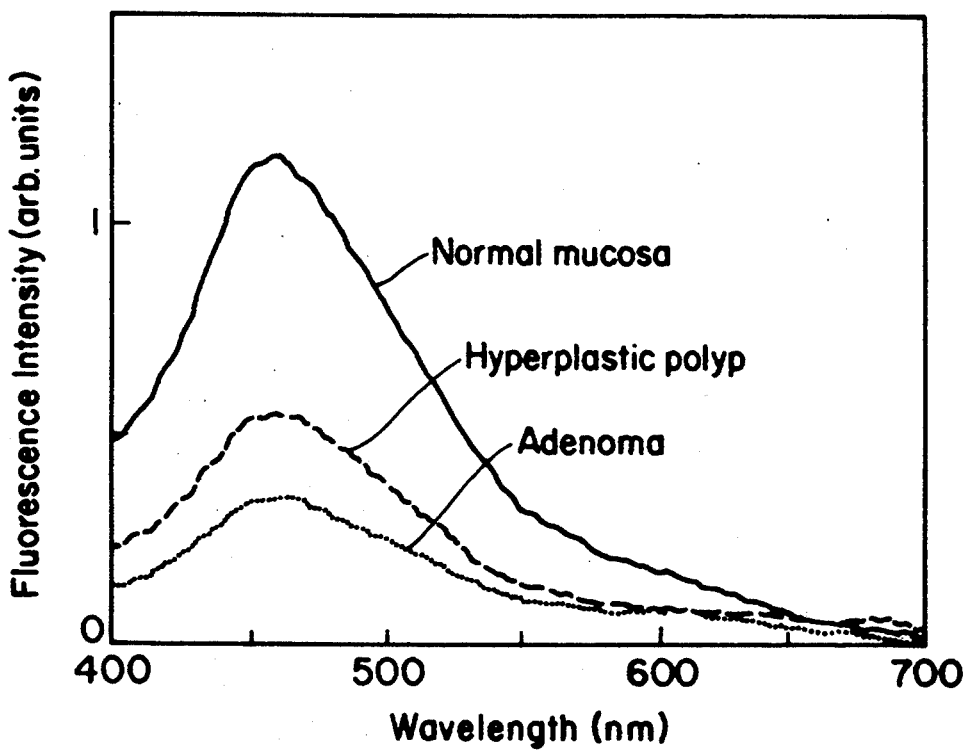
FIG. 39 compares the average spectrum for hyperplastic polyps relative to those for normal and adenoma.

FIG. 39 demonstrates the average fluorescence spectrum of all hyperplastic polyps superimposed on normal and adenoma spectra. The hyperplastic polyp fluorescence intensity at 460 nm lies intermediate between those of adenoma and normal mucosa and closely approximates that of normal at 680 nm.

Table 6 lists the mean fluorescence intensities at 460 nm and at 680 nm for all samples in each histologic.

TABLE 6

AVERAGE FLUORESCENCE INTENSITIES + STANDARD DEVIATION AT 460 nM AND 680 nM FOR ALL HISTOLOGIC CATEGORIES

| Histologic Category | Average Intensity at 460 nm | p Value | Average Intensity at 680 nm | p Value |
|---|---|---|---|---|
| Normal | 1.15 ± 0.43 | — | 0.037 ± 0.023 | — |
| Hyperplastic polyp | 0.54 ± 0.16 | 0.023 | 0.03 ± 0.02 | NS |
| Adenoma | 0.34 ± 0.12 | 0.0001 (vs. normal) 0.006 (vs. hyperplastic polyp) | 0.06 ± 0.05 | 0.004 (vs. norma) NS (vs. hyper plastic polyp) | p values are given for a one-sided student t-test.

Figure 40:
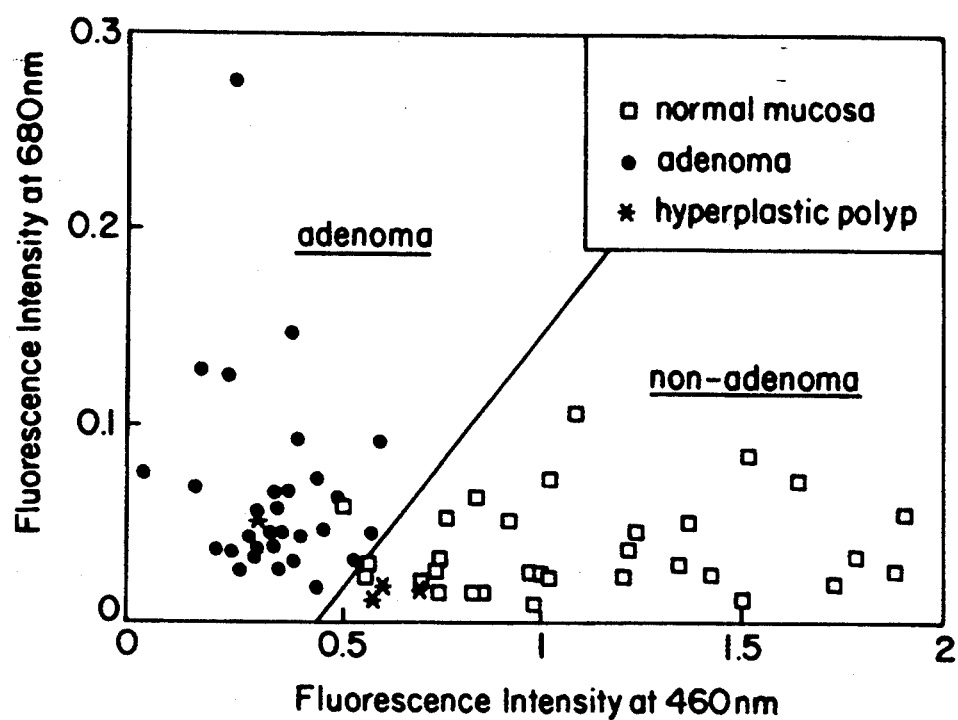
FIG. 40 is a scatter plot of the average fluorescence intensity at 460 nm versus 68 nm for each measurement.

The fluorescence intensities of hyperplastic polyp and adenoma were statistically significantly different from that of normal mucosa at 460 nm. At 680 nm the fluorescence intensity of hyperplastic polyps was similar to that of normal mucosa while the fluorescence intensity of adenoma was again statistically significantly different. A single 2-dimensional scatter plot of the average fluorescence intensity at 460 nm versus 680 nm for each specimen is shown in FIG. 40. The scatter plot was divided into two regions corresponding to adenoma and nonadenomatous tissues (normal colon and hyperplastic polyp) using a straight line decision surface chosen to minimize the number of misclassified samples. This decision surface correctly classified 97% of the 67 samples as adenoma or nonadenoma. No adenomas were misclassified. This procedure retrospectively diagnosed adenoma with a sensitivity of 100%, and a specificity of 97%. The predictive value of a positive test for adenoma was 94%.

Several studies have emphasized that adenomas cannot be reliably distinguished from nonadenomatous mucosa using macroscopic evaluation through the endoscope, especially when dealing with small lesions. The accuracy rate for diagnosis based on gross observation alone generally approximates 75%.

As a result, microscopic analysis is necessary and requires biopsy. Biopsy is time consuming, is associated with some risk to the patient, and leads to additional expense.

LIF spectra can be used in the recognition and differential diagnosis of mucosal abnormalities during endoscopy. Both in vivo and in vitro spectral results demonstrated that the diagnosis of adenoma can be made using LIF spectroscopy with a high degree of accuracy. The in vivo LIF spectroscopy lineshapes were in general substantially similar to the in vitro observations except for a 440 nm peak that was observed in some of the adenomas studied in vitro that was not clearly identified in adenomas studied in vivo. The in vivo LIF spectroscopy indicated that adenoma could be distinguished from nonadenomatous tissue in approximately 97% of cases.

A fluorescence spectroscopy diagnostic system capable of detecting adenoma (dysplastic/neoplastic) transformation is of great practical importance. Currently, no non-invasive technique is available to detect adenoma or other premalignant conditions (dysplasia) in the gastrointestinal tract. The ability to distinguish adenoma from hyperplastic and normal mucosa would save considerable time during colonoscopy as well as decrease the risk and cost of the procedure itself. More importantly, however, the alterations in cellular constituents responsible for the fluorescence spectroscopy lineshape differences seen in adenomas as compared to normal tissue is not unique to the dysplasia associated with colonic adenomas. Premalignant changes (dysplasia) associated with Barrett's esophagus and mucosal ulcerative colitis frequently are histologically identical to adenomas. If the same abnormalities responsible for the fluorescence spectral changes found in even some of the dysplasias associated with Barrett's esophagus or inflammatory bowel disease, the fiberoptic device described herein can identify dysplasia (neoplastic transformation) and provide a diagnosis of dysplasia by fluorescence spectroscopy alone or, can be used to direct biopsies to areas more likely to contain dysplasia.

The above demonstrated that fluorescence spectroscopy is a useful technique for diagnosing the presence of colonic adenoma. However, the diagnostic procedures presented thus far have been achieved with an empirical analysis of tissue fluorescence spectra. The following demonstrates that the fluorescence spectra of tissue are directly related to the histochemical composition of tissue. We compare the fluorescence excitation-emission matrices (EEMs) of tissue to fluorescence EEMs of pure biomolecules to obtained a potential identification of tissue fluorophores at the chemical level. In addition, tissue fluorophores at 370 nm excitation are identified at the morphologic level, using fluorescence and light microscopy of stained and unstained sections of tissue. The optical properties of these morphologic constituents of tissue are measured with 370 nm excited fluorescence microspectroscopy. This provides the basis for applying models of tissue fluorescence to the fluorescence spectra of colonic tissue.

In general, tissue fluorescence spectra contain contributions from both intrinsic fluorescence and attenuation. In order to compare the EEMs of pure biomolecules to tissue EEMs, it is first necessary to separate the effects of attenuation from tissue EEMs.

Total reflectance spectra provide a measure of the attentuation contributions to tissue EEMs. In a total reflectance spectrum, valleys indicate peaks in attenuation. These attenuation peaks can be related to the tissue EEMs in the following way. Attenuation peaks act to produce valleys in the fluorescence spectra of optically thick tissue samples. As attenuation effects are important both for exciting and emitted radiation, valleys will be produced in both excitation and emission spectra. Thus, at the location of these attenuation peaks, one expects to see valleys in the tissue EEMs parallel to both the excitation and emission axes.

Attenuation effects, which include both scattering and absorption, were recorded independently by measuring total reflectance spectra of eight (four normal, four adenoma) full thickness colonic specimens from four patients using a standard absorption spectrophotometer equipped with an integrating sphere. Three of the normal samples were matched controls from patients with familial adenomatous polyposis. Percent total reflectance was recorded from 250–700 nm with a resolution of 5 nm FWHM.

Figure 43:
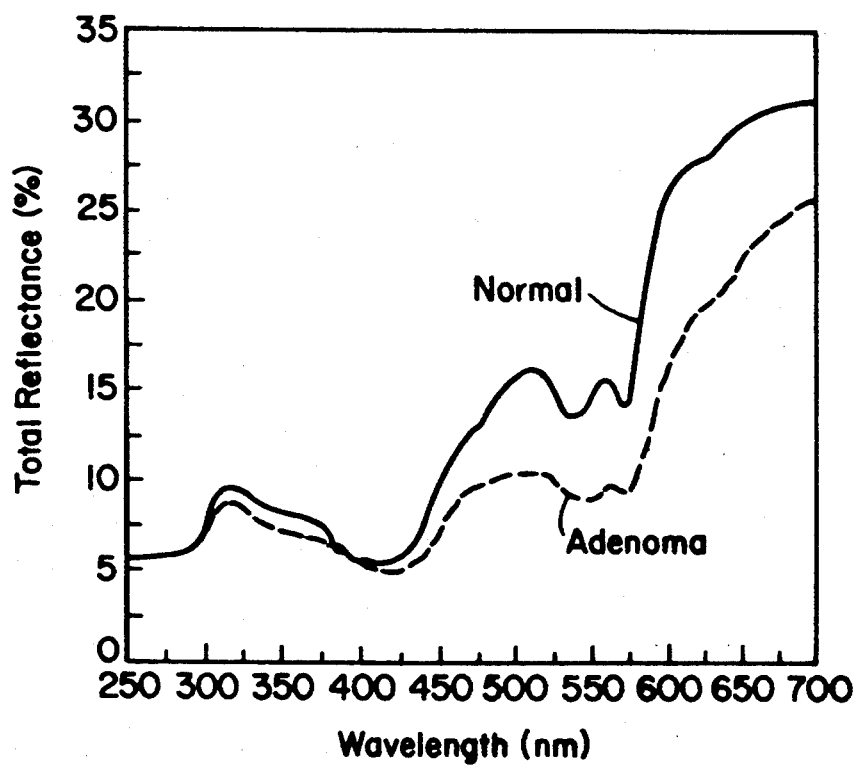
FIG. 43 illustrates average total reflectance spectra of normal colon and colonic adenoma.
Figure 44A:
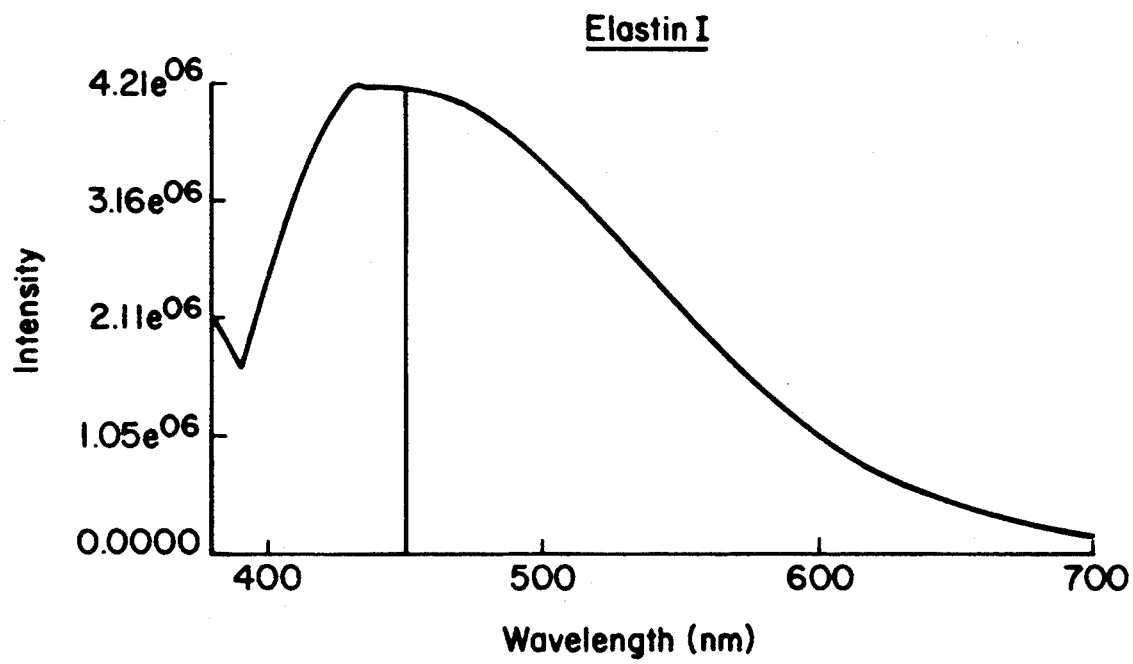
Figure 44B:
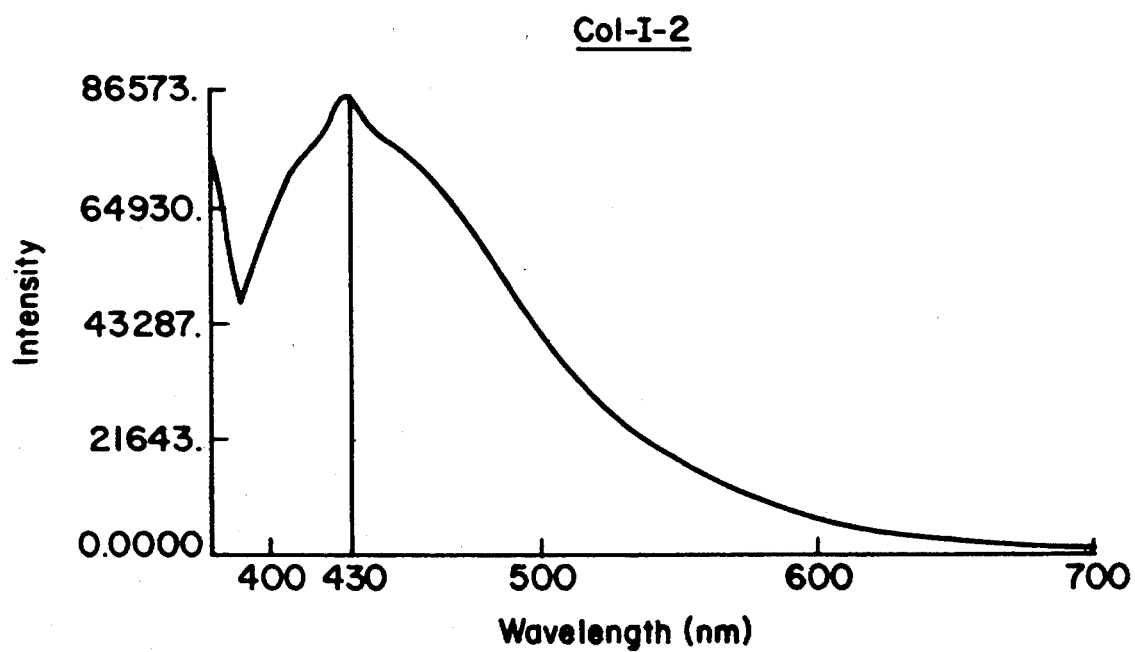
Figure 44C:
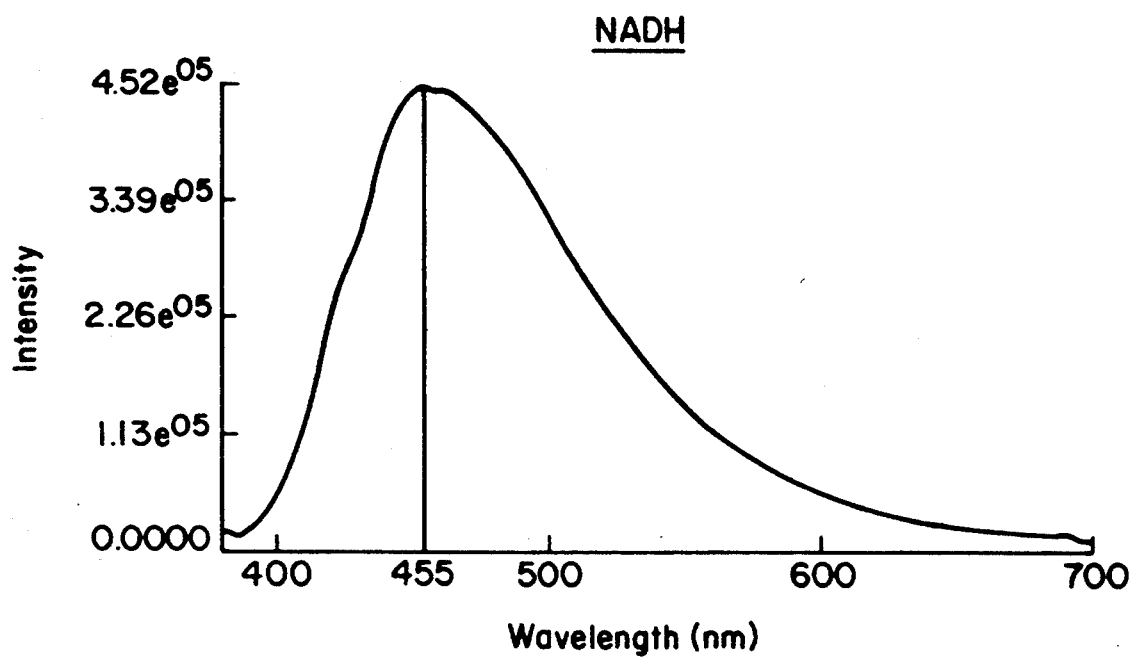
Figure 44D:
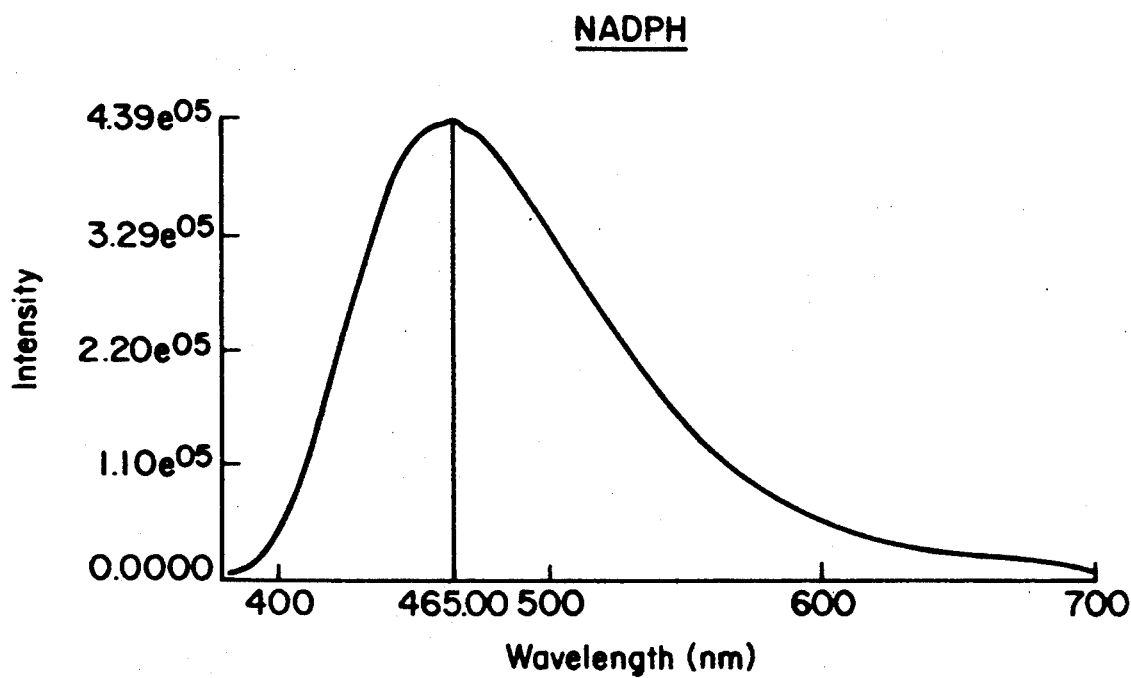
Figure 44E:
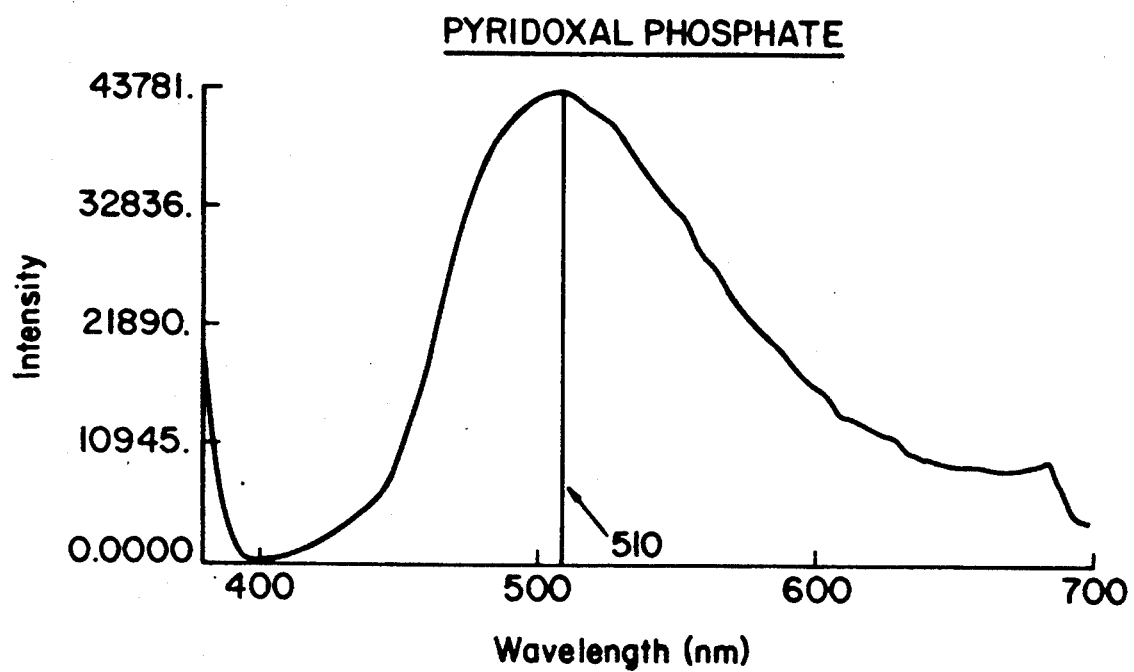
Figure 45A:
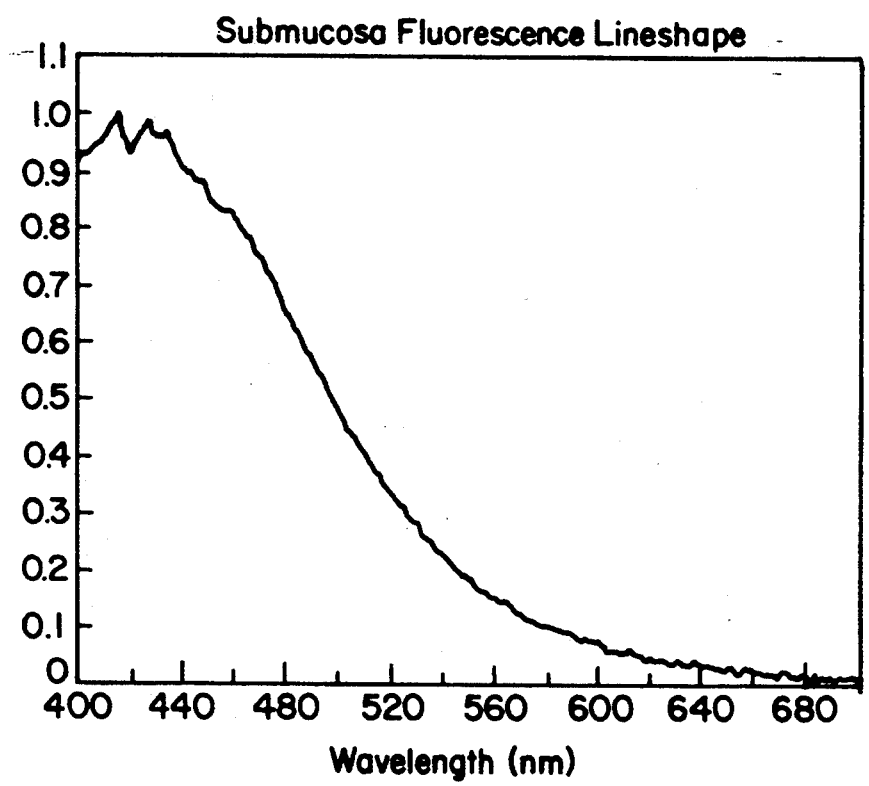
FIGS. 45a-e show average spectra for selected morpholophores.
Figure 45B:
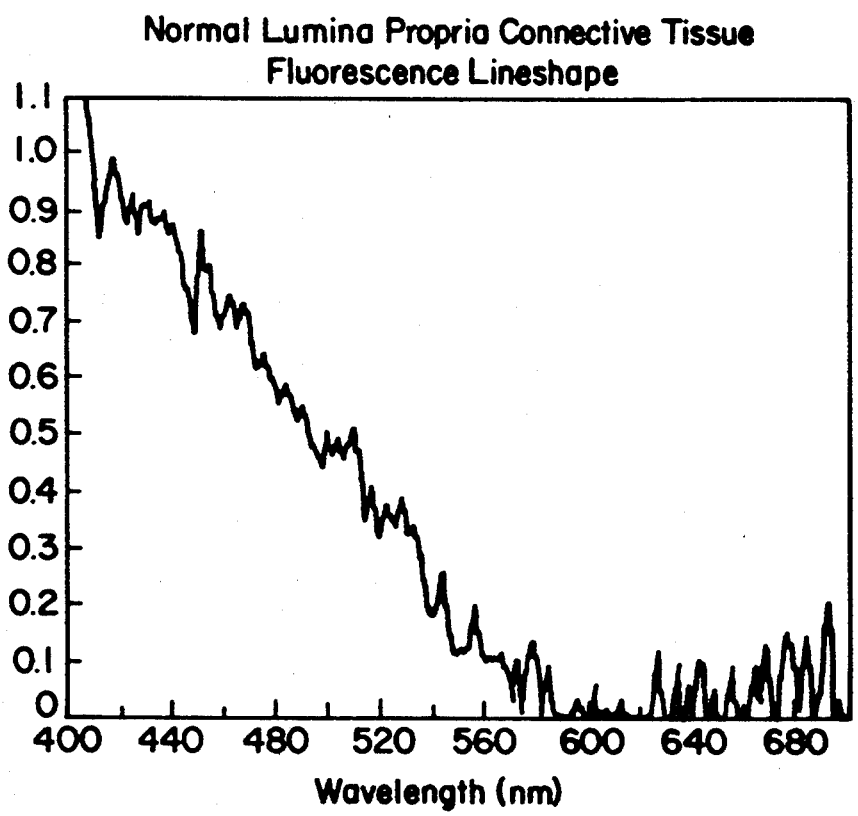
Figure 45C:
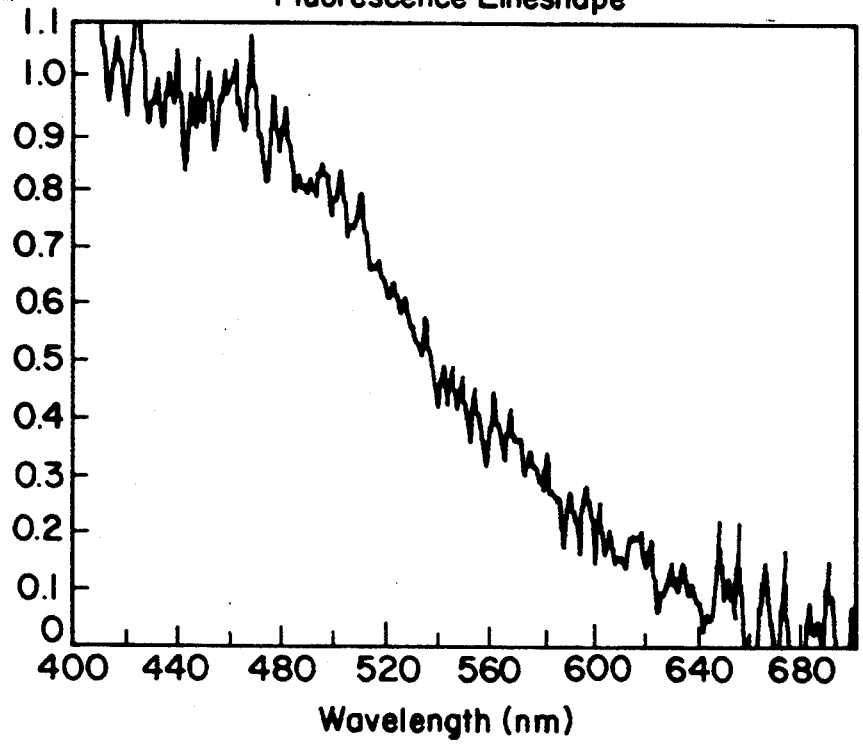
Figure 45D:
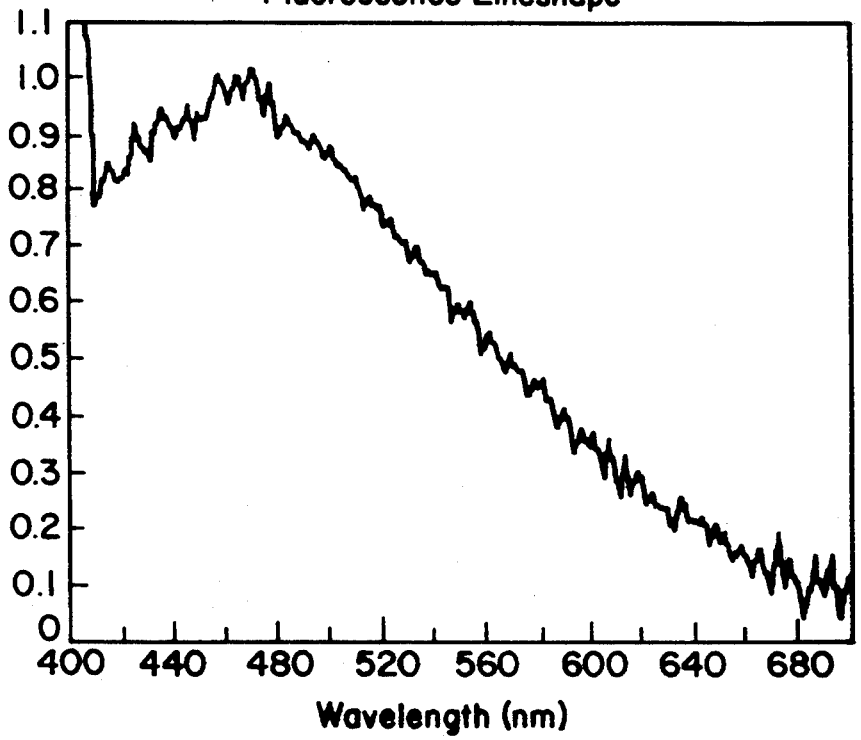
Figure 45E:
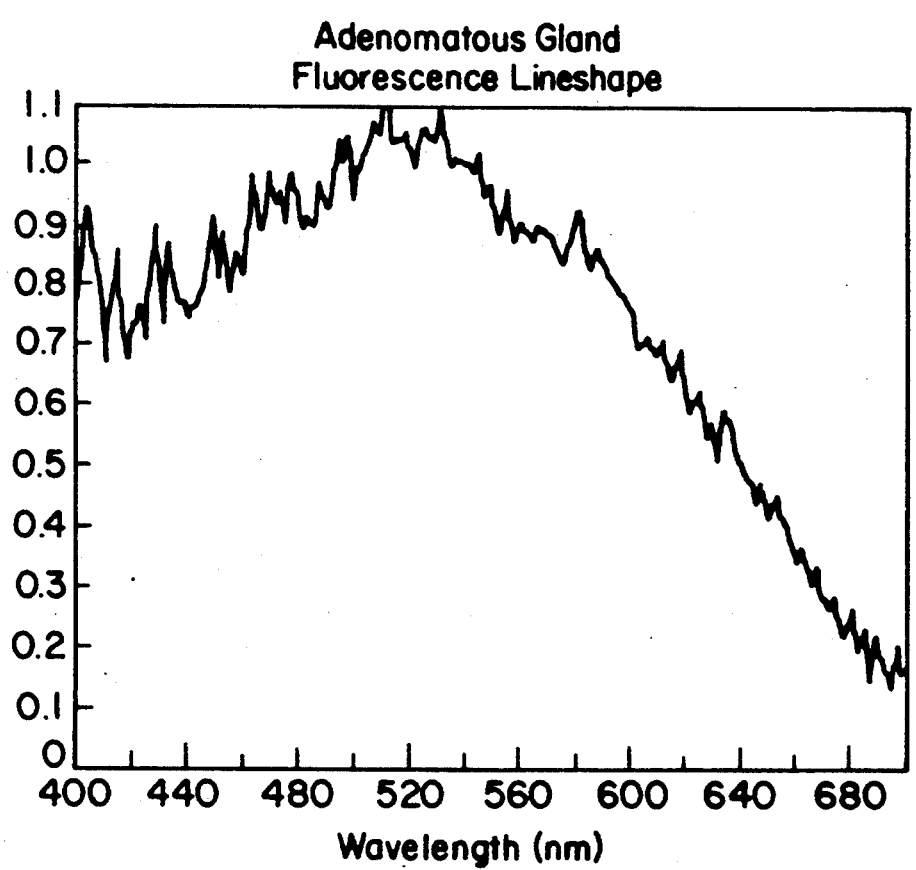

FIG. 43 shows average total reflectance spectra of four samples of normal colon and four colonic adenomas. In both types of tissues, reflectance valleys are located at 270, 355, 420, 540, 575, and 635 nm. These valleys are superimposed on a gently upward sloping background, which is slightly steeper for normal tissue.

Figure 42:
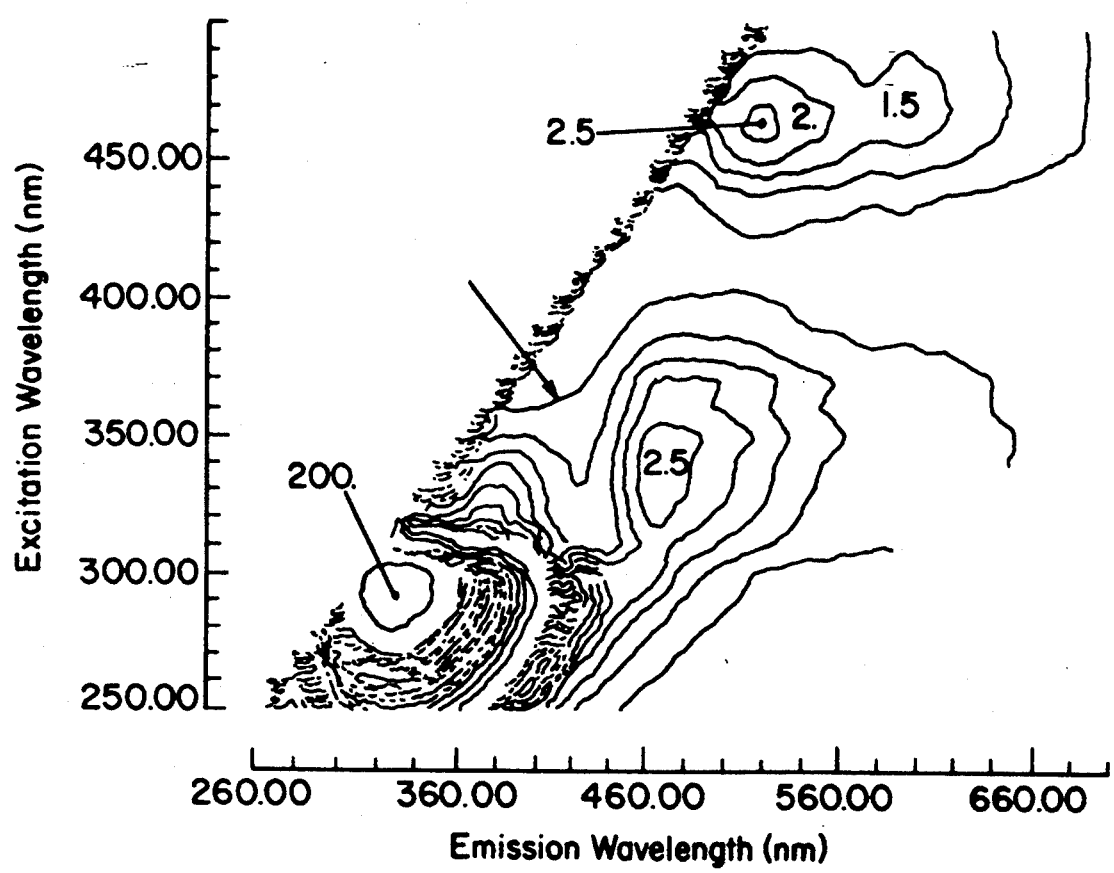
FIG. 42 illustrates an excitation emission matrix of averaged adenomatous colon.

The valleys in the total reflectance spectra can be correlated with the valleys in the average EEMs shown in FIGS. 42 and 42.

Figure 41:
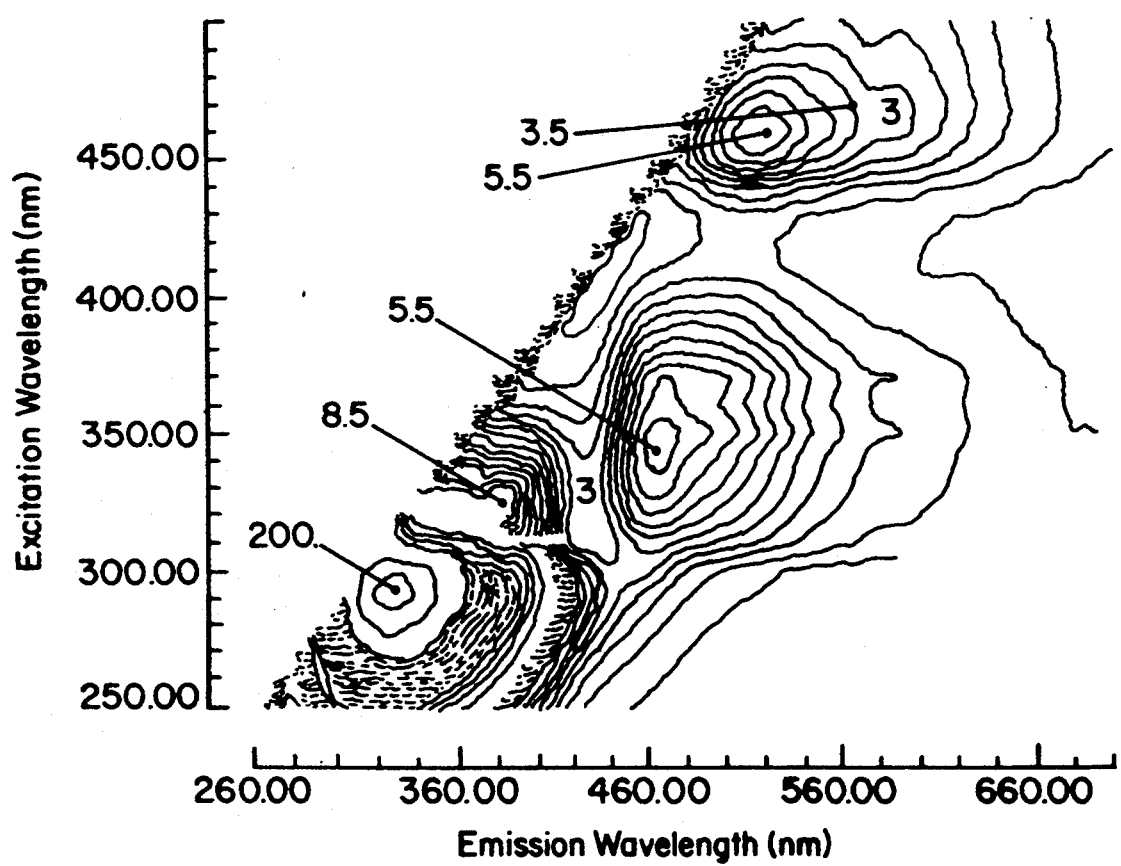
FIG. 41 illustrates an excitation emission matrix of averaged normal human colon.

FIG. 41 illustrates an average EEM of four normal human colon samples. Excitation wavelength is plotted on the ordinate, emission wavelength on the abscissa. Contour lines connect points of equal fluorescence intensities. Three sets of linearly spaced contours are shown: twenty from 0.5 to 10 unites; eighteen from 15 to 100 units; and two from 150 to 200 units. Although fluorescence intensities are given in arbitrary units, the same scale of units is maintained throughout the paper.

FIG. 42 illustrates an average EEM of 11 adenomatous samples. Excitation wavelength is plotted on the ordinate, emission wavelength on the abscissa. Contour lines connect points of equal fluorescence intensities. Three sets of linearly spaced contours are shown: twenty from 0.5 to 10 units; eighteen from 15 to 100 units; and two from 150 to 200 units. Although fluorescence intensities are given in arbitrary units, the same scale of units is maintained throughout the paper.

The strongest attenuation peak at 420 nm gives rise to valleys in the tissue EEMs at 420 nm along both the excitation and emission axes. Although not as prominent, valleys are also present along the emission axis at 540 and 575 nm. A small valley along the excitation axis near 355 nm can also be appreciated.

It is well known that the absorption spectrum of oxy-hemoglobin exhibits peaks near 280, 350, 420, 540, and 580 nm. Thus, nearly all of the attenuation peaks noted in the total reflectance spectra of normal and adenomatous colon in FIG. 38 could be ascribed to oxy-hemoglobin. The presence of oxy-hemoglobin could be attributed to the vascularity of the bowel wall. The gently upward sloping background in the tissue reflectance spectra is likely due to attenuation of other proteings. In general, protein absorption is strong in the UV region, but falls off strongly in the visible. Both extracellular structural proteins (i.e. collagen and elastin) and cellular proteins could contribute to this sloping attentuation.

Potential tissue fluorophores have been identified by comparing excitation/emission peaks in tissue EEMs to those in EEMs of individual tissue constituents as well as peaks cited in the literature. EEMs of these molecules were obtained using the method outlined for tissue above. Excitation/emission maxima are presented here for 1 mM buffered (pH+7.4) isotonic (140 mM NaCl) aqueous solutions of tryptophan, NADH, NADPH, 4-pyridoxic acid, and pyridoxal 5'-phosphate. Date from dry powders of collagen I (bovine achilles tendon), collagen III (calf skin) and elastin (bovine neck ligament) are also given.

Table 7 contains a compendium of excitation/emission maxima from the EEMs of each of the biochemical compounds considered which might contribute to normal and adenomatous colon tissue EEMs. This list should not be considered exhaustive. Tables 2–5 list the local excitation/emission peaks in the colon tissue EEMs as well as our preliminary assignment of tissue fluorophores to these peaks based on comparison with Table 7.

TABLE 7

Summary of Excitation-Emission Maxima in Selected Biologically Important Molecules

| Chromophore | 1 mM Solution/ Dry Powder? | $(\lambda_{exc}, \lambda_{em})$ Maxima[a] |
|---|---|---|
| Tryptophan | Solution | (275, 350 nm) |
| NADH | Solution | (350, 460 nm) |
| NADPH | Solution | (350, 460 nm) |
| 4-Pyridoxic Acid | Solution | (300, 435 nm) |
| Pyridoxal 5'-phosphate | Solution | (305, 375 nm) |
|  |  | (410, 520 nm) |
| Collagen I | Powder | (340, 395 nm) |
|  |  | (270, 395 nm) |
|  |  | (285, 310 nm) |
| Collagen III | Powder | (275, 310 nm) |
|  |  | (330, 390 nm) |
|  |  | (370, 450 nm) |
| Elastin | Powder | (460, 520 nm) |
|  |  | (360, 410 nm) |
|  |  | (425, 490 nm) |
|  |  | (260, 410 nm) |
| Pyridoxic acid lactone [42] |  | (360, 430 nm) |
| Porphyrins [43] |  | (400, 675 nm) |
|  |  | (400, 610 nm) |

[a]Where more than one maxima is given, they are listed in order of decreasing fluorescence intensity.

Note, however, that the band positions in Table 6 do not exactly match the band positions in the earlier Tables. Two effects may be responsible for these differences. Attenuation acts to alter both the observed location of the excitation/emission maxima and observed lineshape of individual tissue fluorophores in the multi-component tissue EEMs when the excitation and emission of individual chromophores closely overlap.

The largest peak in the tissue EEMs near (290, 330 nm) has been assigned to the aromatic amino acid tryptophan, which has a maximum at (275, 350 nm) when in aqueous solution. The small difference in intensity of the tryptophan peak in normal and adenomatous tissues is due either to a difference in the concentration of tryptophan or its environment.

Fluorophores for the tissue peak at (345, 465 nm) include NADH and NADPH. These molecules function as co-enzymes in oxidation-reduction reactions, and both have an excitation/emission maximum at (350, 460 nm) in aqueous solution. It should be noted that the (345, 465 nm) peak is bounded by attenuation valleys at 420 nm along the exciation and emission axes. Thus, the precise location of its excitation/emission maximum can be significantly shifted.

Several peaks which appear in tissue EEMs are near peaks associated with chromophores related to vitamin $B_6$. The peak unique to normal tissue at (315, 430 nm) is near that of 4-pyridoxic acid at (300, 430 nm). The shoulder in adenomatous tissue at (370, 420 nm) is near the reported maximum of pyridoxic acid lactone at (370, 440 nm), Although three peaks are present in the normal and adenomatous tissue EEMs at (460, 530 nm), (465, 555 nm) and (470, 595 nm), they are likely due to a single peak with superimposed oxy-hemoglobin attenuation valleys at 540 and 580 nm. Pyridoxal 5'-phosphate represents a potential candidate for this peak. Its largest excitation/emission maximum is at (410, 520 nm); the shift in the tissue excitation maximum could be attributed to the Soret band attenuation of oxy-hemoglobin. The effects of oxy-hemoglobin attenuation are reduced in the ratio map, and the peak assigned to pyridoxal 5'-phosphate is observed at (400, 480 nm). In addition, pyridoxal 5'-phosphate exhibits a second peak at (305, 385 nm) which is near the peak found at (330, 385 nm) in the normal tissue EEM.

These peaks assigned to pyridoxal 5'-phosphate could also be due to structural protein fluorescence. Elastin fluorescence exhibits a maximum at (460, 520 nm). Collagen I and collagen III fluorescence show peaks at (340, 395 nm) and (330, 390 nm), respectively. Microspectrofluorimetry studies, described later, can separate contributions of extra-and intra-cellular fluorescence, and provide the definitive answer.

Finally, the peaks unique to adenomatous tissue fluorescence at (430, 600 nm) and (430, 670 nm) are due to the presence of endogenous porphyrins. Hematoporphyrin derivative, for example, which is a mixture of several biologically relevant porphyrins, exhibits fluorescence excitation emission maxima near (400, 610 nm) and (400, 675 nm).

As noted above, comparison of EEMs from individual biochemical compounds with optically thick tissue EEMs does not always lead to definitive fluorophore identification, because of potential difficulties created by attenuation and overlapping excitation and emission. Both of these difficulties can be overcome by modeling the tissue EEM in terms of the attenuation and fluorescence properties of individual chromophores.

The peak assigned to NADH or NADPH is twice as intense in normal tissue as in adenomatous tissue EEMs. It is known that the absolute concentrations of NAD+ and NADH decreased 2-3 fold following murine sarcoma virus transformation in rat kidney fibroblasts. The peaks assigned to pyridoxal 5'-phosphate are also approximately twice as intense in the normal tissue as in adenomatous tissue EEMs. Decreased levels of serum pyridoxal 5'-phosphate in cancer patients has been reported. The peaks assigned to porphyrins were most prominent in the adenomatous tissue EEM. An increased content of endogenous porphyrins has been noted in neoplasms of other organ systems.

This has important implications for the interpretation of the tissue emission spectra excited at 370 nm presented earlier. Near 370 nm excitation, potential chromophores identified from the EEMs include the structural proteins, elastin, and type I and III collagen, NADH, NADPH, pyridoxal 5'-phosphate and pyridoxic acid lactone. FIG. 39 shows emission spectra of each of these chromophores (except pyridoxic acid lactone) excited at 370 nm. These spectra represent the 370 nm excited spectrum from the corresponding chromophore fluorescence EEM.

At 370 nm excitation, the emission spectrum of elastin peaks near 450 nm. At this excitation wavelength, collagen I and III show similar emission lineshapes, peaking near 430 nm. NADH and NADPH show similar fluorescence emission spectra at this excitation wavelength, with a peak at 455 nm. The 370 nm excited emission spectrum of pyridoxal 5'-phosphate peaks near 510 nm.

A combination of fluorescence microscopy and light microscopy were used to morphologically identify the fluorescent structures contributing to the 370 nm excited fluorescence emission spectra of colon. Autofluorescent structures within normal and adenomatous colon were identified from unstained frozen sections of tissue using a fluorescence microscope. Serial sections were then stained with various histochemical stains and viewed under the light microscope in order to identify these fluorescent structures at the morphologic level.

Ten specimens of normal colon were obtained from uninvolved areas of resection specimens from 10 patients with rectal adenocarcinoma, diverticular disease or hyperplastic polyps. Six tubular adenomas were collected from colectomy specimens of four patients with familial adenomatous polyposis. Specimens were snap frozen in liquid nitrogen and isopentane and stored at −70° C. until use. Later, specimens were serially cut into 8μm thick sections with a cryostat microtome and stored at −20° C. Before study with the fluorescence microscope, slides were coverslipped with a nonfluorescent aqueous mounting medium (glycerin and phosphate buffered saline, 9:1). Before study with the light microscope serial sections were stained with hemotoxylin and eosin (H&E) and Movat pentachrome stains.

Tissue autofluorescence was viewed using an inverted fluorescence microscope adapted for laser illumination. Multi-line excitation light from 351-364 nm was provided from a CW argon ion laser via a quartz optical fiber. The distal tip of the fiber was positioned at an angle of approximatley 30° to the stage, achieving approximately trans-illumination. A mm diameter field of view was illuminated with this system, the excitation intensity was mW/mm$^2$. A barrier filters (long-pass filter) with a 50% transmission at 420 nm was used to view fluorescence. The morphology, distribution, color and intensity of autofluorescence were recorded for each fluorescent structure in each cryostat section studied.

In normal colon, four layers of the colon could be distinguished based on their autofluorescence: the mucosa, muscularis mucosa, submucosa and muscularis propria. With the 420 nm barrier filter, the submucosa demonstrated an intense, finely fibrillar, blue autofluorescence. This fluorescence could be attributed to collagen fibers in the submucosa, shown in correlated to the presence of collagen fibers, which stain yellow with the Movat pentachrome stain. In the muscularis mucosa and muscularis propria, occasional collagen fibers were present on Movat stain; these also demonstrated a similar blue fibrillar fluorescence.

In the mucosa, three distinctly fluorescent structures could be observed. Collagen fibers in the connective tissue of the lamina propria contributed a blue fibrillar autofluorescence, similar in color, but of weaker intensity relative to that of the submucosa. Yellow-amber, granular fluorescent deposits were also present in the lamina propria, most numerous near the lumenal surface. These were correlated to the presence of eosinophils in serial sections stained with H&E and Movat pentachrome stains. The granules of eosinophils have been previously described as intensely autofluorescence with green excitation. An extremely faint blue-green fluorescence was associated with the fluorescence of absorptive cells. This fluorescence was most prominent near the base and membranes of these cells.

In adenomatous polyps, again all layers of the bowel wall could be distinguished through the fluorescence microscope. The fluorescence of all layers except the mucosa resembled that of normal colon. In the mucosa of adenomatous polyps, again three distinctly fluorescent structures could be recognized. A faint, blue, fibrillar fluorescence, very similar to that observed in the mucosa of normal tissue was observed in the adenomatous mucosa. This fluorescence again correlated to the presence of collagen fibers in the lamina propria by Movat pentachrome stain. Again, yellow-amber fluorescent granules were observed in the mucosa of adenomatous polyps. These were similar in color and intensity to those observed in normal mucosa; however, they were more numerous and more evenly distributed in adenomatous mucosa.

The fluorescence of non-dysplastic absorptive cells within the polyp was quite similar to that of normal tissue. However, the fluorescence of dysplastic epithelial cells differed remarkable from that of non-dysplastic cells. A relatively homogeneous blue green fluoresence was observed within the cytoplasm of these cells. The intensity of this fluorescence appeared to correlate with the grade of dysplasia as determined from serial sections stained with H&E.

In order to interpret tissue fluorescence spectra in terms of contributions from these morpholophores, it is necessary to measure their emission spectra at 370 nm excitation. This was accomplished using a fluorescence microspectrometer. Using this system, 370 nm excited fluorescence emission spectra were recorded from 2 samples of normal colon from uninvolved areas of resection specimens of two patients colonic adenocarcinoma or diverticular disease. Fluorescence spectra were also recorded from four adenomatous polyps obtained from resection specimens of four patients with familial adenomatous polyposis. For each sample, several fluorescence emission spectra were recorded for each of the morpholophores described in the previous section. The 40X objective was used in all cases except for recording fluorescence spectra from absorptive cells, in which case the 100X objective was used.

Each fluorescence spectrum was normalized to unity at the emission wavelength corresponding to peak emission. An average, normalized spectrum was calculated for each morpholophore in normal and adenomatous tissue. A morpholophore is defined as a histologically distinct material that exhibits autofluorescence. In cases where no significant differences were observed in the average normal and adenomatous morpholophore spectrum, an average spectrum was computed for all data. FIG. 45 shows the resulting average spectra for each morpholophore.

The fluorescence lineshape recorded from collagen fibers in the submucosa of normal and adenomatous tissues was the same, peaking near 430 nm. The fluorescence lineshape of collagen fibers in the lamina propria of normal mucosa exhibited an identical lineshape. However, the fluorescence lineshape of collagen fibers in adenomatous mucosa was unique, exhibiting a broader fluorescence peak, with a maxima near 460 nm. Mucosal eosinophils in normal and adenomatous colon showed similar fluorescence lineshapes, consisting of a broad peak, centered at 480 nm. Absorptive cells in adenomatous mucosa displayed a broad fluorescence peak, with a maximum near 520 nm. The fluorescence emission spectra of absorptive cells in normal mucosa was exceedingly weak. The recorded signal was indistinguishable from that of lamina propria connective tissue, indicating possibly that the signal was too weak to be accurately recorded with this system.

These lineshapes can now be used to interpret the fluorescence spectra of tissue presented earlier at a morphologic level. In the average spectrum of normal colon obtained with this system, the peak at 460 nm can be attributed to the emission of collagen fibers in the submucosa and lamina propria. Although these morpholophores have an emission which peaks around 430 nm, the Soret absorption band of oxyhemoglobin acts to shift the observed location of the maximum. The subsidiary maxima at 480 nm is this average spectrum is likely due to the fluorescence of eosinophils within the mucosa.

In the average adenoma spectrum, the peak at 460 nm can also be attributed to collagen fibers within the submucosa and lamina propria. Relative to normal colon, the intensity of this peak is decreased in adenomatous tissues. This is likely due to the increase in mucosal thickness of adenomatous polyps. The brightly fluorescent collagen fibers in the submucosa are further from the lumen, and thus, contribute less to the overall spectrum. Again, the Soret band of oxy-hemoglobin acts to shift the observed potion of this maximum. Eosinophil fluorescence also contributes to the fluorescence spectrum of adenomatous colon. However, the 480 nm peak in adenoma spectra is less prominent than that in normal colon spectra for potentially two reasons. First, the fluorescence emission of collagen in the adenomatous lamina propria is quite broad, and substantially overlaps the eosinophil emission. Second, the distribution of eosinophils is more uniform in adenomas, thus their overall contribution to the fluorescence spectrum is decreased. Finally, the peak at 520 nm observed in the adenoma spectrum can be attributed to the fluorescence of dysplastic absorptive cells.

Although microspectroscopy can be used to identify and characterize tissue morpholophores, this technique provides limited insight about the chemical basis of tissue fluorescence. However, using EEMs, we were able to provide potential chemical identification of tissue fluorophores. A comparison of these identifications should provide valuable insight into definitively establishing the histochemical basis of tissue fluorescence. Essentially by comparing the 370 nm excited fluorescence spectrum of individual morpholophores with those of chromophores presented earlier (FIG. 43), the self consistency of these suggested chemical identifications can be tested. Chemically identified fluorophores, this identification can be supported.

A comparison of the fluorescence lineshape of submucosal collagen and collagen in the normal lamina propria shows that this emission is consistent with that of type I collagen. The emission lineshape of collagen in the adenomatous lamina propria more closely matches that of type III collagen. Although this emission spectrum is also consistent with that of NADH and NADPH, the localization that we can achieve with microspectroscopy shows that this is not likely the correct identification. None of the potential fluorophores identified chemically matches the emission lineshape observed from eosinophils at this excitation wavelength. Eosinophil autofluorescence is associated with eosinophil granules. Finally, the emission maxima of dysplastic absorptive cells matches that of pyridoxal 5' phosphate. However, there is more fluorescence observed in the blue region of this morpholophore than is observed in the chromophore. The weak level of fluorescence of this morpholophore makes it difficult to definitively rule out this possible chemical identification.

We claim:

1. A method of diagnosing gastrointestinal tissue to determine the presence of abnormal tissue comprising:
exciting fluorophores within a portion of gastrointestinal tissue with light at a predetermined wavelength which causes the fluorophores within the tissue to emit autofluorescent radiation of a plurality of wavelengths without the presence of a fluorescence enhancing agent;
detecting the autofluorescent radiation emitted by the fluorophores within the tissue in response to excitation from the light to provide an emission spectrum;
forming an attenuation spectrum and comDarinq the attenuation spectrum with the emission spectrum to identify fluorophores within the tissue; and
analyzing the emission spectrum to determine the presence of abnormal tissue within the portion of tissue containing the excited fluorophores by comparing the emission spectrum to a reference emission for normal tissue at a plurality of predetermined wavelengths.

2. The method of diagnosing gastrointestinal tissue of claim 1 wherein the analyzing step further comprises determining a ratio of an intensity of the emission fluorescence at one of the emission wavelengths with an intensity of the emission fluorescence at another of the emission wavelengths and comparing the ratio with a threshold ratio for normal tissue.

3. The method of diagnosing gastrointestinal tissue of claim 2 further comprising determining the ratio of wavelengths having a maximum separation between normal and abnormal tissue.

4. The method of diagnosing gastrointestinal tissue of claim 2 wherein the excitation wavelength is 290 nm and the emission wavelength ratio is selected from the group of wavelengths consisting of about 335 nm/365 nm, 335 nm/440 nm, 440 nm/390 nm, 415 nm/425 nm, or 440 nm/457 nm.

5. The method of diagnosing gastrointestinal tissue of claim 2 wherein the excitation wavelength is 350 nm and the emission wavelength ratio is selected from the group of wavelengths consisting of 387 nm/365 nm, 387 nm/427 nm, 415 nm/425 nm, 440 nm/457 nm, 495 nm/440 nm, or 475 nm/440 nm.

6. The method of diagnosing gastrointestinal tissue of claim 1 to determine the presence of abnormal tissue further comprising: exciting fluorophores within a portion of the gastrointestinal tissue with light having a wavelength in a range between 200 and 400 nanometers such that the fluorophores within the tissue fluoresces; and
detecting radiation emitted by the fluorophores within the tissue having a wavelength in a range between 300 and 600 nanometers.

7. The method of diagnosing gastrointestinal tissue of claim 6 further comprising identifying a plurality of selected wavelengths in the emission range that distinguish between normal and abnormal tissue and comparing the emitted radiation at the selected wavelengths with a reference emission for normal tissue at the selected wavelengths.

8. The method of diagnosing gastrointestinal tissues of claim 6 wherein the excitation wavelength is within the range between 330 and 370 nanometers.

9. The method of diagnosing gastrointestinal tissues of claim 6 wherein the emission wavelength is about 440 nanometers.

10. The method of diagnosing gastrointestinal tissue of claim 6 wherein the emission wavelength is about 470 nanometers.

11. The method of diagnosing gastrointestinal tissue of claim 6 wherein the emission wavelength is about 385 nanometers.

12. The method of diagnosing gastrointestinal tissue of claim 6 wherein the emission wavelength is about 560 nanometers.

13. The method of diagnosing gastrointestinal tissue of claim 1 wherein the exciting step further comprises:
  inserting a fiber optic probe having an optical fiber into a body lumen;
  contacting the tissue to be diagnosed with a distal surface of the fiber optic probe such that radiation transmitted along the fiber will be directed onto the tissue from the distal surface;
  coupling a source of laser radiation to a proximal end of the fiber optic probe such that laser radiation is transmitted along the optical fiber and onto the tissue; and wherein the detecting step further comprises
  transmitting autofluorescent radiation emitted by the fluorophores within the tissue from the distal end of the fiber optic probe to the proximal end.

14. The method of diagnosing gastrointestinal tissue of claim 13 wherein the analyzing step further comprises comparing a characteristic of the detected radiation with a reference signal to determine the presence of abnormal tissue within the irradiated portion.

15. The method of diagnosing gastrointestinal tissue of claim 1 wherein the fluorophores are selected from the group consisting of tryptophan, NADH, NADPH, 4-pyridoxic acid, pyridoxal 5'-phosphate, pyridoxic acid lactone and porphyrins.

16. The method of diagnosing gastrointestinal tissue of claim 15 wherein the fluorophores are excited with light of wavelengths selected from the group consisting of about 275 nm, 300 nm, 305 nm, 350 nm, 360 nm, 400 nm and 410 nm.

17. The method of diagnosing gastrointestinal tissue of claim 16 wherein the radiation emitted by the fluorophores is of wavelengths selected from the group consisting of about 350 nm, 375 nm, 430 nm, 435 nm, 460 nm, 520 nm, 610 nm and 675 nm.

18. A method of determining a function for diagnosing gastrointestinal tissue comprising:
  irradiating fluorophores within a portion of gastrointestinal tissue with light of selected wavelength from a laser;
  inducing autofluorescence of the fluorophores within the portion of tissue;
  detecting the autofluorescent radiation emitted by the fluorophores within the tissue;
  generating an emission spectrum from the detected radiation;
  determining a difference spectrum by calculating the difference between the emission spectrum and a reference spectrum;
  selecting a first wavelength from the difference spectrum where the irradiated portion has a relative maximum fluorescence in relation to surrounding wavelengths;
  selecting a second wavelength from the difference spectrum where the reference spectrum has a relative maximum fluorescence in relation to surrounding wavelengths; and
  determining a diagnostic function from the first and second wavelengths to differentiate abnormal from normal tissue.

19. The method of claim 18 further comprising:
  determining a first standard deviation spectrum for the reference spectrum and determining a second standard deviation spectrum from the emission spectrum;
  determining a discriminant spectrum from the difference spectrum and the first and second deviation spectrum;
  selecting wavelengths within the discriminant spectrum to form a diagnostic function to differentiate abnormal from normal tissue.

20. The method of diagnosing gastrointestinal tissue of claim 18 wherein the fluorophores are selected from the group consisting of tryptophan, NADH, NADPH, 4-pyridoxic acid, pyridoxal 5'-phosphate, pyridoxic acid lactone and porphyrins.

21. The method of diagnosing gastrointestinal tissue of claim 20 wherein the fluorophores are irradiated with light of wavelengths selected from the group consisting of about 275 nm, 300 nm, 305 nm, 350 nm, 360 nm, 400 nm and 410 nm.

22. The method of diagnosing gastrointestinal tissue of claim 21 wherein the radiation emitted by the fluorophores is of wavelengths selected from the group consisting of about 350 nm, 375 nm, 430 nm, 435 nm, 460 nm, 520 nm, 610 nm and 675 nm.

23. A diagnostic probe to determine the presence of abnormal tissue comprising:
  a source of laser radiation having a wavelength of between about 370 nm and about 450 nm;
  a fiber optic probe having a plurality of optical fibers such that a first fiber is coupled to the radiation source at a proximal end and directs the radiation onto an irradiated area of tissue containing fluorophores adjacent a distal end of the first fiber to induce autofluorescence of the fluorophores, the plurality of fibers including a collection fiber that is positioned relative to the plurality of fibers to receive autofluorescent radiation from only the fluorophores within the irradiated area of tissue;
  an analyzer coupled to a proximal end of the collection fiber that receives and analyzes the fluorescent radiation from the fluorophores within the irradiated area at wavelengths longer than 400 nm.

24. The diagnostic probe of claim 23 wherein the analyzer generates a signal correllated with the intensity of the fluorescent radiation at 460 nm, 25. The diagnostic probe of claim 23 further comprising a plurality of collection fibers.

26. The diagnostic probe of claim 23 further comprising a second laser source to deliver an energy pulse to the tissue to treat the tissue.

* * * * *